(12) United States Patent
Phillion et al.

(10) Patent No.: US 6,252,078 B1
(45) Date of Patent: Jun. 26, 2001

(54) FUNGICIDES FOR THE CONTROL OF TAKE-ALL DISEASE OF PLANTS

(75) Inventors: Dennis Paul Phillion, St. Charles, MO (US); Diane Susan Braccolino, Copley, OH (US); Matthew James Graneto, St. Louis, MO (US); Wendell Gary Phillips, Glencoe, MO (US); Karey Alan Van Sant, St. Charles, MO (US); Daniel Mark Walker, Maryland Heights, MO (US); Sai Chi Wong, Chesterfield, MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/162,032

(22) Filed: Sep. 28, 1998

Related U.S. Application Data

(62) Division of application No. 08/365,382, filed on Dec. 28, 1994, now Pat. No. 5,849,723, which is a division of application No. 08/238,182, filed on May 4, 1994, now abandoned, which is a continuation of application No. 07/951,997, filed on Oct. 2, 1992, now abandoned, which is a continuation-in-part of application No. 07/780,683, filed on Oct. 18, 1991, now abandoned.

(51) Int. Cl.$^7$ .......................... C07F 7/02; C07D 215/38; A61K 31/44
(52) U.S. Cl. .............................. 546/14; 546/169; 514/354
(58) Field of Search ....................... 546/169, 14; 514/354

(56) References Cited

U.S. PATENT DOCUMENTS

| | | | |
|---|---|---|---|
| 4,228,165 | * 10/1980 | Ogata et al. | 424/248.5 |
| 4,248,869 | 2/1981 | Ogata et al. | 424/248.5 |

(List continued on next page.)

FOREIGN PATENT DOCUMENTS

| | | |
|---|---|---|
| 0 243 668 A3 | 3/1987 | (EP) . |
| 0 234 119 | 9/1987 | (EP) . |

(List continued on next page.)

OTHER PUBLICATIONS

Abiko, et al., *Pergamon Journals,* Ltd., pp. 4537–4540 (1986).

(List continued on next page.)

Primary Examiner—Deborah C. Lambkin
(74) Attorney, Agent, or Firm—Thomas McBride; Howrey Simon Arnold & White LLP

(57) ABSTRACT

A method of controlling Take-all disease of plants by applying, preferably to the seed prior to planting, a fungicide of the formula

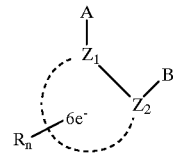

wherein $Z_1$ and $Z_2$ are C or N and are part of an aromatic ring selected from benzene, pyridine, thiophene, furan, pyrrole, pyrazole, thiazole, and isothiazole;

A is selected from —C(X)-amine, —C(O)—SR$_3$, —NH—C(X)R$_4$, and —C(=NR$_3$)—XR$_7$;

B is —W$_m$—Q(R$_2$)$_3$ or selected from o-tolyl, 1-naphthyl, 2-naphthyl, and 9-phenanthryl, each optionally substituted with halogen or R$_4$;

Q is C, Si, Ge, or Sn;

W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$—, and —O—;

X is O or S;

n is 0, 1, 2, or 3;

m is 0 or 1;

p is 0, 1, or 2;

each R is independently selected from
  a) halo, formyl, cyano, amino, nitro, thiocyanato, isothiocyanato, trimethylsilyl, and hydroxy;
  b) C1–C4 alkyl, alkenyl, alkynyl, C3–C6 cycloalkyl, and cycloalkenyl, each optionally substituted with halo, hydroxy, thio, amino, nitro, cyano, formyl, phenyl, C1–C4 alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;
  c) phenyl, furyl, thienyl, pyrrolyl, each optionally substituted with halo, formyl, cyano, amino, nitro, C1–C4 alkyl, alkenyl, alkynyl, alkoxy, alkylthio, alkylamino, dialkylamino, haloalkyl, and haloalkenyl;
  d) C1–C4 alkoxy, alkenoxy, alkynoxy, C3–C6 cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

wherein two R groups may be combined to form a fused ring;

each R$_2$ is independently selected from alkyl, alkenyl, alkynyl, cycloalkyl, cycloalkenyl and phenyl, each optionally substituted with R$_4$ or halogen; and wherein, when Q is C, R$_2$ may also be selected from halo, alkoxy, alkylthio, alkylamino, and dialkylamino;

wherein two R$_2$ groups may be combined to form a cyclo group with Q;

R$_3$ is C1–C4 alkyl;

R$_4$ is C1–C4 alkyl, haloalkyl, alkoxy, alkylthio, alkylamino, or dialkylamino; and R$_7$ is C1–C4 alkyl, haloalkyl, or phenyl, optionally substituted with halo, nitro, or R$_4$;

or an agronomic salt thereof.

10 Claims, No Drawings

U.S. PATENT DOCUMENTS

| | | | |
|---|---|---|---|
| 4,485,105 | 11/1984 | Ghepord et al. | 424/248.54 |
| 4,997,836 | 3/1991 | Sugihara et al. | 514/253 |
| 4,999,381 | 3/1991 | Crowley et al. | 514/618 |

FOREIGN PATENT DOCUMENTS

| | | | |
|---|---|---|---|
| 0243 668 | 11/1987 | (EP) | . |
| 0 335 831 A1 | 7/1989 | (EP) | . |
| 0 550 900 A1 * | 7/1993 | (EP) | . |
| 118825 | 7/1983 | (JP) | . |
| 63-284186 | 11/1988 | (JP) | . |
| WO 91/01311 | 7/1990 | (WO) | . |

OTHER PUBLICATIONS

Eiglsperger, A., et al., "The Enantiomers Of N,N–Dimethylthiobenzamides: Chromatographic Behavior And Rotational Barriers," *J. of Molecular Structure*, vol. 126, pp. 421–432 (1985).

Fitt, J. J., et al., "Ortho Lithiation Of Thiobenzamides," *J. of Organic Chemistry*, vol. 41, No. 25, pp. 4029–4031 (1976).

Fu, J. M., et al., "The Directed Ortho Metalation Connection To Aryl–Aryl Cross Coupling, A General Regiospecific Synthesis Of Phenanthrols," *Tetrahedron Letters*, vol. 29, No. 43, pp. 5459–5462 (1988).

Gajda, et al., "Phase–Transfer–Catalysed N–Alkylation Of Carboxamides And Sulfonamides," pp. 1005–1008 (Dec. 1981).

Grimshaw, J., et al., "Electrochemical Reactions. Intermolecular Radical Substitution During The Reduction of 2–Halo–N–Methylbenzamides," *J. of Chem. Soc.*, Perkin Trans., No. 22, pp. 12448–2455 (1977).

Gupton, et al., "Regioselective Fluoroalkoxylation And Polyfluoroalkoxylation Of Activated Polyhalobenzenes," *Synthetic Communications*, 14(7), pp. 621–629 (1984).

Ishibashi, H., et al., "Friedel–Crafts Alkylation Of Phenyl Silanes With Alpha–Chloro Sulfides," *Chem. Lett.*, No. 4, pp. 603–606 (1989) (Chemical Abstract No. 112(1):7560x).

Linke, S., "N–Alkylcarboxamide And Nitriles," *1978 Georg Thieme Publishers*, pp. 303–304 (Apr. 1978).

McDonald, J. E., et al., "An Anomalous Metalation Of A Trimethylsilyl Group," *Tetrahedron Letters*, vol. 28, No. 17, pp. 1851–1852 (1987).

Mills, R. J., et al., "Directed Ortho Metalation Of N,N–Diethylbenzamides: Silicon Protection Of Ortho Sites And The O–Methyl Group," *J. Org. Chem.*, vol. 54, pp. 4372–4385 (1989).

Mills, R. J., et al., "Dilithiated Synthons Of Tertiary Benzamides, Phthalamides, And O,O'–Aryl Dicarbamates," *Tetrahedron Letters*, vol. 26, No. 9, pp. 1145–1148 (1985).

Ogata, Y., et al., "Photochemical Ethoxycarbonylmethylation Of Alkylbenzenes With Ethyl Chloroacetate, MO Calculation For Prediction Of Orientation," *Bull. of Chem. Soc. of Japan*, vol. 51, No. 12, pp. 3657–3658 (1978) (Chemical Abstract No. 90(15):120661w).

Reuvers, A. J. M., et al., "Chemistry Of Neopentyl Derivatives–II. Restricted Rotation In 2,6–Disubstituted Neopentylbenzenes," *Tetrahedron Letters*, vol. 27, pp. 3713–3721 (1971).

Salituro, F. G., et al., "Facile Synthesis Of L–Kynurenine," *J. of Organic Chemistry*, vol. 53, No. 26, pp. 6138–6139 (1988).

Sandifer, R. M., et al., "Silation At The Ortho Position Of N–Methyl And N–Phenylbenzamide," *Chemistry and Industry* (Mar. 19, 1977).

Slocum, D. W., et al., "Directed Metallation Of Model Adrenaline Compounds," *J.C.S. Chem. Comm.*, pp. 268–269 (1974).

Snieckus, Victor, "Directed Ortho Metalation: Tertiary Amide And o–Carbamate Directors In Synthetic Strategies For Polysubstituted Aromatics," *Chemical Reviews*, vol. 90, No. 6, pp. 879–933 (1990).

Takahashi, Y., et al., "Application Of The ORMUCS Method To Structure–Activity Studies On The Fungicidal Activity Of Mepronil Derivatives," *Quant. Struct.–Act. Relat.*, vol. 6, No. 1, pp. 17–21 (1987).

Ukita, M., et al., "Thermal Dissociation Of Ethyl N–Arylcarbamates In A Vapor Phase," *Osaka Kogyo Gijutsu Shikensho Kiho*, vol. 36, No. 2, pp. 53–58 (1985) (Chemical Abstract No. 104(9):68369y).

Derwent Abstract No. 87/203436/29, Hitashi, Heat Transfer Ink Film, J6 213676 (Apr. 12, 1985).

Derwent Abstract No. 89/013361/09, Hara Chem. Ind., Aromatic Nitrile And Aromatic Carboxylic Acid Cpds. Prepn. (May 25, 1987).

Derwent Abstract No. 90/213193/28, Hara Chem. Ind., Production Of Aromatic Nitrile(s) For Agrochemicals, etc. (Jan. 25, 1988).

Derwent Abstract No. 91/061915/09, Konica Corp., Heat Transfer Recording Sheet (Jun. 8, 1989).

Derwent Abstract No. 93/062565/08, Ricoh KK, Electrostatic Or Electrophotographic Developer Appts. Using One Component Developer (Jan. 10, 1991).

Derwent Abstract No. 08/06/91, Otsuka Pharm. Co. Ltd., Aromatic Fluorine Cpds. Prepn. Useful As Intermediates For Pharmaceuticals (Aug. 6, 1991).

CA 63:9901d Jul.–Dec. 1965.
CA 63:9901g Jul.–Dec. 1965.
CA 66:55192 Jan.–Jun. 1967.
CA 67:48875 Jul.–Dec. 1967.
CA 68:86697 Jan.–Jun. 1968.
CA 68:105285 Jan.–Jun. 1968.
CA 68:106060 Jan.–Jun. 1968.
CA 69:27791 Jul.–Dec. 1968.
CA 70:20213 Jan.–Jun. 1969.
CA 71:12226 Jul.–Dec. 1969.
CA 71:30136 Jul.–Dec. 1969.
CA 72:54910 Jan.–Jun. 1970.
CA 74:88644 Jan.–Jun. 1971.
CA 74:125523 Jan.–Jun. 1971.
CA 75:98613 Jul.–Dec. 1971.
CA 76:159639 Jan.–Jun. 1972.
CA 80:37345 Jan.–Jun. 1974.
CA 82:43628 Jan.–Jun. 1975.
CA 82:112118 Jan.–Jun. 1975.
CA 83:58380 Jul.–Dec. 1975.
CA 83:113683 Jul.–Dec. 1975.
CA 83:131788 Jul.–Dec. 1975.
CA 83:192056 Jul.–Dec. 1975.
CA 84:150377 Jan.–Jun. 1976.
CA 86:5107 Jan.–Jun. 1977.
CA 87:6050 Jul.–Dec. 1977.
CA 87:85074 Jul.–Dec. 1977.
CA 88:136419 Jan.–Jun. 1978.
CA 89:138369 Jul.–Dec. 1978.
CA 90:152273 Jan.–Jun. 1979.
CA 90:186813 Jan.–Jun. 1979.
CA 91:39060 Jul.–Dec. 1979.
CA 91:66218 Jul.–Dec. 1979.

CA 91:74313 Jul.–Dec. 1979.
CA 91:74332k Jul.–Dec. 1979.
CA 91:187234 Jul.–Dec. 1979.
CA 93:194922 Jul.–Dec. 1980.
CA 93:132272 Jul.–Dec. 1980.
CA 93:204202 Jul.–Dec. 1980.
CA 94:55848 Jan.–Jun. 1981.
CA 95:115322 Jul.–Dec. 1981.
CA 98:179476 Jan.–Jun. 1983.
CA 99:40778 Jul.–Dec. 1983.
CA 99:176047d Jul.–Dec. 1983.
CA 100:5549 Jan.–Jun. 1984.
CA 100:67950 Jan.–Jun. 1984.
CA 100:85771 Jan.–Jun. 1984.
CA 101:6916 Jul.–Dec. 1984.
CA 101:6917 Jul.–Dec. 1984.
CA 101:91300 Jul.–Dec. 1984.
CA 101:110650 Jul.–Dec. 1984.
CA 101:192028 Jul.–Dec. 1984.
CA 102:6123 Jan.–Jun. 1985.
CA 102:19477g Jan.–Jun. 1985.
CA 102:220266 Jan.–Jun. 1985.
CA 102:220349 Jan.–Jun. 1985.
CA 103:101888w Jan.–Jun. 1985.
CA 103:104657 Jul.–Dec. 1985.
CA 104:102136 Jan.–Jun. 1986.
CA 105:6316 Jul.–Dec. 1986.
CA 105:114881 Jul.–Dec. 1986.
CA 105:115261 Jul.–Dec. 1986.
CA 106:18386x Jan.–Jun. 1987.
CA 106:151496 Jan.–Jun. 1987.
CA 106:213560 Jan.–Jun. 1987.
CA 107:22754 Jul.–Dec. 1987.
CA 107:175640 Jul.–Dec. 1987.
CA 107:187230 Jul.–Dec. 1987.
CA 108:56413 Jan.–Jun. 1988.
CA 108:131232 Jan.–Jun. 1988.
CA 108:221759 Jan.–Jun. 1988.
CA 109:54382 Jul.–Dec. 1988.
CA 109:54417 Jul.–Dec. 1988.
CA 109:54441 Jul.–Dec. 1988.
CA 109:55027 Jul.–Dec. 1988.
CA 109:230711 Jul.–Dec. 1988.
CA 110:8628 Jan.–Jun. 1989.
CA 110:192411 Jan.–Jun. 1989.
CA 110:193223 Jan.–Jun. 1989.
CA 110:231500u Jan.–Jun. 1989.
CA 111:152391 Jul.–Dec. 1989.
CA 111:152392 Jul.–Dec. 1989.
CA 111:174473 Jul.–Dec. 1989.
CA 111:115055 Jul.–Dec. 1989.
CA 111:133871 Jul.–Dec. 1989.
CA 111:153314 Jul.–Dec. 1989.
CA 111:194246 Jul.–Dec. 1989.
CA 112:20878 Jan.–Jun. 1990.
CA 112:118393 Jan.–Jun. 1990.
CA 113:23608 Jul.–Dec. 1990.
CA 113:23645 Jul.–Dec. 1990.
CA 113:23669 Jul.–Dec. 1990.
CA 113:78409m Jul.–Dec. 1990.
CA 114:5997 Jan.–Jun. 1991.
CA 114:96801h Jan.–Jun. 1991.
CA 114:117809 Jan.–Jun. 1991.
CA 114:122776 Jan.–Jun. 1991.
CA 114:132997 Jan.–Jun. 1991.
CA 114:163423 Jan.–Jun. 1991.
CA 114:163688 Jan.–Jun. 1991.
CA 114:207214 Jan.–Jun. 1991.
CA 114:229206 Jan.–Jun. 1991.
CA 114:229210 Jan.–Jun. 1991.
CA 115:8509 Jul.–Dec. 1991.
CA 115:91783 Jul.–Dec. 1991.
CA 115:231943 Jul.–Dec. 1991.
CA 116:21273 Jan.–Jun. 1992.
CA 116:72359 Jan.–Jun. 1992.
CA 116:83516 Jan.–Jun. 1992.
CA 116:83737 Jan.–Jun. 1992.
CA 116:128686 Jan.–Jun. 1992.
CA 116:128746 Jan.–Jun. 1992.
CA 116:140021 Jan.–Jun. 1992.
CA 116:209745 Jan.–Jun. 1992.
CA 116:255556 Jan.–Jun. 1992.
CA 117:48058 Jul.–Dec. 1992.
CA 117:48551 Jul.–Dec. 1992.
CA 117:69858 Jul.–Dec. 1992.
CA 117:111341 Jul.–Dec. 1992.
CA 117:245405 Jul.–Dec. 1992.
CA 117:251783 Jul.–Dec. 1992.
CA 118:38751 Jan.–Jun. 1993.
CA 118:124594 Jan.–Jun. 1993.
CA 118:147272 Jan.–Jun. 1993.

* cited by examiner

FUNGICIDES FOR THE CONTROL OF TAKE-ALL DISEASE OF PLANTS

This application is a Division of Ser. No. 08/365,382 filed Dec. 28, 1994, U.S. Pat. No. 5,849,723, which is a Division of Ser. No. 08/238,182 filed May 4, 1994 abandoned, which is a continuation of Ser. No. 07/951,997 filed Oct. 2, 1992 abandoned, which is a CIP of Ser. No. 07/780,683 filed Oct. 18, 1991 abandoned.

FIELD OF THE INVENTION

This invention relates to a method for the control of Take-All disease in plants, particularly cereals, by the use of certain substituted aryl compounds, some of which are novel, and fungicidal compositions for carrying out the method.

BACKGROUND OF THE INVENTION

Take-all disease is a serious problem in the production of cereals, particularly wheat and barley. It is caused by the soil-borne fungus *Gaeumannomyces graminis* (Gg). The fungus infects the roots of the plant, and grows throughout the root tissue, causing a black rot. The growth of the fungus in the roots and lower stem prevents the plant from obtaining sufficient water and/or nutrients from the soil, and is manifested as poor plant vigor and, in severe instances of disease, by the formation of "whiteheads," which are barren or contain few, shriveled grains. Yield losses result. Gaeumannomyces species also infect other cereal crops, for example, rice and oats; and turf.

Currently the primary means of avoiding crop loss due to infestation of the soil by Gg has been to rotate the crop grown to one which is resistant to Gg. However, in areas where the primary crops are cereals, rotation is not a desirable practice, and an effective control agent is greatly desired.

It is an object of this invention to provide an effective method for control of Take-all disease in plants. It is a further object of this invention to provide compounds that control the growth of Gg in the soil so as to reduce crop loss. It is still a further object of this invention to provide fungicidal compositions that may be used for control of Take-all disease.

SUMMARY OF THE INVENTION

The present invention provides a method of controlling disease caused by Gaeumannomyces species in plants comprising applying to the plant locus, that is, the plant itself, its seed, or the soil, a fungicidally effective amount of a fungicide of the formula

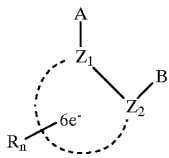

wherein $Z_1$ and $Z_2$ are C or N and are part of an aromatic ring selected from benzene, pyridine, thiophene, furan, pyrrole, pyrazole, thiazole, and isothiazole;

A is selected from —C(X)-amine, —C(O)—SR$_3$, —NH—C(X)R$_4$, and —C(=NR$_3$)—XR$_7$;

B is —W$_m$—Q(R$_2$)$_3$ or selected from o-tolyl, 1-naphthyl, 2-naphthyl, and 9-phenanthryl, each optionally substituted with halogen or R$_4$;

Q is C, Si, Ge, or Sn;

W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$—, and —O—;

X is O or S;

n is 0, 1, 2, or 3;

m is 0 or 1;

p is 0, 1, or 2;

each R is independently selected from
  a) halo, formyl, cyano, amino, nitro, thiocyanato, isothiocyanato, trimethylsilyl, and hydroxy;
  b) C1–C4 alkyl, alkenyl, alkynyl, C3–C6 cycloalkyl, and cycloalkenyl, each optionally substituted with halo, hydroxy, thio, amino, nitro, cyano, formyl, phenyl, C1–C4 alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;
  c) phenyl, furyl, thienyl, pyrrolyl, each optionally substituted with halo, formyl, cyano, amino, nitro, C1–C4 alkyl, alkenyl, alkynyl, alkoxy, alkylthio, alkylamino, dialkylamino, haloalkyl, and haloalkenyl;
  d) C1–C4 alkoxy, alkenoxy, alkynoxy, C3–C6 cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

wherein two R groups may be combined to form a fused ring;

each R$_2$ is independently selected from alkyl, alkenyl, alkynyl, cycloalkyl, cycloalkenyl and phenyl, each optionally substituted with R$_4$ or halogen; and wherein, when Q is C, R$_2$ may also be selected from halo, alkoxy, alkylthio, alkylamino, and dialkylamino;

wherein two R$_2$ groups may be combined to form a cyclo group with Q;

R$_3$ is C1–C4 alkyl;

R$_4$ is C1–C4 alkyl, haloalkyl, alkoxy, alkylthio, alkylamino, or dialkylamino;

R$_7$ is C1–C4 alkyl, haloalkyl, or phenyl, optionally substituted with halo, nitro, or R$_4$;

or an agronomic salt thereof.

The term "amine" in —C(X)-amine means an unsubstituted, monosubstituted, or disubstituted amino radical, including nitrogen-bearing heterocycles. Examples of substituents for the amino radical include, but are not limited to, hydroxy; alkyl, alkenyl, and alkynyl, which may be straight or branched chain or cyclic; alkoxyalkyl; haloalkyl; hydroxyalkyl; alkylthio; alkylthioalkyl; alkylcarbonyl; alkoxycarbonyl; aminocarbonyl; alkylaminocarbonyl; cyanoalkyl; mono- or dialkylamino; phenyl, phenylalkyl or phenylalkenyl, each optionally substituted with one or more C1–C6 alkyl, alkoxy, haloalkyl, C3–C6 cycloalkyl, halo, or nitro groups; C1–C4 alkyl or alkenyl groups substituted with heterocycles, optionally substituted with one or more C1–C4 alkyl, alkoxy, haloalkyl, halo, or nitro groups. Examples of such nitrogen-bearing heterocycles, which are bonded at a nitrogen to —C(X)—, include, but are not limited to, morpholine, piperazine, piperidine, pyrrole, pyrrolidine, imidazole, and triazoles, each of which may be optionally substituted with one or more C1–C6 alkyl groups.

Specific examples of the amino radicals useful in the present invention include, but are not limited to, ethylamino, methylamino, propylamino, 2-methylethylamino, 1-propenylamino, 2-propenylamino, 2-methyl-2-propenylamino, 2-propynylamino, butylamino, 1,1-dimethyl-2-propynylamino, diethylamino, dimethylamino, N-(methyl)ethylamino, N-(methyl)-1,1-(dimethyl)ethylamino, dipropylamino, octylamino, N-(ethyl)-1-methylethylamino, 2-hydroxyethylamino, 1-methylpropylamino, chloromethylamino, 2-chloroethylamino, 2-bromoethylamino, 3-chloropropylamino, 2,2,2-trifluoroethylamino, cyanomethyl, methylthiomethylamino, (methylsulfonyl) oxyethylamino, 2-ethoxyethylamino, 2-methoxyethylamino, N-(ethyl)-2-ethoxyethylamino, 1-methoxy-2,2-dimethylpropylamino, cyclopropylamino, cyclobutylamino, cyclopentylamino, cyclohexylamino, methoxymethylamino, N-(methoxymethyl)ethylamino, N-(1-methylethyl)propylamino, 1-methylheptylamino, N-(ethyl)-1-methylheptylamino, 6,6-dimethyl-2-hepten-4-ynylamino, 1,1-dimethyl-2-propynylamino. Further examples include benzylamino, ethylbenzylamino, 3-methoxybenzylamino, 3-(trifluoromethyl)benzylamino, N-methyl-3-(trifluoromethyl)benzylamino, 3,4,5-trimethoxybenzylamino, 1,3-benzodioxol-5-ylmethylamino, phenylamino, 3-(1-methylethyl)phenylamino, ethoxyphenylamino, cyclopentylphenylamino, methoxyphenylamino, nitrophenylamino, 1-phenylethylamino, N-(methyl)-3-phenyl-2-propenylamino, benzotriazolylphenylmethyl, 2-pyridinylmethylamino, N-(ethyl)-2-pyridinylmethylamino, 2-thienylmethylamino, and furylmethylamino. Further examples of amino radicals include methylhydrazino, dimethylhydrazino, N-ethylanilino, and 2-methylanilino. The amine may also be substituted with diethyl N-ethylphosphoramidic acid, t-butoxycarbonyl, methoxycarbonyl, ethoxycarbonyl, propoxycarbonyl, etc. Of these examples of the amino radical, ethylamino is preferred.

Examples of B include, but are not limited to, trimethylsilyl, ethyldimethylsilyl, diethylmethylsilyl, triethylsilyl, dimethylpropylsilyl, dipropylmethylsilyl, dimethyl-1-(methyl)ethylsilyl, tripropylsilyl, butyldimethylsilyl, pentyldimethylsilyl, hexyldimethylsilyl, cyclopropyldimethylsilyl, cyclobutyldimethylsilyl, cyclopentyldimethylsilyl, cyclohexyldimethylsilyl, dimethylethenylsilyl, dimethylpropenylsilyl, chloromethyldimethylsilyl, 2-chloroethyldimethylsilyl, bromomethyldimethylsilyl, bicycloheptyldimethylsilyl, dimethylphenylsilyl, dimethyl-2-(methyl)phenylsilyl, dimethyl-2-fluorophenylsilyl, and other such silyl groups of the formula $Si(R_2)_3$; any such silyl group connected to the $Z_1$–$Z_2$ ring by a methylene group; and any of these groups wherein germanium or tin is substituted for silicon. Of these examples of B, trimethylsilyl is preferred.

Further examples of B include 1,1-dimethylethyl, 1,1-dimethylpropyl, 1,1-dimethylbutyl, 1,1-dimethylpentyl, 1-ethyl-1-methylbutyl, 2,2-dimethylpropyl, 2,2-dimethylbutyl, 1-methyl-1-ethylpropyl, 1,1-diethylpropyl, 1,1,2-trimethylpropyl, 1,1,2-trimethylbutyl, 1,1,2,2-tetramethylpropyl, 1,1-dimethyl-2-propenyl, 1,1,2-trimethyl-2-propenyl, 1,1-dimethyl-2-butenyl, 1,1-dimethyl-2-propynyl, 1,1-dimethyl-2-butynyl, 1-cyclopropyl-1-methylethyl, 1cyclobutyl-1-methylethyl, 1-cyclopentyl-1-methylethyl, 1-(1-cyclopentenyl)-1-methylethyl, 1-cyclohexyl-1-methylethyl, 1-(1-cyclohexenyl)-1-methylethyl, 1-methyl-1-phenylethyl, 1,1-dimethyl-2-chloroethyl, 1,1-dimethyl-3-chloropropyl, 1,1-dimethyl-2-methoxyethyl, 1,1-dimethyl-2-(methylamino)ethyl, 1,1-dimethyl-2-(dimethylamino)ethyl, 1,1-dimethyl-3-chloro-2-propenyl, 1-methyl-1-methoxyethyl, 1-methyl-1-(methylthio)ethyl, 1-methyl-1-(methylamino)ethyl, 1-methyl-1-(dimethylamino)ethyl, 1-chloro-1-methylethyl, 1-bromo-1-methylethyl, and 1-iodo-1-methylethyl. Of these examples of B, 1,1-dimethylethyl is preferred.

Further examples of B are 1,1-dimethylethylamino, 1,1-dimethylpropylamino, 1,1-dimethylbutylamino, 1,1-dimethylpentylamino, 1-ethyl-1-methylbutylamino, 2,2-dimethylpropylamino, 2,2-dimethylbutylamino, 1-methyl-1-ethylpropylamino, 1,1-diethylpropylamino, 1,1,2-trimethylpropylamino, 1,1,2-trimethylbutylamino, 1,1,2,2-tetramethylpropylamino, 1,1-dimethyl-2-propenylamino, 1,1,2-trimethyl-2-propenylamino, 1,1-dimethyl-2-butenylamino, 1,1-dimethyl-2-propynylamino, 1,1-dimethyl-2-butynylamino, 1-cyclopropyl-1-methylethylamino, 1-cyclobutyl-1-methylethylamino, 1-cyclopentyl-1-methylethylamino, 1-(1-cyclopentenyl)-1-methylethylamino, 1-cyclohexyl-1-methylethylamino, 1-(1-cyclohexenyl)-1-methylethylamino, 1-methyl-1-phenylethylamino, 1,1-dimethyl-2-chloroethylamino, 1,1-dimethyl-3-chloropropylamino, 1,1-dimethyl-2-methoxyethylamino, 1,1-dimethyl-2-(methylamino)ethylamino, 1,1-dimethyl-2-(dimethylamino)ethylamino, and 1,1-dimethyl-3-chloro-2-propenylamino. Any of these groups may also have a methyl substitution on the nitrogen, as in N-(methyl)-1,1-dimethylethylamino and N-(methyl)-1,1-dimethylpropylamino. Of these examples of B, 1,1-dimethylethylamino and N-(methyl)-1,1-dimethylethylamino are preferred.

Further examples of B include 1,1-dimethylethoxy, 1,1-dimethylpropoxy, 1,1-dimethylbutoxy, 1,1-dimethylpentoxy, 1-ethyl-1-methylbutoxy, 2,2-dimethylpropoxy, 2,2-dimethylbutoxy, 1-methyl-1-ethylpropoxy, 1,1-diethylpropoxy, 1,1,2-trimethylpropoxy, 1,1,2-trimethylbutoxy, 1,1,2,2-tetramethylpropoxy, 1,1-dimethyl-2-propenoxy, 1,1,2-trimethyl-2-propenoxy, 1,1-dimethyl-2-butenoxy, 1,1-dimethyl-2-propynyloxy, 1,1-dimethyl-2-butynyloxy, 1-cyclopropyl-1-methylethoxy, 1-cyclobutyl-1-methylethoxy, 1-cyclopentyl-1-methylethoxy, 1-(1-cyclopentenyl)-1-methylethoxy, 1-cyclohexyl-1-methylethoxy, 1-(1cyclohexenyl)-1-methylethoxy, 1-methyl-1-phenylethoxy, 1,1-dimethyl-2-chloroethoxy, 1,1-dimethyl-3-chloropropoxy, 1,1-dimethyl-2-methoxyethoxy, 1,1-dimethyl-2-(methylamino)ethoxy, 1,1-dimethyl-2-(dimethylamino)ethoxy, 1,1-dimethyl-3-chloro-2-propenoxy. Of these examples of B, 1,1-dimethylethoxy is preferred.

Further examples of B include 1-methylcyclopropyl, 1-methylcyclobutyl, 1-methylcyclopentyl, 1-methylcyclohexyl, 1-methylcyclopropylamino, 1-methylcyclobutylamino, 1-methylcyclopentylamino, 1-methylcyclohexylamino, N-(methyl)-1-methylcyclopropylamino, N-(methyl)-1-methylcyclobutylamino, N-(methyl)-1-methylcyclopentylamino, and N-(methyl)-1-methylcyclohexylamino.

$R_n$ may be any substituent(s) which do(es) not unduly reduce the effectiveness of the compounds to function in the method of disease control. $R_n$ is generally a small group; "n" is preferably 1 for benzene rings and 2 for furan and thiophene. R is more preferably methyl or halogen, and more preferably is located adjacent to A.

The present invention also provides novel compounds of the formula given above. However, when $Z_1$ and $Z_2$ are part of a benzene ring, the following are not included as novel compounds: 1) n is not zero when B is trimethylsilyl and A is N,N-diethylaminocarbonyl, N,N-bis(1-methylethyl)aminocarbonyl, N-methylaminothiocarbonyl, N-ethylaminocarbonyl, 1-piperidinylcarbonyl, or N-phenylaminocarbonyl; or when B is orthotolyl and A is N,N-diethylaminocarbonyl, N,N-bis(1-methylethyl)aminocarbonyl, N-methylaminocarbonyl, or O-methylcarbamyl; or when B is 1,1-dimethylethyl and A is N,N-dimethylaminothiocarbonyl or N-phenylaminocarbonyl; or when B is trimethylstannyl and A is N,N-diethylaminocarbonyl or O-(1,1-dimethylethyl)carbamyl; 2) when B is 2-trimethylsilyl and A is N,N-diethylaminocarbonyl, $R_n$ is not 3-fluoro-6-formyl, 3-fluoro-6-methyl, 3-chloro-6-formyl, 3-fluoro, 3-chloro, 3-chloro-6-methyl, 6-trimethylsilyl, or 6-methyl; 3) when A is O-(1,1-dimethylethyl)carbamyl and B is 2-trimethylsilyl, $R_n$ is not 5-trifluoromethyl; 4) when A is N-phenylaminocarbonyl and B is 2,2-dimethylpropyl, $R_n$ is not 3-methyl; and 5) R is not isothiocyanato when A is —C(O)-amine and $W_m$ is —O—.

When $Z_1$ and $Z_2$ are part of a thiophene, furan or pyrrole ring, the novel compounds of the present invention do not include B equal to trimethylsilyl when A is (diethylamino)carbonyl.

The invention also provides fungicidal compositions useful in said method.

As used herein, the term "alkyl", unless otherwise indicated, means an alkyl radical, straight or branched chain, having, unless otherwise indicated, from 1 to 10 carbon atoms. The terms "alkenyl" and "alkynyl" mean unsaturated radicals having from 2 to 7 carbon atoms. Examples of such alkenyl groups include ethenyl, 1-propenyl, 2-propenyl, 1-butenyl, 2-butenyl, 3-butenyl, 2-methyl-1-propenyl, 2-methyl-2-propenyl, 1-methylethenyl, and the like. Examples of such alkynyl groups include ethynyl, 1-propynyl, 2-propynyl, 1,1-dimethyl-2-propynyl, and so forth. Substituent groups may also be both alkenyl and alkynyl, for example, 6,6-dimethyl-2-hepten-4-ynyl.

As used herein, the term "alkoxy" means an alkyl group having, unless otherwise indicated, from 1 to 10 carbon atoms connected via an ether linkage. Examples of such alkoxy groups include methoxy, ethoxy, propoxy, 1-methylethoxy, and so forth.

As used herein, the term "alkoxyalkyl" means an ether radical having, unless otherwise indicated, from 1 to 10 carbon atoms. Examples of such alkoxyalkyl groups include methoxymethyl, methoxyethyl, ethoxymethyl, ethoxyethyl, and so forth.

As used herein, the terms "monoalkylamino" and "dialkylamino" each mean an amino group having, respectively, 1 or 2 hydrogens replaced with an alkyl group.

As used herein, the term "haloalkyl" means an alkyl radical having one or more hydrogen atoms replaced by halogens, including radicals having all hydrogen atoms substituted by halogen. Examples of such haloalkyl groups are fluoromethyl, difluoromethyl, trifluoromethyl, chloromethyl, trichloromethyl, and so forth.

As used herein, the term "halo" means a radical selected from chloro, bromo, fluoro, and iodo.

DETAILED DESCRIPTION OF THE INVENTION

Control of Gg diseases, including Take-All, using a chemical control agent may be accomplished in several ways. The agent may be applied directly to soil infested with Gg, for example, at the time of planting along with the seed. Alternatively, it may applied after planting and germination. Preferably, however, it is applied to the seed in a coating prior to planting. This technique is commonly used in many crops to provide fungicides for control of various phytopathological fungi.

Compositions of the present invention are comprised of a fungicidally effective amount of one or more of the compounds described above and one or more adjuvants. The active ingredient may be present in such compositions at levels from 0.01 to 95 percent by weight. Other fungicides may also be included to provide a broader spectrum of fungal control. The choice of fungicides will depend on the crop and the diseases known to be a threat to that crop in the location of interest.

The fungicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate. Stabilizers may also be used to produce stable emulsions, such as magnesium aluminum silicate and xanthan gum.

Other formulations include dust concentrates comprising from 0.1 to 60% by weight of the active ingredient on a suitable extender, optionally including other adjuvants to improve handling properties, e.g., graphite. These dusts may be diluted for application at concentrations within the range of from about 0.1–10% by weight.

Concentrates may also be aqueous emulsions, prepared by stirring a nonaqueous solution of a water-insoluble active ingredient and an emulsification agent with water until uniform and then homogenizing to give stable emulsion of very finely-divided particles. Or they may be aqueous suspensions, prepared by milling a mixture of a water-insoluble active ingredient and wetting agents to give a suspension, characterized by its extremely small particle size, so that when diluted, coverage is very uniform. Suitable concentrations of these formulations contain from about 0.1–60% preferably 5–50% by weight of active ingredient.

Concentrates may be solutions of active ingredient in suitable solvents together with a surface active agent. Suitable solvents for the active ingredients of this invention for use in seed treatment include propylene glycol, furfuryl alcohol, other alcohols or glycols, and other solvents which do not substantially interfere with seed germination. If the active ingredient is to be applied to the soil, then solvents such as N,N-dimethylformamide, dimethylsulfoxide, N-methylpyrrolidone, hydrocarbons, and water-immiscible ethers, esters, or ketones.

The concentrate compositions herein generally contain from about 1.0 to 95 parts (preferably 5–60 parts) active ingredient, about 0.25 to 50 parts (preferably 1–25 parts) surface active agent and where required about 4 to 94 parts solvent, all parts being by weight based on the total weight of the concentrate.

For application to the soil at the time of planting, a granular formulation may be used. Granules are physically stable particulate compositions comprising at least one active ingredient adhered to or distributed through a basic matrix of an inert, finely-divided particulate extender. In order to aid leaching of the active ingredient from the particulate, a surface active agent such as those listed hereinbefore, or for example, propylene glycol, can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the fungicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The method of the present invention may be carried out by mixing the composition comprising the active ingredient into the seed prior to planting at rates from 0.01 to 50 g per kg of seed, preferably from 0.1 to 5 g per kg, and more preferably from 0.2 to 2 g per kg. If application to the soil is desired, the compounds may be applied at rates from 10 to 1000 g per hectare, preferably from 50 to 500 g per hectare. The higher application rates will be needed for situations of light soils or greater rainfall or both.

The compounds useful in the present invention may be prepared by methods known to those of ordinary skill in the art. The following examples illustrate some of these methods and are illustrative only; they are not meant to be limiting in any way.

Unless otherwise indicated, percentages are given as weight/weight. Melting points and boiling points are reported uncorrected. Thin layer chromatography was carried out with varying concentrations of ethyl acetate/hexanes elutions. Tetrahydrofuran and ether solvents were distilled from sodium metal/benzophenone immediately prior to use. N,N,N',N'-(Tetramethyl)ethylenediamine was distilled from calcium hydride prior to use. All other reagents were purchased from Aldrich or Lancaster and used without purification. A measured physical property is reported for each example or the elemental analysis is given at the end of the examples.

The following abbreviations have the meanings shown:

| | |
|---|---|
| n-BuLi | n-Butyl lithium |
| s-BuLi | sec-Butyl lithium |
| t-BuLi | tert-Butyl lithium |
| DAST | Diethylaminosulfur trifluoride |
| DEAD | Diethyl azodicarboxylate |
| DMF | Dimethylformamide |
| DMSO | Dimethylsulfoxide |
| TMSCl | Trimethylsilyl chloride |
| THF | Tetrahydrofuran |
| TMEDA | N,N,N',N'-(tetramethyl)ethylenediamine |
| eq | equivalent(s) |
| aq | aqueous |
| sat | saturated |
| min | minutes |
| h | hours |
| MeI | Methyl iodide |
| Lawesson's Reagent | [2,4-bis(4-methoxyphenyl)-1,3-dithia-2,4-diphosphetane-2,4-disulfide] |
| TLC | Thin Layer Chromatography |
| HPLC | High Pressure Liquid Chromatography |
| RC | Radial Chromatography |
| GLC | Gas-liquid Chromatography |
| RT | room temperature |
| m.p. | melting point |

GENERAL METHODS

The phrase "worked up in the usual manner" refers to treatment of the reaction mixture with 10% aq citric acid, extraction with diethyl ether, washing of the combined organic extracts with sat brine solution, drying of the organic extract over $MgSO_4$, and evaporation to dryness in vacuo to afford the crude product. The phrase "appropriate" means a compound having the substituents desired for the final product of the reaction.

Method A. Ortho-introduction of Electrophiles into N,N-dialkylbenzamides 1.3M s-BuLi in cyclohexane (1.1 to 1.2 molar eq) was added dropwise to a dry-ice/acetone or an ether/liquid nitrogen cooled 1.0M solution of TMEDA (1.0 to 1.2 molar eq) in THF, followed by the dropwise addition of the appropriate N,N-dialkylbenzamide (1.0 eq) in THF. The resulting reaction mixture was stirred for 30–60 min at −78° C. to ensure complete aryl anion formation, then was cooled to ≦−90° C. with an ether/liquid nitrogen bath and quenched by the careful addition of the appropriate electrophile. The reaction was allowed to warm slowly to 0° C. then was worked up in the usual manner. If needed, the crude product was purified by chromatography, recrystallization or distillation.

Method B. Ortho-introduction of Electrophiles into N,N-dialkylbenzamides via Inverse Addition 1.3M s-BuLi in cyclohexane (1.2 eq) was added dropwise to an ether/liquid nitrogen cooled 1.0M solution of TMEDA (1.2 eq) in THF, followed by the dropwise addition of the appropriate N,N-dialkylbenzamide (1.0 eq) in THF. The internal reaction temperature was maintained between −80 and −95° C. during both additions. After addition, the cooling bath was replaced with dry-ice/acetone, and the resulting reaction was stirred at −78° C. for 1 h. This solution was then cannulaed into a solution of an excess of the appropriate electrophile in THF at a rate which maintained the internal reaction temperature below −80° C. with an ether/liquid nitrogen bath. The resulting reaction mixture was slowly allowed to 0° C. then purified in the manner described below for each compound.

Method C. Ortho-introduction of Electrophiles into N-alkylbenzamides 1.3M s-BuLi in cyclohexane (2.1 to 2.2 eq) was added dropwise to a dry-ice/acetone or an ether/liquid nitrogen cooled 1.0M solution of TMEDA (1.0 to 1.2 eq) in THF, followed by the dropwise addition of the appropriate N-alkylbenzamide (1.0 eq) in THF. The resulting reaction mixture was stirred for 30–60 min at −78° C. to ensure complete aryl anion formation, then was cooled to <−90° C. with an ether/liquid nitrogen bath and quenched by the careful addition of the appropriate electrophile. The reaction was allowed to warm slowly to −30° C. then was worked up in the usual manner. If needed, the crude product was purified by chromatography, recrystallization or distillation.

METHOD D. Boronate Coupling Procedure

The compound of Example f (5.0 g, 27.2 mmol), TMEDA (6.6 g, 57.1 mmol), and THF (100 Ml) were stirred at −78° C. under nitrogen, and 1.3M s-BuLi in cyclohexane (44 mL, 57.1 mmol) was added dropwise. The mixture was stirred for 15 min and trimethylborate (3.1 g, 29.9 mmol) was added all at once. The mixture was then stirred at −78° C. for 30 min before warming to RT. It was then poured into 10% HCl (100 mL). This mixture was made basic with sat aq $NaHCO_3$ and extracted with ether. The aq layer was reacidified and extracted with $CH_2Cl_2$. The combined organic layers were dried ($MgSO_4$), concentrated, and recrystallized to yield 4.2 g 4-chloro-2-ethyl- 1-hydroxy-1H-2,1-benzazaborol-3(2H)-one as a white solid. m.p. 210–211° C.

This compound (1.05 eq) in ethanol (2 mL) is added to an appropriate aryl, benzyl, or vinyl bromide (1 eq) and catalytic tetrakis(triphenylphosphine)palladium(O) in toluene (20 mL) at RT under nitrogen. Sodium carbonate (4 mL of a 2M aq solution) was then added and the resulting mixture was heated to reflux (4–24 h) and monitored by TLC. The mixture was then cooled to room temperature, diluted with additional toluene (20 mL), filtered through celite/silica, washed with water, dried ($MgSO_4$), and concentrated. If needed, the crude product was purified by chromatography or recrystallization from ethyl acetate/hexanes.

METHOD E1. Amination of Benzoyl Chlorides

A solution of the appropriate acid chloride (1 eq) in toluene or $CH_2Cl_2$ was added dropwise to an ice-water cooled solution of the appropriate amine ($\geqq 2$ eq) in the same solvent. The mixture was stirred at RT for 1–16 h until complete by GLC, then was partitioned between ethyl acetate and dilute aq acid. The organic phase was dried ($MgSO_4$) and concentrated. If needed, the crude product was purified by chromatography, recrystallization or distillation.

METHOD E2. Amination of Benzoyl Chlorides

To a solution of the appropriate amine (>1 eq) in 50 mL $CH_2Cl_2$ is added an appropriate benzoyl chloride (1 eq) and a catalytic amount of benzyltriethylammonium chloride or pyridine. The mixture is cooled to 5° C. and $\geqq 1$ eq NaOH (50% aq) is added. The mixture is stirred from 3–16 h, washed with 10% HCl and water, dried and concentrated. The crude product is purified by chromatography, recrystallization or distillation to afford pure product.

STARTING MATERIALS

Example a. 2-Chloro-6-(trimethylsilyl)benzoic acid

2-Chlorobenzoic acid (3.91 g, 25 mmol), THF (60 mL), and TMEDA (8.6 mL, 57 mmol) were stirred under nitrogen and cooled to −100° C. 1.3M s-BuLi in cyclohexane (0.055 mol, 42.3 mL) was added dropwise keeping the temperature below −80° C. After the addition was complete, TMSCl (2.7 g, 25 mmol) was added dropwise and the resulting mixture was allowed to stir and slowly warm to −30° C. 25% citric acid (100 mL) was added and the mixture was extracted with two 50 mL portions of ether, which were then combined and washed three times with water, dried ($MgSO_4$) and concentrated. The crude product was purified by HPLC, eluting with 2:3 ethyl acetate/hexanes. The product was recovered as a white solid in 63% yield. m.p. 129–131° C.

Example b. 2-Chloro-6-(trimethylsilyl)benzoyl chloride

The compound of Example a (2.4 g, 0.01 mol), thionyl chloride (3.57 g, 0.03 mol), toluene (50 mL), and 1 drop of DMF were stirred at RT overnight. The reaction mixture was twice concentrated under vacuum from toluene (50 mL) to afford the desired product as a brown oil in 100% yield.

Example c. 2-Bromo-6-(trimethylsilyl)benzoic acid

2-Bromobenzoic acid (30.15 g, 150 mmol), THF (400 mL), and diisopropyl amine (33.4 g, 330 mmol) were stirred under nitrogen and cooled to −78° C. 10M n-BuLi in hexanes (31 mL, 0.31 mol) was then added dropwise, followed by the dropwise addition of TMSCl (17.4 g, 160 mmol). The mixture was allowed to slowly warm to −30° C., stirred for 1 h, then was poured into 25% citric acid (100 mL) and stirred for 15 min. The mixture was extracted with two 100 mL portions of ether, which were combined and washed three times with sat aq $NaHCO_3$ solution. The bicarbonate solution was acidified with 25% citric acid and extracted with three 100 mL portions of ether. These extracts were combined, dried (MgSO4), and concentrated. The crude product was purified by recrystallization from ether/hexanes, and the desired product was recovered as a white solid in 35% yield. m.p. 139–141° C.

Example d. 2-Bromo-6-(trimethylsilyl)benzoyl chloride

The title compound was prepared from the compound of Example c according to the procedure of Example b.

Example e. N,N-Diethyl-2-chlorobenzamide

2-Chlorobenzoyl chloride is reacted with diethylamine using General Method E1 or E2 to produce the title compound.

Example f. N-Ethyl-2-chlorobenzamide

2-Chlorobenzoyl chloride is reacted with ethyl amine using General Method E1 or E2, to produce the title compound.

Example g. (2-(2,6-difluorophenyl)-4,4-dimethyl-2-oxazoline

A solution of 2,6-difluorobenzoyl chloride (50 g, 283 mmol) in $CH_2Cl_2$ (200 mL) was added rapidly dropwise to an ice water-cooled solution of 2-amino-2-methyl-1-propanol (63.1 g, 708 mmol) in $CH_2Cl_2$ (400 mL). The resulting mixture was stirred at RT and monitored to completion by GLC, then was extracted twice with 10% HCl and once with sat aq $NaHCO_3$. The organic phase was dried ($MgSO_4$), and concentrated to afford 61.9 g N-(1,1-dimethyl-2-hydroxyethyl)-2,6-difluorobenzamide as a white solid.

This compound (60 g, 283 mmol) was added portionwise to ice water-cooled thionyl chloride (65 mL). The resulting yellow solution was stirred at RT for 1 h, then was poured into stirred ether. The solid was collected and washed with ether, then was partitioned between dilute aq NaOH and ether. This latter ether extract was dried ($MgSO_4$) and concentrated to afford 52.39 g of the title compound as a white solid, an 88% yield.

Example h. 2-Chloro-6-(trimethylsilyl)phenyl isocyanate

The compound of Example b (5.0 mmol) was dissolved in 50 mL acetonitrile and tetrabutylammonium azide ($BU_4N_3$) (5.2 mmol) was added. The mixture was stirred at RT for 0.5 h. The solvent was removed and the resulting oil was dissolved in 100 mL toluene. After addition of 100 mL hexane a precipitate was filtered off; the filtrate was concentrated to yield 1.5 g of the title compound.

Example i. 2-Chloro-6-(trimethylsilyl)benzaldehyde

A 2.0M solution of borane-dimethylsulfide in THF (100 mL) was added over 15 min to a solution of the compound of Example a (11.4 g, 0.05 mol) THF (200 mL). The mixture was refluxed for two days, quenched with methanol (500 mL), and allowed to stand at RT for 2 days. The solvent was then removed and 2-chloro-α-hydroxy-6-(trimethylsilyl) toluene was recrystallized from hexane as 8.9 g of crystals, an 83% yield. m.p. 40–42° C.

This compound (6.4 g, 29.9 mmol) was added to a solution of pyridium chlorochromate (7.5 g) in $CH_2Cl_2$ (500 mL). The mixture was stirred over 2 days and ether (500 mL) was added. The mixture was filtered through silica gel and the solvent removed under vacuum. Again ether (200 mL) was added and the mixture filtered through silica gel. The solvent was removed to yield the title compound as 6.2 g of an oil, a 98% yield.

Example j. 2-(2,6-difluorophenyl)-2-oxazoline 2,6-Difluorobenzoyl chloride (100 g, 566 mmol) was added dropwise over 2 h to a vigorously stirred and ice water cooled mixture of 2-bromoethyl amine hydrobromide (116.05 g, 566 mmol), benzyltriethylammonium chloride (5 g, 22.0 mmol), 10% aq NaOH (680 mL, 1.7 mol), and $CH_2Cl_2$ (1.5 L). The resulting mixture was stirred at RT overnight, than was washed with water (3×200 mL), dried ($MgSO_4$), concentrated, and kugelrohr distilled to afford 51.8 g of 2-(2,6-difluorophenyl)-2-oxazoline as a colorless oil, a 50% yield.

Example k. N-ethyl t-butylmethyleneimine

70% $EtNH_2$ (20.0 g, 310 mmol) was carefully added to trimethylacetaldehyde (24.35 g, 283 mmol) with ice-water cooling to control the exotherm. When the exotherm ceased, the organic layer was separated and reacted with an additional 70% $EtNH_2$ (1–2 g). The organic layer was separated and distilled (b.p. 96–98° C.) from $CaH_2$ to afford 28.3 g of N-ethyl t-butylmethyleneimine as a colorless oil, an 88% yield.

EXAMPLES 1–4

These compounds are prepared as reported by Mills, et al., in "Directed Ortho Metalation of N,N-Diethylbenzamides. Silicon Protection of Ortho Sites and the o-Methyl Group," *J. of Organic Chemistry* 54: 4372–4385, 1989.

| Ex. No. | Compound |
|---|---|
| 1 | N,N-Diethyl-3-fluoro-6-methyl-2-(trimethylsilyl)benzamide |
| 2 | N,N-Diethyl-2-(trimethylsilyl)benzamide |
| 3 | N,N-Diethyl-2-methyl-6-(trimethylsilyl)benzamide |
| 4 | N,N-Diethyl-3-fluoro-2-(trimethylsilyl)benzamide |

EXAMPLE 5

N-(1,1-Dimethylethyl)-3-fluoro-N-methyl-2-(trimethylsilyl)benzamide

3-Fluorobenzoyl chloride was reacted with N-methyl-N-tert-butylamine using General Method E1 or E2 to produce N-methyl-N-(tert-butyl)-3-fluorobenzamide. This compound was used in General Method A to prepare the title compound. Kugelrohr distillation afforded 12.07 g of analytically pure desired material. m.p. 32–35° C.

EXAMPLE 6

2-(1,1-Dimethylethyl)-N,N-diethyl-6-methylbenzamide

A 1.7M solution of t-BuLi in pentane (161 mL, 274 mmol) was added dropwise to a solution of 2-(2-fluorophenyl)-4,4-dimethyl-2-oxazoline [cf. Meyers A. I. and Williams B. E., *Tetrahedron Letters,* 223–226(1978)] (48.0 g., 249 mmol) in THF (320 mL), maintaining the reaction temperature between −45 and −40° C. with a dry-ice/acetone cooling bath. The resulting reaction mixture was maintained at ≦−40° C. with a dry-ice/acetonitrile bath, and monitored to completion by GLC over 20 min. This mixture was poured onto ice and extracted three times with ether. These extracts were combined, dried ($MgSO_4$), concentrated and distilled under vacuum to afford 56.87 g of 2-(2-tert-butylphenyl)-4,4-dimethyl-2-oxazoline, a 93% yield.

A 2M solution of trifluoromethanesulfonic anhydride (1 eq) in $CH_2Cl_2$ was added dropwise to an ice water-cooled 0.67M solution of 2-(2-tert-butylphenyl)-4,4-dimethyl-2-oxazoline (1 eq) in $CH_2Cl_2$. The resulting solution was stirred at 0° C. for 10 min, then poured into an equal volume of ice water and vigorously stirred for 15 min. The $CH_2Cl_2$ layer was washed twice with 10% HCl, dried ($MgSO_4$), and concentrated to afford 15.59 g of N-[2-(2-tert-butylphenylcarboxy)-1,1-dimethylethyl]-trifluoromethanesulfonamide as a white solid without any further purification, a 95% yield. m.p. 69–71° C.

A freshly prepared solution of diazomethane in anhydrous ether was added in excess to a solution of N-[2-(2-tert-butylphenylcarboxy)-1,1-dimethylethyl]-trifluoromethanesulfonamide (13.1 g) in ether. The resulting yellow solution was allowed to stand at RT overnight, then was washed with 10% HCl followed by 2.5N aq NaOH. The organic solution was dried ($MgSO_4$), and concentrated to afford 13.0 g of pure N-methyl-N-[2-(2-tert-butylphenylcarboxy)-1,1-dimethylethyl]-trifluoromethanesulfonamide as a white solid, a 96% yield. m.p. 42–44° C.

N-methyl-N-[2-(2-tert-butylphenylcarboxy)-1,1-dimethylethyl]trifluoromethanesulfonamide (1 eq) was saponified in a 2.0M solution of KOH (3 eq) in DMSO at 110° C. for 4 h. The resulting solution was cooled, diluted with water, and extracted twice with ether. These ether extracts were discarded. The aqueous phase was then acidified to pH 1 with conc HCl and extracted twice with ether. These latter ether extracts were dried ($MgSO_4$), and concentrated to afford 4.47 g of 2-tert-butylbenzoic acid as pure white solid without any further purification, a 96% yield. m.p. 58–60° C.

A solution of 2-tert-butylbenzoic acid (4.0 g, 22.5 mmol) in thionyl chloride (8.2 mL, 112 mmol) was stirred at RT for 2 h, then was concentrated three times from carbon tetrachloride to remove all traces of excess thionyl chloride. A solution of diethylamine (4.93 g, 67.4 mmol) in $CH_2Cl_2$ (10 mL) was added dropwise over 10 min to an ice water-cooled solution of the crude acid chloride in $CH_2Cl_2$ (35 mL). Ten min after addition was complete, the reaction was partitioned between ether and 10% HCl. The ether phase was then washed with sat aq $NaHCO_3$, then was dried ($MgSO_4$), and concentrated to afford a quantitative yield of N,N-diethyl-2-tert-butylbenzamide as an off-white solid. m.p. 38.5–40.5° C.

N,N-diethyl-2-tert-butylbenzamide (1.00 g, 4.3 mmol) was used in General Method A to afford 1.05 g of the title compound as a yellow oil, a 99% yield.

EXAMPLE 7

2-Chloro-N,N-diethyl-6-(trimethylstannyl)benzamide 1.3M s-BuLi in cyclohexane (4.8 mL, 6.2 mmol) was added dropwise to a −78° C. cooled solution of the compound of Example e (1.0 g, 4.7 mmol) and TMEDA (930 μL, 6.2 mmol) in THF (15 mL). The resulting yellow mixture was stirred at −78° C. for 45 min, then was quenched by the dropwise addition of trimethyltin chloride (1.41 g, 7.1 mmol) in THF (5 mL), maintaining the internal reaction temperature ≦−65° C. The resulting green solution was warmed to RT to afford a yellow solution which was diluted with ether and extracted twice with aq 10% HCl, and once with sat aq NaHCO$_3$. The ether solution was dried (MgSO$_4$), concentrated, and purified by HPLC with 1:4 ethyl acetate/ hexanes to afford 1.37 g of the title compound, an 81% yield, as a colorless oil.

EXAMPLE 8

2-(1,1-Dimethylethyl)-N-ethyl-6-methylbenzamide

A solution of 2-tert-butyl-6-methylaniline (1 eq) and 97% formic acid (4 eq) was refluxed for 16 h, then was concentrated under vacuum and recrystallized from methanol/water to afford 2-tert-butyl-6-methylformanilide.

Phosphorus oxychloride (0.67 eq) was added to an ice water-cooled, stirred slurry of this compound (1 eq) in a mixture of pyridine (11 eq=1 volume) and pentane (0.5 volume). The resulting mixture was briefly warmed to about 40° C. for 10 min, then the mixture was cooled. Ice water (0.5 volume) was carefully added and the two layers were separated. The aq layer was extracted with pentane (0.25 volume), then the combined organic solutions were washed three times with water (0.5 volume), dried (MgSO$_4$), and concentrated to afford 2-tert-butyl-6-methylphenyl isocyanide.

This compound was heated at 250–253° C. for 6 h to complete the rearrangement as evidence by infrared analysis. Recrystallization from hexanes afforded pure 2-tert-butyl-6-methylbenzonitrile. m.p. 60–62° C.

A solution of this compound (500 mg, 2.9 mmol) and 1.0M triethyloxonium tetrafluoroborate in CH$_2$Cl$_2$ (5.8 mL, 5.8 mmol) was stirred at RT for several days under an atmosphere of nitrogen. The reaction was diluted with CH$_2$Cl$_2$ and extracted with sat aq NaHCO$_3$, then was dried (MgSO$_4$), concentrated, and purified by HPLC with 1:4 ethyl acetate/hexanes to afford 430 mg of title compound as a white solid, a 68% yield. m.p. 110.5–111.5° C.

EXAMPLE 9

2-[(1,1-Dimethylethyl)dimethylsilyl]-N,N-diethyl-3-fluorobenzamide 1.3M s-BuLi in cyclohexane (7.7 mL, 0.01 mol) was added dropwise to THF (30 mL) and TMEDA (1.28 g, 0.011 mol) cooled to −78° C. under nitrogen with stirring. To this mixture was added 0.0097 mol of N,N-diethyl-3-fluorobenzamide (prepared from 3-fluorobenzoic acid and diethylamine according to the procedures of the examples of b and f) dissolved in a minimum amount of THF dropwise. The mixture was stirred for 10 min and injected with t-butyldimethylsilylchloride (3.01 g, 0.02 mol). The reaction mixture was stirred and warmed to RT overnight. 25% citric acid (15 mL) was added and the mixture was extracted three times with ether. The ether extracts were combined and washed twice with water, dried (MgSO$_4$), concentrated, and purified by RC eluting with 7:15 ethyl acetate/hexanes. The title compound was recovered as a tan solid in 81% yield. m.p. 50–51° C.

EXAMPLE 10

2-[(1,1-Dimethylethyl)dimethylsilyl]-N,N-diethyl-3-fluoro-6-methylbenzamide 1.3M s-BuLi in cyclohexane (1.8 mL, 2.3 mmol) was added dropwise with stirring to THF (20 mL) and TMEDA (0.32 g, 2.76 mmol), cooled to −78° C. under nitrogen. To this mixture was added dropwise the compound of Example 9 (0.6 g, 2 mmol), dissolved in a minimum amount of THF. After stirring for 10 min, MeI (0.98 g, 6.9 mmol) was injected. The mixture was stirred for 1 h; 15 mL of 25% citric acid was added and the mixture extracted with ether 3 times. The ether extracts were combined and washed twice with water, dried (MgSO$_4$), and concentrated. The crude product was purified by RC, eluting with 3:7 ethyl acetate/ hexanes. The title compound was obtained as a light yellow oil in a 31% yield.

EXAMPLE 11

N-(1,1-Dimethylethyl)-3-fluoro-N,6-dimethyl-2-(trimethylsilyl)benzamide 1.3M s-BuLi in cyclohexane (31.4 mL, 41 mmol) was added dropwise to THF (100 mL) and TMEDA (5.35 g, 46 mmol), cooled to −100° C. under nitrogen with stirring. To this mixture was added dropwise the compound of Example 5 (10.45 g, 37 mmol), dissolved in a minimum amount of THF. After stirring for 10 min, MeI (15.8 g, 0.1114 mol) was injected. The mixture was stirred for 1 h and 25% citric acid (15 mL) was added. The mixture was extracted three times with ether; the ether extracts were combined and washed twice with water, dried (MgSO$_4$), and concentrated. The crude product was purified by RC, with 1:9 ethyl acetate/ hexanes. The title compound was recovered as a light yellow solid, in 99% yield. m.p. 44–47° C.

EXAMPLE 12

N-Ethyl-3-fluoro-2-(trimethylsilyl)benzamide

N-ethyl-3-fluorobenzamide (4.18 g, 0.025 mol) (prepared from 3-fluorobenzoic acid using the procedures of Examples b, and f), dissolved in a minimum amount of THF, was used in General Method C and purified by HPLC, eluting with 3:7 ethyl acetate/hexanes. The title compound was recovered as a white solid in 53% yield. m.p. 80–82° C.

EXAMPLE 13

N,N-Dipropyl-2-(trimethylsilyl)benzamide

N,N-(dipropyl)benzamide (4.0 g, 0.0195 mol) (prepared from benzoyl chloride and dipropyl amine using General Method E1 or E2) was used in General Method A to produce the desired compound which was purified by HPLC, eluting with 1:9 ethyl acetate/hexanes and recovered as a light yellow oil in 65% yield. $n_D^{25}$=1.5094.

EXAMPLE 14

2-Methyl-N,N-dipropyl-6-(trimethylsilyl)benzamide

The compound of Example 13 was reacted with MeI using General Method A to prepare the title compound.

EXAMPLE 15

3-Chloro-N,N-diethyl-2-(trimethylsilyl)benzamide

N,N-diethyl-3-chlorobenzamide (10.45 g, 50 mmol) (prepared from 3-chlorobenzoic acid and diethylamine using the procedures described above) was reacted with TMSCl (16.30 g, 150 mmol) using General Method A to afford 13.4 g of the title compound as an orange oil in 95% yield.

EXAMPLES 16–36

The following compounds were made by reaction of the compound of Example b with the appropriate amine using the procedures of General Method E1 or E2, or similar procedures. The melting points of those which are solids at ambient temperatures are reported as ° C.

| Example No. | Compound Name | Physical Property |
|---|---|---|
| 16 | 2-Chloro-N-phenyl-6-(trimethylsilyl)-benzamide | 158–160 |
| 17 | 2-Chloro-N-octyl-6-(trimethylsilyl)-benzamide | 94–96 |
| 18 | 2-Chloro-N-ethyl-N-(1-methylethyl)-6-(trimethylsilyl)benzamide | — |
| 19 | 2-Chloro-N-methyl-6-(trimethylsilyl)-benzamide | 125–127 |
| 20 | N-Butyl-2-chloro-6-(trimethylsilyl)-benzamide | 107–110 |
| 21 | 2-Chloro-N-(1-methylethyl)-6-(trimethylsilyl)benzamide | 140–143 |
| 22 | 2-Chloro-N-ethyl-N-methyl-6-(trimethylsilyl)benzamide | — |
| 23 | 2-Chloro-N-(1,1-dimethylethyl)-N-methyl-6-(trimethylsilyl)benzamide | — |
| 24 | 2-Chloro-N-ethyl-N-phenyl-6-(trimethylsilyl)benzamide | 95–98 |
| 25 | 2-Chloro-N-(2,2,2-trifluoro-ethyl)-6-(trimethylsilyl)-benzamide | 105–107 |
| 26 | 2-Chloro-N-propyl-6-(trimethylsilyl)benzamide | 108–109 |
| 27 | 2-Chloro-N-(2-hydroxyethyl)-6-(trimethylsilyl)benzamide | 138–140 |
| 28 | 2-Chloro-N-(1-methylpropyl)-6-(trimethylsilyl)benzamide | 144–145 |
| 29 | 2-Chloro-N-(2-chloroethyl)-6-(trimethylsilyl)benzamide | 111.5–113 |
| 30 | 2-Chloro-N-(3-chloropropyl)-6-(trimethylsilyl)benzamide | 128–131 |
| 31 | 2-Chloro-N-(phenylmethyl)-6-(trimethylsilyl)benzamide | 112–114 |
| 32 | 2-Chloro-N-(2-furylmethyl)-6-(trimethylsilyl)benzamide | 113–115 |
| 33 | 2-Chloro-N-(2-methylphenyl)-6-(trimethylsilyl)benzamide | 116.5–118 |
| 34 | 2-Chloro-N-cyclopropyl-6-(trimethylsilyl)benzamide | 101–104 |
| 35 | 2-Chloro-N-ethyl-N-(phenylmethyl)-6-(trimethylsilyl)benzamide | — |
| 36 | 2-Chloro-N,N-dipropyl-6-(trimethylsilyl)benzamide | — |

EXAMPLES 37–39

The following compounds were prepared using General Method A or B. The starting materials are N,N-diethyl-3-fluorobenzamide, which is prepared from 3-fluorobenzoic acid as generally described above, and an appropriate electrophile.

| Example No. | Compound Name | M.P. |
|---|---|---|
| 37 | 6-Bromo-N,N-diethyl-3-fluoro-2-(trimethylsilyl)benzamide | 53.0–54.0 |
| 38 | 6-Chloro-N,N-diethyl-3-fluoro-2-(trimethylsilyl)benzamide | |
| 39 | 2-Chloro-N,N-diethyl-6-(trimethylsilyl)benzamide | |

EXAMPLE 40

N,N-Diethyl-3-fluoro-6-iodo-2-(trimethylsilyl) benzamide 4.99 g of the compound of Example 4 and 20.3 g iodine were combined according to General Method B. The resulting reaction mixture was poured into ice water. $CH_2Cl_2$ was added, and the mixture was extracted twice with aq sodium thiosulfate to remove excess iodine. Then the organic solution was extracted twice with brine, dried ($MgSO_4$), and concentrated to afford 5.6 g of the title compound as a yellow solid, a 77% yield. m.p. 58.5–64° C.

EXAMPLE 41

N,N-Diethyl-3-fluoro-6-formyl-2-(trimethylsilyl) benzamide 5.34 g of the compound of Example 4 and 1.7 mL DMF were combined according to General Method B. The resulting reaction mixture was poured into ice water. $CH_2Cl_2$ was added, and the mixture was extracted with aq $NaHCO_3$, followed by brine, then was dried ($MgSO_4$), concentrated, and purified by HPLC with 1:3 ethyl acetate/hexanes to afford 3.5 g of the title compound as a clear oil, a yield of 60%.

EXAMPLE 42

2-[(Diethylamino)carbonyl]-4-fluoro-3-(trimethylsilyl)benzoic acid, methyl ester 20.06 g of the compound of Example 4 and excess $CO_2$ gas were combined according to General Method A. The resulting reaction was poured into water and acidified with 2N HCl. The solid which formed was collected by filtration and dried to yield the corresponding acid.

A couple of drops of DMF were added to a mixture of this acid (9.34 g, 30.0 mmol) and thionyl chloride (11.89 g, 100 mmol) in toluene (100 mL). The reaction was complete after 1 h at 70–74° C. The mixture was concentrated under vacuum to remove the excess thionyl chloride. The resulting crude acid chloride (0.98 g, 3.0 mmol) was dissolved in methanol (25 mL), and triethylamine (2 eq) was added dropwise. After addition, the reaction was diluted with ethyl acetate and extracted with dilute aq HCl, then with sat aq $NaHCO_3$. The organic solution was dried ($MgSO_4$) and concentrated to afford 0.54 g of the title compound as a solid, a 55% yield. m.p. 46° C.

EXAMPLE 43

2-[(Diethylamino)carbonyl]-4-fluoro-3-(trimethylsilyl)benzoic acid, 1-methylethyl ester The acid chloride (0.98 g, 3.0 mmol) prepared as in Example 42 was dissolved in isopropyl alcohol (25 mL), and triethylamine (1 mL, 7.0 mmol) was added dropwise. After stirring overnight at ambient temperature, the mixture was diluted with ethyl acetate and extracted with dilute aq HCl, then with sat aq $NaHCO_3$. The organic solution was dried ($MgSO_4$), concentrated, and purified by RC with 7:3 hexanes/ethyl acetate to afford the title compound as a colorless oil.

EXAMPLE 44

N,N,2-Triethyl-6-(trimethylsilyl)benzamide

The compound of Example 2 (2.49 g, 10 mmol) and ethyl iodide (4.68 g, 30 mmol) were combined according to General Method B. The resulting reaction mixture was poured into ice water. Ether was added, and the mixture was extracted with aq $NaHCO_3$ followed by brine, then was dried ($MgSO_4$) and concentrated to afford 2.83 g of the title compound as a colorless oil, a 100% yield.

EXAMPLE 45

2-Chloro-N-ethyl-6-(trimethylsilyl)benzamide

The compound of Example f (2.2 g, 0.012 mol) was reacted with TMSCl (3.91 g, 0.036 mol) using General Method A. The title compound was recrystallized from ether/hexanes as a solid. m.p. 105–107° C.

EXAMPLE 46

2-Chloro-N-ethyl-N-(methoxymethyl)-6-(trimethylsilyl)benzamide

A 2M THF solution of tert-butylmagnesium chloride (2.5 mL, 5 mmol) was added to an ice water cooled solution of the compound of Example 45 (1.28 g, 5 mmol) in THF (25 mL). Chloromethyl methyl ether (0.44 g, 5.5 mmol) was then added and the reaction mixture was stirred at ambient temperature for 1 h and then partitioned between water and ethyl acetate. The organic solution was dried ($MgSO_4$), concentrated, and purified by RC with 1:9 ethyl acetate/hexanes to afford 0.80 g of the title compound as a colorless oil, a 53% yield.

EXAMPLE 47

N-Acetyl-2-chloro-N-ethyl-6-(trimethylsilyl)benzamide 1M sodium bis(trimethylsilyl)amide in THF (5.5 mL, 5.5 mmol) was added dropwise over several min to a solution of the compound of Example 45 (1.28 g, 5 mmol) in THF (30 mL). The resulting mixture was cooled with a water bath while a solution of acetyl chloride (0.432 g, 5.5 mmol) in THF (10 mL) was added, maintaining the internal reaction temperature –25° C. After 1 h, the resulting reaction mixture was partitioned between sat aq $NaHCO_3$ and ether. The ether phase was dried ($MgSO_4$), concentrated, and purified by RC with 1:4 ethyl acetate/hexanes to afford 0.25 g of the title compound as a pale yellow oil, a 17% yield.

EXAMPLE 48

N-Ethyl-2-methyl-6-(trimethylsilyl)benzamide 1.3M s-BuLi in cyclohexane (25.4 mL, 0.033 mol) was added dropwise to THF (50 mL), TMEDA (3,83 g, 0.033 mol), and the compound of Example c (4.10 g, 0.015 mol), cooled to –78° under nitrogen with stirring. After stirring for 20 min, MeI (2.45 g, 0.01725 mol) was added all at once. The mixture was stirred for 1 h, and 25% citric acid (50 mL) was added. The mixture was extracted three times with $CH_2Cl_2$. The combined extracts were washed twice with water, dried ($MgSO_4$), and concentrated. To the resulting mixture were added 30 mL thionyl chloride and 5 drops of DMF. After stirring at RT overnight, the mixture was concentrated to dryness; 50 mL toluene were added; and again the mixture was concentrated. This process was repeated 3 times. The crude product, a brown oil, was dissolved in 30 mL toluene and added to a 100 mL solution of 70% ethyl amine in water which had been cooled to 5° in an ice bath. After stirring overnight, the mixture was washed with 10% HCl and three times with water, dried ($MgSO_4$), concentrated, and purified by HPLC eluting with 1:3 ethyl acetate/hexanes. Two fractions were obtained. When each was concentrated, Compound 48 crystallized as a white solid in a 20% yield. m.p. 115–117° C. Compound 49 crystallized as a white solid in a 42% yield. m.p. 64–66° C.

EXAMPLE 49

N-Ethyl-2-(trimethylsilyl)benzamide

N-Ethylbenzamide (74.5 g, 500 mmol) and TMSCl (135.8 g, 1.25 mol) were combined according to General Method C and purified by HPLC with 1:4 ethyl acetate/hexanes to afford 75.59 g of the title compound, as a white solid, a 68% yield. m.p. 64.0–66.0° C.

EXAMPLE 50

N-Ethyl-N-(methoxymethyl)-2-(trimethylsilyl)benzamide

A 1M THF solution of sodium bis(trimethylsilyl)amide (52.5 mL, 52.5 mmol) was added dropwise over 5 min to a solution of the compound of Example 49 (11.07 g, 50 mmol) in THF (100 mL). The resulting mixture was cooled with a dry ice/acetone bath while neat chloromethyl methyl ether (4.83 g, 60 mmol) was added, maintaining the internal reaction temperature <–70° C. The cold bath was removed and the resulting reaction mixture was allowed to warm for 1 h, then was partitioned between sat aq $NaHCO_3$ and ether. The ether phase was dried ($MgSO_4$), concentrated, and purified by HPLC with 3:17 ethyl acetate/hexanes to afford 6.55 g of the title compound as a colorless oil, a 49% yield.

EXAMPLE 51

N,N-Diethyl-2-methyl-6-(trimethylsilyl)thiobenzamide

A mixture of the compound of Example 3 (2.0 g, 7.6 mmol) and Lawesson's reagent (2.3 g, 5.7 mmol) in xylenes (50 mL) was refluxed for 16 h, then was cooled, and filtered. The filtrate was partitioned between ether and water. The organic layer was washed with 10% HCl and brine, dried ($MgSO_4$), and concentrated. The crude product was purified by RC using with 1:9 ethyl acetate/hexanes to afford 1.4 g of the title compound as a yellow oil, which crystallized upon standing, a 66% yield. m.p. 82–83° C.

EXAMPLE 52

N,N-Diethyl-6-(difluoromethyl)-3-fluoro-2-(trimethylsilyl)benzamide

To a solution of DAST (55 mg, 0.34 mmol) in 1 mL $CH_2Cl_2$ at 0° C. was added the compound of Example 41 (100 mg, 0.34 mmol). The solution was refluxed for 16 h and a second molar equivalent of DAST was added. This procedure was continued until the reaction was complete by GC analysis. The mixture was poured onto 10 g of ice and the aq solution was extracted with $CH_2Cl_2$. The extracts were combined, washed with brine, dried ($MgSO_4$), and concentrated. The product was purified by RC using with 1:9 ethyl acetate/hexanes to give 800 mg of the title compound as a yellow solid, a 92% yield. m.p. 65–67° C.

EXAMPLE 53

N,N-Diethyl-3-fluoro-6-methyl-2-(trimethylsilyl)thiobenzamide

The title compound was prepared from the compound of Example 1 and Lawesson's reagent according to the procedure for Example 51. The crude product was flash chromatographed on a 6" silica gel column with 1:19 ethyl acetate/hexanes and then recrystallized from hexanes to give 820 mg of the title compound as a white solid, a 78% yield. m.p. 68–69° C.

EXAMPLE 54

N,N-Diethyl-3-fluoro-6-(hydroxymethyl)-2-(trimethylsilyl)benzamide

The compound of Example 41 (1.2 g, 4.1 mmol) and sodium borohydride (200 mg, 5.3 mmol) in ethanol (20 mL)

were stirred at ambient temperature for 2 h. The solution was concentrated and partitioned between ether and 10% citric acid. The ether layer was washed with water and then brine, dried (MgSO$_4$), concentrated, and recrystallized from cold hexanes to afford 1.0 g of the title compound, an 82% yield. m.p. 107–108° C.

EXAMPLE 55

N,N-Diethyl-3-fluoro-6-(fluoromethyl)-2-(trimethylsilyl)benzamide

A solution of DAST (400 mg, 2.5 mmol) and the compound of Example 54 (660 mg, 2.2 mmol) in CH$_2$Cl$_2$ (30 mL) was stirred for 2 h at 25° C. The solution was poured into ice water (50 mL) and extracted with CH$_2$Cl$_2$. The organic extracts were combined, washed with brine, dried (MgSO$_4$), concentrated, and purified by RC with 1:9 ethyl acetate/hexanes to give 550 mg of the title compound as a yellow oil, an 83% yield.

EXAMPLE 56

N,N-Diethyl-3,6-difluoro-2-(trimethylsilyl)benzamide

Diethyl amine (15.4 g, 210 mmol) and 2,5-difluorobenzoyl chloride (17.6 g, 100 mmol) were reacted using General Method E1 to afford 20.0 g of N,N-diethyl-2,5-difluorobenzamide as a clear oil, a 94% yield.

The title compound was prepared from this compound and 2.0 eq TMSCl according to General Method A. The crude product was purified by HPLC with 1:9 ethyl acetate/hexanes to give 4.8 g of the desired product as a clear oil, an 84% yield.

EXAMPLE 57

N,N-Diethyl-3-fluoro-4-methyl-2-(trimethylsilyl)benzamide 1.3M s-BuLi (9.2 mL, 12 mmol) was added dropwise to a −78° C. cooled solution of the compound of Example 4 (3.48 g, 10 mmol) and TMEDA (1.8 mL, 12 mmol) in THF. The reaction mixture was warmed to −60° C., stirred for 3 h, cooled to −78° C., and MeI (5.0 g, 36 mmol) was added. After an initial exotherm to −58° C., the reaction mixture was allowed to warm to 0° C. and worked up in the usual manner. The crude product was purified by HPLC with 1:4 ethyl acetate/hexanes to give 300 mg of the title compound as a clear oil, a 71% yield.

EXAMPLE 58

N,N-Diethyl-4-methyl-2-(trimethylsilyl)benzamide

N,N-Diethyl-4-methylbenzamide was prepared from 4-methylbenzoyl chloride and diethylamine according to General Method E1. The crude product was recrystallized from cold hexanes to give 30.4 g of the desired compound as a white solid, a 98% yield. m.p. 54° C.

The title compound was prepared from this compound and 3.0 eq TMSCl according to General Method A. The crude product was purified by HPLC with 3:17 ethyl acetate/hexanes to give 7.0 g of the title compound as a clear oil, an 89% yield.

EXAMPLE 59

N,N-Diethyl-2-chloro-4-methyl-6-(trimethylsilyl)benzamide

The title compound was prepared from the compound of Example 58 and 1.2 eq hexachloroethane according to General Method A. Purification by HPLC with 1:9 ethyl acetate/hexanes afforded 1.6 g of the title compound as a clear oil, a 54% yield.

EXAMPLE 60

N,N-Diethyl-2,4-dimethyl-6-(trimethylsilyl)benzamide

The title compound was prepared from the compound of Example 58 and MeI (4.0 eq) according to General Method A. Purification by HPLC with 3:17 ethyl acetate/hexanes gave 1.4 g of the title compound as a clear oil, an 83% yield.

EXAMPLE 61

N,N-Diethyl-2-(trimethylsilyl)-6-(trifluoromethyl)benzamide

N,N-Diethyl-2-(trifluoromethyl)benzamide was prepared from 2-trifluoromethylbenzoyl chloride and diethylamine according to General Method E1. No purification was needed to obtain 17.2 g of this compound, a 97% yield.

The title compound was prepared from this compound and 3.0 eq TMSCl according to General Method A. The crude material was purified by HPLC with 3:17 ethyl acetate/hexanes to afford 2.7 g of the title compound as a clear oil, an 85% yield.

EXAMPLE 62

N,N-Diethyl-2-(trimethylsilyl)-3,6-bis(trifluoromethyl)benzamide

N,N-Diethyl-2,5-bis(trifluoromethyl)benzamide was prepared from 2,5-bis(trifluoromethyl)benzoyl chloride and diethylamine according to General Method E1. The desired intermediate was isolated in quantitative yield (11.3 g) without additional purification.

The title compound was prepared from this compound and 3.7 eq TMSCl according to General Method A. Purification by HPLC with 1:19 ethyl acetate/hexanes, followed by kugelrohr distillation (90° C. @ 0.1 mm Hg) afforded 2.0 g of the title compound as a white solid, a 52% yield. m.p. 55–56° C.

EXAMPLES 63 AND 64

Compound 63: N,N-Diethyl-5-methyl-2-(trimethylsilyl)benzamide

Compound 64: N,N-diethyl-3-methyl-2-(trimethylsilyl)benzamide

These compounds were prepared from N,N-diethyl-3-methylbenzamide and 2.0 eq TMSCl according to General Method A. Purification by HPLC using 1:9 ethyl acetate/hexanes gave two products. Compound 63 was isolated as 6.0 g of a clear oil, a 46% yield. Compound 64 was isolated as 2.3 g of a clear oil, a 17% yield.

EXAMPLE 65

N,N-Diethyl-2-chloro-3-methyl-6-(trimethylsilyl)benzamide

The title compound was prepared according to General Method A from the compound of Example 63 and 1.3 eq hexachloroethane. Purification by RC using 1:4 ethyl acetate/hexanes gave 500 mg of the title compound as a yellow solid, a 44% yield. m.p. 42–44° C.

EXAMPLE 66

N,N-Diethyl-2-chloro-6-(triethylsilyl)benzamide

The title compound was prepared according to General Method A from the compound of Example e and 1.4 eq chlorotriethylsilane. Purification by HPLC with 1:19 ethyl acetate/hexanes gave 6.0 g of the desired product as a clear oil, a 92% yield.

EXAMPLE 67

N,N-Diethyl-2-chloro-6-(dimethylphenylsilyl)benzamide

The title compound was prepared from the compound of Example e and 1.1 eq dimethylphenylsilyl chloride according to General Method A. Purification by HPLC with 1:9 ethyl acetate/hexanes gave 6.3 g of the desired product as a clear oil, a 91% yield.

EXAMPLE 68

N,N-Diethyl-2-chloro-6-[tris(1-methylethyl)silyl]benzamide

The title compound was prepared according to General Method A from the compound of Example e and 1.1 eq triisopropylsilyl chloride. Purification by HPLC using 1:19 ethyl acetate/hexanes gave 5.5 g of the desired product as of a clear oil, a 75% yield.

EXAMPLE 69

N,N-Diethyl-2-chloro-6-[(chloromethyl)dimethylsilyl]benzamide

The title compound was prepared according to General Method A from the compound of Example e and 1.5 eq (chloromethyl)dimethylsilyl chloride. Purification by HPLC using 1:9 ethyl acetate/hexanes gave 5.4 g of the desired compound as a yellow oil, an 85% yield.

EXAMPLE 70

N-Ethyl-2-(trimethylsilyl)-3-thiophenecarboxamide

A mixture of thiophene-3-carboxylic acid (20.0 g, 178 mmol), thionyl chloride (30 mL, 411 mmol), and catalytic DMF (5 drops) was stirred at RT overnight. This solution was concentrated under vacuum, and stripped several times from toluene to remove all traces of excess thionyl chloride. Ethyl amine hydrochloride (29.03 g, 356 mmol) was then added to a solution of this crude acid chloride dissolved in $CH_2Cl_2$ (50 mL). Pyridine (31.64 g, 400 mmol) was added, and after 1 h of stirring the reaction was washed with 10% HCl followed with water, dried ($MgSO_4$), concentrated, and recrystallized from EtOAc/hexanes to give 14.9 g of N-ethyl-3-thiophenecarboxamide as a tan solid, a 76% yield. m.p. 115–117° C.

1.3M s-BuLi in cyclohexane (37.23 mL, 48.4 mmol) was added dropwise to a dry-ice/acetone cooled solution of N-ethyl-3-thiophenecarboxamide (3.41 g, 22 mmol) and TMEDA (5.62 g, 48.4 mmol) in THF (100 mL). After stirring for 30 min at −78° C., TMSCl (5.26 g, 48.4 mmol) was added in a single portion. The reaction was allowed to slowly warm to −10° C. over 1 h, then was quenched with dilute aq citric acid and extracted with ethyl acetate (3×). The combined organic solutions were dried ($MgSO_4$), concentrated, and purified by HPLC with 3:7 EtOAc/hexanes to give 1.4 g of the title compound as a white solid, a 28% yield. m.p. 114–116° C.

EXAMPLE 71

N,N-Diethyl-6-chloro-3-methyl-2-(trimethylsilyl)benzamide

The title compound was prepared according to General Method A from the compound of Example 64 and 1.1 eq hexachloroethane. Purification by HPLC 1:9 ethyl acetate/hexanes gave 1.5 g of an oil which crystallized upon standing, an 83% yield. m.p. 36–37° C.

EXAMPLE 72

3-Chloro-N-ethyl-2'-methyl-[1,1'-biphenyl]-2-carboxamide

The title compound was prepared according to General Method D except that 1-butanol instead of $CH_2Cl_2$ was used to extract the boron intermediate. The crude intermediate was further reacted with 2-bromotoluene as described in General Method D to give the title compound as a white solid (recrystallized from toluene) in 55% overall yield. m.p. 131–134° C.

EXAMPLE 73

2-Chloro-N-ethyl-6-(1-naphthalenyl)benzamide

The title compound was prepared from the compound of Example f and 1-bromonaphthalene (0.76 g, 3.65 mmol) according to General Method D. It was obtained as 0.28 g of a white solid, a 28% yield. m.p. 181–182° C.

EXAMPLE 74

N,N-Diethyl-3-fluoro-2-(trimethylsilyl)thiobenzamide

A mixture of N,N-diethyl-3-fluorobenzamide (4.69 g, 24 mmol) (cf Mills, et al., "Directed Ortho Metalation of N,N-Diethylbenzamides. Silicon Protection of Ortho Sites and the o-Methyl Group," *J. of Organic Chemistry* 54: 4372–4385, 1989), Lawesson's reagent (6.47 g, 16 mmol) and xylenes (150 mL) was refluxed overnight, then was concentrated and kugelrohr distilled (105–110° C. at 0.25 torr) to yield 4.8 g N,N-diethyl-3-(fluoro)thiobenzamide as a yellow oil, a 95% yield.

This compound and 1.8 eq TMSCl were combined according to General Method A and purified by HPLC with 1:9 ethyl acetate/hexanes to give 3.7 g of the title compound as a yellow solid, a 77% yield. m.p. 71–73° C.

EXAMPLE 75

N,N-Diethyl-3-fluoro-4-methyl-2-(trimethylsilyl)thiobenzamide

The title compound was prepared from the compound of Example 74 and 3.0 eq MeI according to General Method A and recrystallized from cold hexanes/ethyl acetate to give 2.5 g of the title compound, an 82% yield. m.p. 96–97° C.

EXAMPLE 76

2-Chloro-N-ethyl-6-(trimethylsilyl)thiobenzamide

The title compound was prepared from the compound of Example 45 using the procedure of Example 51. m.p. 158.0–159.0° C.

EXAMPLE 77

2-Chloro-6-(trimethylsilyl)benzenecarbothioic acid, S-ethyl ester

The compound of Example b (1.48 g, 0.006 mol), $CH_2Cl_2$ (50 mL), ethanethiol (0.44 g, 0.007 mol), and 4-(N,N-dimethylamino)pyridine (0.86 g, 0.007 mol) were allowed to stir at RT overnight. The mixture was washed with 10% HCl and three times with water, dried ($MgSO_4$), and concentrated. The crude product was purified by RC, eluting with 1:3 ethyl acetate/hexanes. The title compound was obtained as a clear oil in 61% yield.

EXAMPLES 78–81

The following compounds were prepared as in Example 77 using the appropriate thiol ester in the yields shown.

| Ex. No. | Compound Name | Yield |
|---|---|---|
| 78 | 2-Chloro-6-(trimethylsilyl)-benzenecarbothioic acid, S-(1-methylethyl) ester | 35% |
| 79 | 2-Chloro-6-(trimethylsilyl)-benzenecarbothioic acid, S-propyl ester | 80% |
| 80 | 2-Chloro-6-(trimethylsilyl)-benzenecarbothioic acid, S-(1-methylpropyl) ester | 47% |
| 81 | 2-Chloro-6-(trimethylsilyl)-benzenecarbothioic acid, S-(2-methylpropyl) ester | 81% |

EXAMPLE 82

N-Ethyl-2-(trifluoromethyl)-6-(trimethylsilyl) benzamide 2-(Trifluoromethyl)benzoyl chloride and ethyl amine were combined according to General Method E1 and recrystallized from cold hexanes to give 7.7 g N-ethyl-2-(trifluoromethyl)benzamide as a white solid, a 67% yield. m.p. 73–76° C.

This compound was combined with 2.0 eq TMSCl according to General Method C. Recrystallization from ethyl acetate/hexanes gave 2.0 g of the title compound as a white solid, a 69% yield. m.p. 134–135° C.

EXAMPLE 83

N-Ethyl-2-chloro-6-[(chloromethyl)dimethylsilyl] benzamide

The title compound was prepared from the compound of Example f and 2.0 eq (chloromethyl)dimethylsilyl chloride according to General Method C. Recrystallization from ethyl acetate gave 3.0 g of the desired compound as a white solid, a 52% yield. m.p. 88–89° C.

EXAMPLE 84

N,N-Diethyl-2,3-dichloro-6-(trimethylsilyl) benzamide

The title compound was prepared from the compound of Example 39 and 1.5 eq hexachloroethane according to General Method A. Purification by RC with 1:4 ethyl acetate/hexanes afforded 320 mg of the desired compound as a white solid, a 14% yield. m.p. 143–147° C.

EXAMPLE 85

N,N-Diethyl-2-chloro-3-ethyl-6-(trimethylsilyl) benzamide

The title compound was prepared from the compound of Example 39 and 8.5 eq ethyl iodide according to General Method A. Purification by RC with 1:4 ethyl acetate/hexanes gave 1.3 g of the desired compound as a green oil, a 57% yield.

EXAMPLE 86

N,N-Diethyl-2-chloro-3,6-bis(trimethylsilyl) benzamide

The title compound was prepared from the compound of Example 39 and 2.0 eq TMSCl according to General Method A. Purification by HPLC with 1:4 ethyl acetate/hexanes gave 0.9 g of the title compound as a white solid, a 37% yield. m.p. 93–96° C.

EXAMPLE 87

N-Ethyl-2-chloro-6-(ethenyldimethylsilyl)benzamide

The title compound was prepared from the compound of Example f and 1.5 eq vinyldimethylsilyl chloride according to General Method C. Purification by HPLC with 1:4 ethyl acetate/hexanes gave 630 mg of the desired product as a white solid, a 9% yield. m.p. 86–89° C.

EXAMPLE 88

N,N-Diethyl-2-chloro-3-fluoro-6-(trimethylsilyl) benzamide

N,N-Diethyl-2-chloro-3-fluorobenzamide was prepared from N,N-diethyl-3-fluorobenzamide (prepared from 3-fluorobenzoic acid and diethyl amine as generally described above) and 1.4 eq hexachloroethane according to General Method A. Purification by HPLC WITH 1:4 ethyl acetate/hexanes gave 3.3 g of the desired compound as a clear oil, a 56% yield.

This compound was combined with 2.0 eq TMSCl according to General Method A. Purification by HPLC with 3:7 ethyl acetate/hexanes gave 2.2 g of the title compound as a clear oil, a 50% yield.

EXAMPLE 89

N-Ethyl-2-chloro-6-(1,1-dimethylethoxy)benzamide

To a solution of the compound of Example f (3.7 g, 20 mmol) and TMEDA (6.0 mL, 40 mmol) in anhydrous THF (100 mL) at −78° C. under nitrogen was added dropwise 1.3M s-BuLi (34 mL, 44 mmol). After 30 min $MgBr_2.Et_2O$ (15.5 g, 60 mmol) was added, and the solution was warmed to ambient temperature, then cooled to −78° C. and stirred for 1 h. t-Butylperoxy benzoate (4.3 g, 22 mmol) was added, and the solution was warmed to −30° C. and worked up in the usual manner. Purification by HPLC with 3:17 ethyl acetate/hexanes gave 1.7 g of the desired compound as a white solid, a yield of 33%. m.p. 126–127° C.

EXAMPLE 90

2-[1,1-Dimethylethyl)thio]-N-ethyl-6-fluorobenzamide

A solution of 2-methyl-2-propanethiol (2.7 g, 0.03 mol), THF (100 mL), sodium hydride (0.79 g, 0.033 mol), and the compound of Example g (3.17 g, 0.015 mol), were stirred at RT overnight followed by refluxing overnight. The mixture was allowed to cool and sat aq NaHCO$_3$ (50 mL) was added. This mixture was extracted with three 50 mL portions of ethyl acetate. The organics were combined and washed twice with water, dried (MgSO$_4$) and concentrated. The concentrate was purified by HPLC, eluting with 1:4 ethyl acetate/hexanes. This oxazoline compound was obtained as a yellow oil in 83% yield.

This product was then carried through Steps 1, 2, 3, and 4, as follows:

Step 1, Oxazoline Ring Opening

A 2M solution of trifluoromethanesulfonic anhydride (1.5 eq) in CH$_2$Cl$_2$ was added dropwise to an ice water-cooled 0.67M solution of the oxazoline compound (1 eq) in CH$_2$Cl$_2$. The resulting solution was stirred at 0° C. for 1 min, then was poured into an equal volume of ice-water and vigorously stirred for 15 min. The organic layer was washed twice with 10% HCl, dried (MgSO$_4$), and concentrated. Purification by HPLC in ethyl acetate/hexanes over silica was accomplished.

Step 2, Methylation with Diazomethane

A freshly prepared solution of diazomethane in anhydrous ethyl ether was added in excess to an ether solution of the product from Step 1. The resulting yellow solution was allowed to stand at RT overnight before being quenched with acetic acid (5 mL). The organic layer was then washed with 10% HCl followed by 2.5N aq NaOH, dried (MgSO$_4$), and concentrated to afford the N-methylated sulfonamide.

Step 3, Saponification of N-Methylated Sulfonamide

Potassium hydroxide (3 eq) and the N-methylated sulfonamide from Step 2 in DMSO were stirred at 110° C. for 3–4 h. The resulting solution was cooled, diluted with an equal volume of water, and extracted three times with ether. The aqueous layer was then acidified with 10% HCl and extracted three times with ether. The latter extracts were combined, dried (MgSO$_4$), and concentrated to yield the 2,6-disubstituted-benzoic acid.

Step 4, Preparation of 2,6-Disubstituted-N-Ethyl-Benzamide

Oxalyl chloride (2.2 eq) and the 2,6-disubstituted-benzoic acid (1 eq) from Step 3 were stirred in toluene with catalytic DMF at RT under nitrogen for 1 h. The solvent was removed in vacuo before additional toluene (50 mL) was added and similarly removed. The resulting acid chloride was dissolved in CH$_2$Cl$_2$ (50 mL) treated with 70% ethyl amine (3.3 eq) and stirred an additional 30 min at RT. The organic layer was then washed twice with 10% HCl and twice with water, dried (MgSO$_4$), and concentrated to yield a white solid. Purification was by recrystallization from ether/hexanes. The resulting final product was recrystallized from ether/hexanes. The title compound was recovered as a white solid. m.p. 107–109° C.

EXAMPLE 93

2-(2,2-Dimethylpropyl)-N-ethyl-6-fluorobenzamide

A solution of p,p'-di-t-butyl biphenyl (5.559 g, 0.021 mol) and THF (100 mL) was stirred at 0° C. under an atmosphere of argon. Lithium wire (0.021 mol, 0.15 g) was added in small pieces and the mixture was allowed to stir at 0° C. for 24 h. The mixture was cooled to −78° C. and neopentyl chloride (2.0 g, 0.01875 mol) was added dropwise. The mixture was stirred at −78° C. for 1 h, and the compound of Example g (3.17 g, 0.015 mol) was added all at once. The mixture was continuously stirred for 4 h and 50 mL sat aq NaHCO$_3$ was added. This mixture was extracted with three 50 mL portions of ethyl acetate. The combined extracts were washed twice with water, dried (MgSO$_4$), and concentrated. The crude concentrate was purified by HPLC eluting with 1:4 ethyl acetate/hexanes. The oxazoline was as a clear oil in 27% yield.

This product was then carried through Steps 1–4 of Example 90. The resulting final product was recrystallized from ether/hexanes. The title compound was obtained as a white solid. m.p. 125–126° C.

EXAMPLE 94

N-Ethyl-2-fluoro-6-(2-methylphenyl)benzamide

A solution of 2-bromotoluene (2.82 g, 0.0165 mol) and THF (100 mL) was stirred magnetically under argon at −78° C. 1.3M s-BuLi in cyclohexane (0.018 mol, 13.85 mL) was added dropwise. The mixture was stirred for 0.5 h and the compound of Example g (3.17 g, 0.015 mol) was added all at once. The mixture was continuously stirred for 4 h and sat aq NaHCO$_3$ (50 mL) was added. The mixture was extracted with three 50 mL portions of ethyl acetate. The combined extracts were washed twice with water, dried (MgSO$_4$), and concentrated. The concentrate was purified by HPLC, eluting with 1:4 ethyl acetate/hexanes. The oxazoline was obtained as a clear oil in 73% yield.

This product was then carried through Steps 1–4 of Example 90. The resulting final product was recrystallized from ether/hexanes. The title compound was obtained as a white solid. m.p. 75–77° C.

EXAMPLE 95

2-Chloro-N-(1-methylethyl)-N-propyl-6-(trimethylsilyl)benzamide

A solution of propionyl chloride (23.13 g, 250 mmol) in ether (100 mL) was added dropwise to an ice water-cooled solution of iso-propylamine (29.56 g, 500 mmol) in ether (200 mL). The resulting mixture was stirred at RT for 1 h, then was filtered to remove iso-propylamine hydrochloride. The solution of N-iso-propylpropionamide (37% of the filtrate, ~92 mmol) was diluted with THF (90 mL) and cooled with an ice water bath while a 2M THF solution of borane-dimethylsulfide (100 mL, 200 mmol) was added dropwise. The resulting solution was stirred at RT for 1 h, then was refluxed for 2 h. With ice-water cooling, the excess borane-dimethylsulfide was quenched by the dropwise addition of methanol (30 mL), and the mixture was allowed to stand at RT overnight. HCl gas was bubbled into the solution, and the N-propyl-N-iso-propylamine hydrochloride was collected.

Triethylamine (27.89 mL, 200 mmol) was added to a mixture of the compound of Example b (2.47 g, 10 mmol) and N-propyl-N-iso-propylamine hydrochloride (~92 mmol) in toluene (100 mL). The reaction was stirred overnight at ambient temperature, then was partitioned between ethyl acetate and dilute citric acid. The organic phase was washed with brine, dried (MgSO$_4$), and concentrated to afford 2.50 g of the title compound as a waxy amber solid, an 80% yield.

EXAMPLE 96

2-Chloro-N-ethyl-N-(1-methylheptyl)-6-(trimethylsilyl)benzamide

A solution of acetyl chloride (7.11 mL, 100 mmol) was added dropwise to an ice water-cooled solution of 1-methylheptyl amine (8.30 g, 64 mmol) and triethylamine (20.91 mL, 150 mmol) in THF (100 mL). The resulting mixture was stirred at RT for 1 h, then was diluted with ethyl acetate and washed twice with 10% HCl, twice with sat aq NaHCO$_3$, and then twice with brine. The organic solution was dried (MgSO$_4$), and concentrated to afford 8.13 g N-(1-methylhept-1-yl)acetamide, a 73% yield.

A 2M THF solution of borane-dimethylsulfide (31.5 mL, 63 mmol) was added dropwise to an ice water-cooled solution of N-(1-methylhept-1-yl)acetamide (5.13 g, 30 mmol) in THF (60 mL). The resulting solution was stirred at RT for 1 h, then was refluxed overnight. With ice-water cooling, the excess borane-dimethylsulfide was quenched by the dropwise addition of methanol (10 mL), and the mixture was allowed to stand at RT overnight. The amine hydrochloride could not be precipitated with the addition of HCl gas, so the amine hydrochloride was extracted into dilute HCl. The acidic aq solution was extracted with ether, then made basic and extracted with ethyl acetate. The ethyl acetate solution was dried (MgSO$_4$) and concentrated to afford 3.70 g of impure N-ethyl-N-(1-methylhept-1-yl) amine as an amber oil.

Triethylamine (2.02 g, 20 mmol) was added to a mixture of the compound of Example b (2.47 g, 10 mmol) and N-ethyl-N-(1-methylhept-1-yl)amine (3.15 g, 20 mmol) in toluene (25 mL). The reaction was stirred 2.5 h at ambient temperature, then was partitioned between ethyl acetate and dilute citric acid. The organic phase was washed twice with sat aq NaHCO$_3$, followed with brine, then was dried (MgSO$_4$), concentrated, and kugelrohr distilled under vacuum. The fraction which distilled at 157° C. was collected to afford 1.16 g of the title compound as an amber oil, a 38% yield.

EXAMPLE 97

2-(Difluoromethyl)-N,N-diethyl-6-(trimethylsilyl) benzamide

The compound of Example 2 (9.96 g, 40 mmol) and a solution of DMF (3.65 g, 50 mmol) in THF (20 mL) were combined according to General Method A. The resulting reaction mixture was partitioned between ethyl acetate and dilute citric acid. The organic phase was washed with sat aq NaHCO$_3$ followed with brine, dried (MgSO$_4$), and concentrated to afford 8.35 g of N,N-diethyl-2-trimethylsilyl-6-formylbenzamide as a white solid, a 75% yield. m.p. 63.5–65.5° C.

DAST (0.63 mL, 4.8 mmol) was added to an ice water-cooled solution of N,N-diethyl-2-trimethylsilyl-6-formylbenzamide (0.665 g, 2.4 mmol) in CH$_2$Cl$_2$ (20 mL). The solution was warmed to RT and stirred for 17 h, then additional DAST (1.0 mL, 7.6 mmol) was added. This mixture was stirred for 1 additional day, then was quenched with ice-water. The CH$_2$Cl$_2$ solution was dried (MgSO$_4$) and concentrated to afford 0.69 g of the title compound as an amber oil, a yield of 96%.

EXAMPLE 98

N,N-Diethyl-2-(fluoromethyl)-6-(trimethylsilyl) benzamide

Sodium borohydride (1.0 g, 26.4 mmol) was added to a solution of N,N-diethyl-2-trimethylsilyl-6-formylbenzamide, prepared in Example 97, (5.54 g, 20 mmol) in absolute ethanol (100 mL). After 3 h the mixture was diluted with ether, extracted three times with brine, dried (MgSO$_4$), concentrated, and recrystallized from 1:1 ethyl acetate/hexanes to afford 4.12 g of N,N-diethyl-2-trimethylsilyl-6-hydroxymethylbenzamide as a white solid, a 74% yield. m.p. 81–82.5° C.

DAST (0.66 mL, 5.0 mmol) was added to an ice water-cooled solution of this compound (1.395 g, 5.0 mmol) in CH$_2$Cl$_2$ (40 mL). The solution was warmed to RT and stirred for 4 h, then was quenched with ice-water and extracted with CH$_2$Cl$_2$. The CH$_2$Cl$_2$ extracts were combined, dried (MgSO$_4$), and concentrated to afford 1.38 g of the title compound as an amber oil, a 98% yield.

EXAMPLE 99

2-Chloro-6-(trimethylsilyl)-2,2-dimethylhydrazide-benzoic acid

A solution of the compound of Example b (1.48 g, 0.006 mol), CH$_2$Cl$_2$ (50 mL), 1,1-(dimethyl)hydrazine (0.42 g, 0.007 mol), and pyridine (0.55 g, 0.007 mol) was allowed to stir at RT overnight. The reaction mixture was washed with 10% HCl and three times with water, dried (MgSO$_4$), and concentrated. The title compound was recrystallized as a white solid in 43% yield. m.p. 134–135° C.

EXAMPLES 101–108

The following examples were prepared by reaction of the compound of Example b and the appropriate amine by refluxing in toluene or by overnight ambient temperature reaction in dioxane in the presence of an acid scavenger such as triethylamine. The melting points are reported in ° C.

| Ex. No. | Compound Name | M.P. |
| --- | --- | --- |
| 101 | 2-Chloro-N-[[4-(1,1-dimethylethyl)phenyl]methyl]-N-methyl-6-(trimethylsilyl)-benzamide | — |
| 102 | 2-Chloro-N-[[4-(trifluoromethyl)phenyl]methyl]-6-(trimethylsilyl)-benzamide | 159–160 |
| 103 | 2-Chloro-N-methyl-N-[[4-(trifluoromethyl)phenyl]methyl]-6-(trimethylsilyl)-benzamide | 85–86 |
| 104 | 2-Chloro-N-(6,6-dimethyl-2-hepten-4-ynyl)-N-ethyl-6-(trimethylsilyl)benzamide | — |
| 105 | 2-Chloro-N-methyl-N-(3-phenyl-2-propenyl)-6-(trimethylsilyl)benzamide | — |
| 106 | 2-Chloro-N-2-propenyl-6-(trimethylsilyl)benzamide | 97–99 |
| 107 | 2-Chloro-N-(1,1-dimethyl-2-propynyl)-6-(trimethylsilyl)benzamide | 155–157 |
| 108 | 2-Chloro-N-(2-propynyl)-6-(trimethylsilyl)benzamide | 112–114 |

EXAMPLE 109

[2-Chloro-6-(trimethylsilyl)phenyl]carbamic acid, ethyl ester

A mixture of the compound of Example h (10 mmol) and ethanol (75 mL) was refluxed for 1 h. The mixture was concentrated and the residue dissolved in ethyl acetate. The solution was washed twice with water and the solvent removed to yield the crude product, which was recrystallized from hexane. GC/MS showed some remaining isocyanate so the solid was dissolved in ethanol and refluxed again with approx. 0.1 g diazobisbicyclooctane. FID/GC indicated a complete reaction and the ethanol was removed and the title compound recovered. m.p. 109–110° C.

EXAMPLE 110

N-[2-Chloro-6-(trimethylsilyl)phenyl]-N'-ethylurea

To a solution of the compound of Example h (4 mmol) in 50 mL toluene was added 70% ethyl amine (4 mL). The solution was stirred for 0.5 h and then stood overnight. Ethyl acetate was added and the mixture was washed with water. The organic layer was concentrated to a semisolid, which was triturated with hexane. The title compound was collected by filtration as 0.9 g of crystals, an 83% yield. m.p. 161–163° C.

EXAMPLE 111

[2-Chloro-6-(trimethylsilyl)phenyl]carbamic acid, 1,1-dimethylethyl ester o-Chlorophenyl isocyanate (0.16 mol) was dissolved in toluene (250 mL), and tert-butanol (12.9 g, 0.174 mol) was added. After refluxing overnight, the cooled solution was filtered. The solvent was removed from the filtrate and (2-chlorophenyl)carbamic acid, 1,1-dimethylethyl ester was recovered.

This compound was combined with t-BuLi in THF at −71° C. using the procedures described above and then reacted with TMSCl. The title compound was recovered as 1.3 g of crystals. m.p. 90–91° C.

EXAMPLES 112–114

Compound 112: (Z)-2-Chloro-N-1-propenyl-6-(trimethylsilyl)benzamide

Compound 113: (E)-2-Chloro-N-1-propenyl-6-(trimethylsilyl)benzamide

Compound 114: A 50:50 Mixture of Compounds 112 and 113

The compound of Example 106 (17 mmol) and of Wilkinson's catalyst [tris(triphenylphosphine)rhodium(I) chloride] (80 mg) were dissolved in 100 mL toluene and refluxed for four days. The mixture was filtered through silica gel, which was washed with ethyl acetate and combined with the filtrate. The solvent was removed and the mixture was resolved by RC with 1:9 ethyl acetate/hexane to yield two fractions having different tlc spots. The first fraction was concentrated to yield a solid which was recrystallized from hexane to yield 1.9 g of Compound 114 (m.p. 100.0–105.0). This solid (0.25 g) was purified by RC with hexane as a solvent to yield Compound 112 (m.p. 140.0–141.0° C.) and Compound 113 (m.p. 101.0–102.0° C.) as pure isomers.

EXAMPLE 115

2-Chloro-N-ethyl-6-(trimethylstannyl)benzamide 1.3M s-BuLi in cyclohexane (25.8 mL, 33.5 mmol) was added dropwise to a −78° C. cooled solution of the compound of example f (2.80 g, 15.3 mmol) and TMEDA (3.55 g, 30.6 mmol) in THF (100 mL). After stirring the resulting reaction mixture at −78° C. for 15 min, hexamethylditin (5.0 g, 15.3 mmol) was added. The reaction was warmed to −60° C., and then partitioned between ether and water. The ether was dried (MgSO$_4$), concentrated, and purified by silica gel chromatography, eluting with 1:4 ethyl acetate/hexanes, to afford 4.10 g of the title compound as a white solid, a 77% yield. m.p. 78–80° C.

EXAMPLE 116

2-Chloro-N-ethyl-6-(9-phenanthrenyl)benzamide

The title compound was prepared by treatment of 9-bromophenanthrene (0.94 g, 3.65 mmol) according to General Method D. It was obtained as 0.55 g of a white solid, a 56% yield. m.p. 189–191° C.

EXAMPLE 117

N-Ethyl-2-fluoro-6-(trimethylsilyl)benzamide

2-Fluorobenzoyl chloride (2 g, 12.6 mmol) and 70% aq ethyl amine (1.78 g, 27.7 mmol) were combined in CH$_2$Cl$_2$ according to General Method E1, and kugelrohr distilled to give 1.85 g of N-ethyl-2-fluorobenzamide as a colorless oil, an 87% yield.

A solution of 1.3M s-BuLi in cyclohexane (20.3 mL, 26.4 mmol) was added to an ether/liquid nitrogen cooled solution of N-ethyl-2-fluorobenzamide (2.00 g, 11.98 mmol) in THF (75 mL) and ether (75 mL), maintaining the internal reaction temperature ≦−95° C. The resulting mixture was stirred at this temperature for 30 min, then TMSCl (1.43 g, 13.2 mmol) was added and the mixture warmed to −60° C. After 2 h, the reaction was poured into water (200 mL). The organic layer was dried (MgSO$_4$), concentrated, and purified by silica gel chromatography, eluted with 3:7 ethyl acetate/hexanes, to afford 0.45 g of the title compound as a white solid, a 16% yield. m.p. 86–87° C.

EXAMPLE 118

1-[3-Fluoro-2,6-bis(trimethylsilyl)benzoyl]pyrrolidine

3-Fluorobenzoyl chloride was reacted with pyrrolidine using General Method E1 or E2 to produce N-(3-fluorobenzoyl)pyrrolidine.

A solution of 1.3M s-BuLi in cyclohexane (23.91 mL, 31.1 mmol) was added to an ether/liquid N$_2$ cooled (−90° C.) solution of TMEDA (3.97 g, 34.2 mmol) in THF (40 mL), followed by the addition of a solution of N-(3-fluorobenzoyl)pyrrolidine (5.0 g, 25.9 mmol) in a minimum volume of THF. The resulting reaction mixture was stirred at −90° C. for 15 min, then TMSCl (6.75 g, 62.2 mmol) was added in a single portion. The reaction was warmed to RT, quenched with dilute aq citric acid, then was extracted with ether (3×). The combined ether extracts were dried (MgSO$_4$), concentrated, and purified by HPLC with 3:7 EtOAc/hexanes to afford 0.45 g of the title compound as an oil, a 45% yield, which solidified on standing to a white solid. m.p. 97–100° C.

EXAMPLE 119

2-Chloro-N,N-diethyl-6-(trimethylgermyl)benzamide

A solution of 1.3M s-BuLi in cyclohexane (21.8 mL, 28.3 mmol) was added dropwise to a dry ice/acetone cooled solution of the compound of example e (4.6 g, 21.7 mmol) in THF (60 mL), maintaining the internal reaction temperature≦−65° C. This mixture was stirred at −78° C. for 45 min, then was quenched by the dropwise addition of a solution of trimethylchlorogermane (5.0 g, 32.6 mmol) in THF (30 mL), again maintaining the internal reaction temperature ≦−65° C. The reaction was warmed to 0° C., diluted with ether, and extracted with 10% HCl (2×) followed with sat aq NaHCO$_3$. The ether was dried (MgSO$_4$), concentrated, and purified by HPLC with 6% EtOAc in hexanes to afford 3.2 g of the title compound as a white solid, a 45% yield. m.p. 47–48° C.

EXAMPLE 120

2-Bromo-N-(2-methylphenyl)-6-(trimethylsilyl) benzamide

The compound of Example c (0.0035 mol, 0.95 g), 15 mL thionyl chloride, and 1 drop of DMF were combined and stirred at RT overnight. Toluene (50 mL) was added and the mixture concentrated to dryness. This process was repeated three times, and the residue dissolved in CH$_2$Cl$_2$ (50 mL). 2-Methylaniline (0.0035 mol, 0.37 g) and triethylamine (0.0035 mol, 0.39 g) were added and the mixture was stirred at RT overnight. The mixture was washed with 10% HCl and twice with water; dried (MgSO$_4$) and concentrated. The title compound was recrystallized from hexanes as a tan solid in 71% yield. m.p. 113–115° C.

EXAMPLE 121

N-(2-Methylphenyl)-2-(trimethylsilyl)benzamide

The compound of Example 120 (0.0021 mol, 0.75 g) and 50 mL THF were cooled to −78° C. in a nitrogen atmosphere with magnetic stirring. 1.3M s-BuLi (0.0026 mol, 2 mL) in cyclohexane was added dropwise. After stirring for 30 min, 25 mL of 25% citric acid were added. The mixture was then extracted three times with ethyl acetate, the extracts combined and washed with brine and twice with water, dried (MgSO$_4$) and concentrated. The title compound was recrystallized as a white solid from ethyl acetate/hexanes in 54% yield. m.p. 117–119° C.

EXAMPLE 122

2-Chloro-N-ethyl-6-(2-naphthalenyl)benzamide

The title compound was prepared by treatment of 2-bromonaphthalene (0.76 g, 3.65 mmol) according to General Method D. It was obtained as 0.68 g of a white solid, a 60% yield. m.p. 182–184° C.

EXAMPLE 123

N-Ethyl-2-fluoro-6-(1-methylcyclopentyl)benzamide

To lithium sand (0.44 g, 63.0 mmol) in THF (100 mL) at 0° C. under argon was added 4,4'-di-tert-butylbiphenyl (13.27 g, 51.0 mmol) and the resulting mixture was stirred at 0° C. overnight. The mixture was then cooled to −78° C. and 1-chloro-1-methylcyclopentane (3.0 g, 25.3 mmol) in THF (25 mL) was added. [1-Chloro-1-methylcyclopentane, a clear oil with b.p. 87–88° C./15T was obtained by the chlorination of 1-methylcyclopentanol with HCl gas.] This mixture was stirred for 15 min and the compound of Example g (5.34 g, 25.3 mmol) was added. The resulting solution was stirred at −78° C. for 1 h before being poured into water (250 mL). The aq layer was extracted three times with ether, and the combined extracts were dried (MgSO$_4$) and concentrated to yield 2-[2-fluoro-6-(1-methylcyclopentyl)phenyl]-4,5-dihydro-4,4-dimethyloxazole, as a clear oil in 40% yield. This oxazoline was carried through Steps 1–4 of Example 90. The resulting final product was recrystallized from ether/hexanes and obtained as a white solid. m.p. 116–117° C.

EXAMPLE 124

N-Ethyl-3-(trimethylsilyl)-4-pyridinecarboxamide

A solution of 4-pyridinecarboxylic acid (20 g, 0.16 mol) in 60 mL thionyl chloride was stirred at RT for 24 h. After that, excess thionyl chloride was removed in vacuo. The solid residue was added in portions to a mixture of 60 g of 70% ethylamine in water and 200 mL CH$_2$Cl$_2$ at −5° C. and then stirred at RT for 18 h. Water was added. The organic solution was separated, washed with water, brine, dried and concentrated to give 9.5 g of the crude N-ethyl-4-pyridinecarboxamide.

A solution of N-ethyl-4-pyridinecarboxamide in THF was metallated with lithium diisopropylamide (prepared from diisopropyl amine and 2.5M n-BuLi in hexane according to the method of Example 250) and quenched with TMSCl as in step c of Example 248. The title compound was purified by flash chromatography first with 20%, and then 70% ethyl acetate-hexane as eluent and recovered as a white solid. m.p. 93–95° C.

EXAMPLE 125

2-Chloro-N-ethyl-N-(2-furylmethyl)-6-(trimethylsilyl)benzamide

A 1.0M THF solution of sodium bis(trimethylsilyl)amide (7.7 mL, 7.7 mmol) was added dropwise to a solution of the compound of Example 32 (2.15 g, 7.0 mmol) in THF (30 mL). After stirring 1 h, a solution of ethyl iodide (1.31 g, 8.4 mmol) in THF (15 mL) was added. The resulting reaction was stirred overnight at RT, then was partitioned between ethyl acetate and dilute aq citric acid. The organic solution was washed twice with sat aq NaHCO$_3$ and then twice with brine, then was dried (MgSO$_4$) and concentrated to afford 1.8 g of the title compound as an amber oil, a 77% yield.

EXAMPLE 126

2-Chloro-N,N-bis(1-methylethyl)-6-(trimethylsilyl) benzamide

The compound of Example b (2.47 g, 10 mmol), diisopropyl amine (2.23 g, 22 mmol), and toluene (25 mL) were combined according to General Method E2. The crude product was recrystallized from ethanol/water to afford 1.75 g of the title compound as a white solid, a 58% yield. m.p. 96–97.5° C.

EXAMPLE 127

N-Ethyl-N-(methoxymethyl)-2-methyl-6-(trimethylsilyl)benzamide

The compound of Example 50 (1.33 g, 5.0 mmol) and MeI (2.8 g, 20 mmol) were combined according to General Method B. The resulting reaction was partitioned between ethyl acetate and sat aq NaHCO$_3$. The organic phase was washed with brine, dried (MgSO$_4$), and concentrated to afford a quantitative yield of the title compound as an oil.

EXAMPLE 128

2-Chloro-N-(2-ethoxyethyl)-N-ethyl-6-(trimethylsilyl)benzamide

The compound of Example b (4.94 g, 20 mmol), 2-ethoxyethyl amine (3.92 g, 44 mmol), and toluene (35 mL)

were combined according to General Method E1. The crude product was recrystallized from aq ethanol to afford 3.97 g of N-(2-ethoxyethyl)-2-chloro-6-(trimethylsilyl)benzamide as white solid, a 66% yield. m.p. 71–73° C.

A 1M THF solution of sodium bis(trimethylsilyl)amide (7.7 mL, 7.7 mmol) was added dropwise over 5 min to a solution of N-(2-ethoxyethyl)-2-chloro-6-(trimethylsilyl)benzamide (2.1 g, 7 mmol) in THF (30 mL). The resulting mixture was stirred for 1 h at RT, then a solution of ethyl iodide (1.31 g, 8.4 mmol) in THF (15 mL) was added with a mild exotherm. The resulting reaction mixture was stirred overnight, then was partitioned between ethyl acetate and dilute aq citric acid. The ethyl acetate phase was washed with sat aq NaHCO$_3$ followed with brine, then was dried (MgSO$_4$) and concentrated to afford 1.9 g of the title compound as an amber oil, an 83% yield.

EXAMPLES 129–134 AND 144–163

The following examples were prepared by reaction of the compound of Example b and the appropriate amine by General Method E1. Melting points are reported in ° C.

| Ex. No. | Compound Name | M.P. |
|---|---|---|
| 129 | 2-Chloro-N-cyclohexyl-6-(trimethylsilyl)benzamide | 198.5–200.5 |
| 130 | N-[2-Chloro-6-(trimethylsilyl)benzoyl]-2,6-dimethylmorpholine | — |
| 131 | N-[2-Chloro-6-(trimethylsilyl)benzoyl]-2,6-dimethylpiperidine | 187.5–190 |
| 132 | N-[2-Chloro-6-(trimethylsilyl)benzoyl]-morpholine | 110–111.5 |
| 133 | N-[2-Chloro-6-(trimethylsilyl)benzoyl]-4-methylpiperazine | 76–77.5 |
| 134 | N-[2-Chloro-6-(trimethylsilyl)benzoyl]-piperidine | 111–113 |

EXAMPLES 135–142

The following examples were prepared by reaction of the compound of Example b and the appropriate amine in dioxane in the presence of a slight molar excess of triethyl amine using the amination methods described above. The melting points are reported in ° C.

| Ex. No. | Compound Name | M.P. |
|---|---|---|
| 135 | 2-Chloro-N-(2-pyridinylmethyl)-6-(trimethylsilyl)benzamide | 84–88 |
| 136 | 2-Chloro-N-[(4-methoxyphenyl)methyl]-6-(trimethylsilyl)benzamide | 100–103 |
| 137 | 2-Chloro-N-[(4-nitrophenyl)methyl]-6-(trimethylsilyl)benzamide | 131–135 |
| 138 | 2-Chloro-N-(2-thienylmethyl)-6-(trimethylsilyl)benzamide | 120–122 |
| 139 | 2-Chloro-N-[(3-methoxyphenyl)methyl]-6-(trimethylsilyl)benzamide | 85–87 |
| 140 | 2-Chloro-N-[(3,4,5-trimethoxyphenyl)methyl]-6-(trimethylsilyl)benzamide | 128–130 |

-continued

| Ex. No. | Compound Name | M.P. |
|---|---|---|
| 141 | 2-Chloro-N-[(3-nitrophenyl)methyl]-6-(trimethylsilyl)benzamide | 121–122 |
| 142 | 2-Chloro-N-(cyanomethyl)-6-(trimethylsilyl)benzamide | 145–147 |
| 144 | N-(1,3-benzodioxol-5-ylmethyl)-2-chloro-6-(trimethylsilyl)benzamide | 138–140 |
| 145 | 2-Chloro-N-(4-pyridinylmethyl)-6-(trimethylsilyl)benzamide | 122–125 |
| 146 | 2-Chloro-N-(2-methoxyethyl)-6-(trimethylsilyl)benzamide | 75–77 |
| 147 | 2-Chloro-N-(2-methyl-2-propenyl)-6-(trimethylsilyl)benzamide | 118–121 |
| 148 | 1-[2-Chloro-6-(trimethylsilyl)benzoyl]-1,2,3,6-(tetrahydro)pyridine | 109–111 |
| 149 | 1-[2-Chloro-6-(trimethylsilyl)benzoyl]-2,5-dihydro-2,5-dimethyl-1H-pyrrole | 75–77 |
| 150 | 2-Chloro-N-(cyclopropylmethyl)-6-(trimethylsilyl)benzamide | 99–101 |
| 151 | 2-Chloro-N-(1-methylpropyl)-6-(trimethylsilyl)benzamide, (r)- | 148–149 |
| 152 | 2-Chloro-N-(1-methylpropyl)-6-(trimethylsilyl)benzamide, (s)- | 149–150 |
| 153 | N-(2-Bromoethyl)-2-chloro-6-(trimethylsilyl)benzamide | 101–103 |
| 154 | 2-Chloro-N-(2-hydroxy-1-methylethyl)-6-(trimethylsilyl)benzamide | 108–111 |
| 155 | 2-Chloro-N-(2-fluoroethyl)-6-(trimethylsilyl)benzamide | 103–105 |
| 156 | 2-Chloro-N-[2-(1-methylethyl)phenyl]-6-(trimethylsilyl)benzamide | 92–94 |
| 157 | 2-Chloro-N-(2-ethoxyphenyl)-6-(trimethylsilyl)benzamide | 73–76 |
| 158 | 2-Chloro-N-(2-cyclopentylphenyl)-6-(trimethylsilyl)benzamide | 110–113 |
| 159 | 2-Chloro-N-(2-methoxyphenyl)-6-(trimethylsilyl)benzamide | 75–76 |
| 160 | 2-Chloro-N-(2-nitrophenyl)-6-(trimethylsilyl)benzamide | 88–90 |
| 161 | 2-Chloro-N-(1-phenylethyl)-6-(trimethylsilyl)benzamide | 129–132 |
| 162 | 2-Chloro-N-(2-methylpropyl)-6-(trimethylsilyl)benzamide | 132–133 |
| 163 | 2-Chloro-N-cyclobutyl-6-(trimethylsilyl)benzamide | 145–146 |

EXAMPLE 143
N-Ethyl-N-(hydroxymethyl)-2-methyl-6-(trimethylsilyl)benzamide The compound of Example 127 (0.80 g, 2.9 mmol) was refluxed in a mixture of acetonitrile (20 mL) and 2N HCl (20 mL). Within 2 h the reaction was complete by GLC, and was cooled and partitioned between ether and water. The ether phase was concentrated and purified by RC with 1:4 ethyl acetate/hexanes, then recrystallized from hexanes to give 160 mg of the title compound as a solid, a 21% yield.

EXAMPLE 164
2-Chloro-N-methyl-N-(1-methylethyl)-6-(trimethylsilyl)benzamide Thionyl chloride (1.5 g, 12 mmol) was dissolved in 50 mL CH$_2$Cl$_2$ and the compound of Example 154 (dissolved in 50 mL CH$_2$Cl$_2$) was dropped in slowly. A drop of DMF was added and the mixture stirred overnight. Water was added and the mixture extracted with ethyl acetate to yield a solid which was recrystallized from 5% ethyl acetate/hexane. 2-Chloro-N-(2-chloro-1-methylethyl)-6-(trimethylsilyl) benzamide was obtained (2.2 g, 7.3 mmol, 73% yield). m.p. 150–151° C.

This compound (1.5 g, 5.0 mmol) was dissolved in 50 mL THF and 5.5 mL 1 M (in THF) potassium t-butoxide (5.5 mmol) was added. After standing 4 hrs, water was added the mixture extracted with ethyl acetate. Removal of solvent yielded an oil identified as 2-[2-chloro-6-(trimethylsilyl) phenyl]-4,5-dihydro-4-methyl-oxazole.

This compound (2.67 g, 10 mmol) and trimethyloxonium fluoroborate (1.5 g, 10 mmol) were dissolved in CH$_2$Cl$_2$ and allowed to stir 18 days. Ether was added to the mixture and the precipitate collected. The product, identified as 2-[2-chloro-6-(trimethylsilyl)phenyl]-4,5-dihydro-3,4-dimethyl-oxazolium tetrafluoroborate, was recrystallized by redissolving it in CH$_2$Cl$_2$ and adding ether to the cloud point. m.p. 155–157° C.

This compound (1.9 g, 5.1 mmol) and sodium cyanoborohydride (0.32 g) were added to methanol and stirred overnight. The mixture was filtered and water added to the mother liquor. Extraction with ethyl acetate yielded an oil upon solvent removal. The oil was dissolved in 50% ethyl acetate/hexane and filtered through silica gel. Removal of the solvent yielded an oil which was purified by RC (20% ethyl acetate/hexane).

EXAMPLE 165

2-Chloro-N-[(2-propenylamino)carbonyl]-6-(trimethylsilyl)benzamide

Silver cyanate (3.0 g, 20 mmol) which had been dried overnight at 140° was added to dry toluene followed by 2-chloro-6-trimethylsilylbenzoyl chloride (Example b) (2.46 g, 10 mmol). After refluxing 4 hrs, allyl amine (0.6 g, 10 mmol) is added and the mixture refluxed overnight. After filtration through silica gel to remove silver salts, the solvent was removed to yield an oil. Trituration with hexane produced 0.7 g of the title compound as a solid. m.p. 68–71° C.

EXAMPLE 166

2-Chloro-N,N-diethyl-6-[(trimethylsilyl)methyl]benzamide

The compound from example e (1.0 eq) and MeI (3.0 eq) were combined according to Method A. The crude product was purified by HPLC with 1:4 EtOAc/hexanes to give 5.2 g of N,N-diethyl 2-chloro-6-methylbenzamide as a yellow solid, a 92% yield. m.p. 48°–49° C.

This compound (1.0 eq) and TMSCl (2.0 eq) were combined according to Method A, and purified by HPLC with 1:9 EtOAc/hexanes to give 2.1 g of the title compound as a clear oil, a 59% yield.

EXAMPLE 167

2-Chloro-N-hydroxy-N-(1-methylethyl)-6-(trimethylsilyl)benzamide

The title compound was prepared by reaction of the compound of Example b and the i-propylhydroxylamine hydrochloride in dioxane in the presence of two equivalents of triethylamine using the amination methods described above. m.p. 175–179° C.

EXAMPLE 168

2-Chloro-N-hydroxy-N-(1-methylethyl)-6-(trimethylsilyl)benzamide, compd. with iron hydroxide (1:1)

The compound of Example 167 (0.47 g, 1.6 mmol) was added to 40 mL 0.5 M sodium acetate solution. Acetone was added to this suspension to a total of 80 mL. Slight warming yielded a homogeneous solution. Ferric chloride (0.44 g, 1.6 mmol), dissolved in 10 mL water, was added. A precipitate forms which seems to be colloidal in nature. Stripping of the acetone yielded a precipitate which could be easily filtered off and dried under vacuum overnight to yield 0.50 g of the title compound. m.p. 260° C.

EXAMPLE 169

2-Chloro-N-ethyl-6-(trimethylsilyl)benzenecarboximidothioic acid, ethyl ester

A solution of 9.66 g (36 mmol) of the compound of Example 76 and 40 mL trimethyloxonium tetrafluoroborate (1.0 M, 40 mmol) was allowed to stand overnight at RT. The mixture was stripped to 40 mL and 300 mL ether added to precipitate the product, which was identified as 9.5 g of N-[[2-chloro-6-(trimethylsilyl)phenyl](ethylthio)methylene]ethanamine (1:1) compound with tetrafluoroborate hydrate. m.p. 160–161° C.

To 3.87 g (10 mmol) of this compound in 100 mL CH$_2$Cl$_2$ was added 1.5 g (15 mmol) of triethyl amine. After standing a few minutes, the mixture was extracted with 100 mL water and the solvent removed to yield an oil. Purification was accomplished by RC (10% ethyl acetate/hexane) to yield 2.5 g of pure oil.

EXAMPLE 170

N-(1H-Benzotriazol-1-ylphenylmethyl)-2-chloro-6-(trimethylsilyl)benzamide

A mixture of 2-chloro-6-trimethylsilylbenzamide (2.27 g, 10 mmol), which may be readily prepared by the reaction of the compound of Example b and ammonium hydroxide, benzaldehyde (1.1 g, 10 mmol), and benzotriazole (1.2 g, 10 mmol) was refluxed 5 days in toluene utilizing a Dean-Stark trap to remove water. The solvent was removed to yield an oil which crystallizes. Recrystallization from ethyl acetate yielded 0.5 g of the title compound. m.p. 184–186° C.

EXAMPLE 171

2-Chloro-N-(2-chloro-1-methylethyl)-6-(trimethylsilyl)benzamide

This compound was prepared in the first step of Example 164. m.p. 150–151° C.

EXAMPLE 172

2-Chloro-N-ethyl-N-(methylthio)-6-(trimethylsilyl)benzamide

The compound of Example 45 (2.55 g, 10 mmol) was dissolved in 50 mL dry THF, and N-thiomethyl phthalimide (1.93 g, 10 mmol) was added followed by 12 mL of 1 M LiN(TMS)$_2$ (in THF) (12 mmol). All operations were carried out under nitrogen. After stirring at RT overnight gc/ms analysis suggested a mixture of the desired product and phthalimide. Water was added the mixture extracted with ethyl acetate. Removal of the solvent yielded a semisolid. Addition of 15% ethyl acetate/hexane generated a solid which was filtered off and discarded. The mother liquor was purified by RC (15% ethyl acetate/hexane) to yield 0.2 g.

EXAMPLE 173

2-Chloro-N-(isopropylaminocarbonyl)-6-(trimethylsilyl)benzamide

To 0.1 m of 2-chloro-6-(trimethylsilyl)benzamide, prepared by the reaction of the compound of Example b and ammonium hydroxide, in ethylene dichloride was added 1.2 eq oxalyl chloride and 2 drops of DMF. After refluxing overnight, the solvent is stripped off and the resulting oil Kugelrohred at 0.2 mm (87–92°) to yield 21 g (84%) of isocyanate. It is important to exclude moisture from the reaction; otherwise the primary amide is formed.

2-Chloro-6-trimethylsilylbenzoyl isocyanate (1.3 g, 5 mmol) was dissolved in 40 mL toluene and isopropyl amine (1 g) added over a period of 30 seconds. After stirring 30 min, the solvent was removed to yield an oil. The oil was dissolved in hexane and cooled in dry ice to yield 1.2 g of crystals of the title compound. m.p. 113–116° C.

EXAMPLE 174

2-Chloro-N-(methylthio)-6-(trimethylsilyl)benzamide

To 1.1 g of 2-chloro-6-(trimethylsilyl)benzamide, prepared from Example b and ammonium hydroxide, (5 mmol) in 50 mL THF was added 5.5 mL of 1 M (in THF) potassium t-butoxide (5.5 mmol) followed by 0.95 g N-thiomethylphthalimide (5 mmol). After standing overnight, gc/ms suggested close to a 50/50 mix of product to starting benzamide. Water was added and the mixture extracted with ethyl acetate. Removal of the solvent yielded a semisolid. Trituration with 50 mL 15% ethyl acetate/hexane yielded a solid which was filtered off and collected. The mother liquor was purified by RC (20% ethyl acetate/hexane). The first band was collected and stripped to an oil which crystallized upon trituration with hexane and to yield 0.3 g of the title compound. m.p. 92–94° C.

EXAMPLE 175

2,2,2-Trichloro-N-[2-chloro-6-(trimethylsilyl)phenyl]acetamide

To a solution of 53.0 g (215 mmol) of the compound of Example b in 500 mL acetone was added 15.3 g (235 mmol) sodium azide and 50 mL water. The mixture was stirred for 15 min and gas evolution began to subside. The mixture was then heated to reflux for 22 h. Acetone was then removed in vacuo and the residue was partitioned between ether and water. The organic layer was washed with brine, dried ($MgSO_4$) and was filtered through silica gel. The filtrate was evaporated in vacuo to yield 42.8 g (100%) of a colorless oil, identified as 2-(trimethylsilyl)-6-chloroaniline.

To a solution of 2.0 g (10.0 mmol) of this compound and 0.8 g (10.1 mmol) pyridine in 30 mL dry THF was added 1.82 g (10.0 mmol) trichloroacetyl chloride. The mixture was stirred at ambient for 4 h and was then partitioned between ether and water. The organic layer was washed with brine, dried ($MgSO_4$), and was filtered through silica gel. The filtrate was evaporated in vacuo and the residue was triturated in ether/hexane to yield the title compound as 2.9 g of white crystals. m.p. 188.5–189° C.

EXAMPLE 176

2-Bromo-N-ethyl-6-(trimethylsilyl)benzamide

The compound of Example d (38.19 g, 0.13 mol) was reacted with 70% aqueous ethylamine (53 mL) according to General Method E1 and recrystallized from methylcyclohexane to afford the title compound as light tan crystals in 92% yield. m.p. 121–122° C.

EXAMPLE 177

2-Chloro-N-ethyl-4-(trimethylsilyl)-3-thiophenecarboxamide

A mixture of 3-thiophenecarboxylic acid (20 g, 178 mmol), thionyl chloride (30 mL), and DMF (5 drops) was stirred overnight, then was concentrated under vacuum and stripped several times from toluene to remove all traces of excess thionyl chloride. Pyridine (31.64 g, 400 mmol) was added dropwise to a mixture of this acid chloride and ethylamine hydrochloride in toluene (5 mL) and $CH_2Cl_2$ (50 mL). After stirring for 1 h, the reaction was washed with 10% aq HCl followed with water, then was dried ($MgSO_4$), concentrated, and crystallized from ethyl acetate/hexanes to give 14.9 g of N-ethyl-3-thiophenecarboxamide as a tan solid, a 76% yield. m.p. 115°–117° C.

A solution of 1.3M s-BuLi in cyclohexane (44 mL, 57.2 mmol) was added dropwise to a –78° C. cooled solution of N-ethyl-3-thiophenecarboxamide (4.04 g, 26 mmol) and TMEDA (6.65 g, 57.2 mmol) in THF (100 mL). After stirring for 30 min at –78° C., a solution of hexachloroethane (13.54 g, 57.2 mmol) in THF (20 mL) was added dropwise. The resulting reaction mixture was warmed to RT over 1 h, quenched with dilute aq citric acid, and extracted with EtOAc (3×). The combined organic extracts were dried ($MgSO_4$), concentrated, and purified by HPLC with 3:7 EtOAc/hexanes to give 2.8 g of N-ethyl-2-chloro-3-thiophenecarboxamide as a yellow oil, a 57% yield.

A solution of 1.3M s-BuLi in cyclohexane (16.15 mL, 21 mmol) was added dropwise to an ether/liquid $N_2$ cooled (–100° C.) solution of N-ethyl-2-chloro-3-thiophenecarboxamide (1.90 g, 10 mmol) and TMEDA (3.17 mL, 21 mmol) in THF (100 mL). After stirring for 30 min at –100° C., TMSCl (2.28 g, 21 mmol) was added in a single portion. The resulting reaction mixture was warmed to –25° C. over 1 h, quenched with dilute aq citric acid, and extracted with EtOAc (3×). The combined organic extracts were dried ($MgSO_4$), concentrated, and purified by HPLC with 3:17 EtOAc/hexanes to afford 0.3 g of the title compound as a white solid, an 11% yield. m.p. 46–48° C.

EXAMPLE 178

N-Ethyl-2-(trimethylsilyl)-1H-pyrrole-1-carboxamide

60% NaH in mineral oil (1.8 g, 45 mmol) was added to an ice-water cooled solution of pyrrole (2.01 g, 30 mmol) in THF (100 mL) over a 15 min period. After 1 h, the reaction mixture was cooled to –78° C. and ethyl isocyanate (1.78 g, 25 mmol) was added. This mixture was allowed to warm to RT and stirred overnight, then was partitioned between ether and dilute aq citric acid. The ether phase was dried ($MgSO_4$), filtered through silica gel, concentrated, and recrystallized from ether/hexanes to give a 39% yield of pyrrole-1-(N-ethyl carboxamide).

1.3M s-BuLi in cyclohexane (18.5 mL, 24 mmol) was added dropwise to a dry-ice/acetone cooled solution of pyrrole-1-(N-ethyl carboxamide) (1.38 g, 10 mmol) and 2,2,6,6-tetramethylpiperidine (1.55 g, 11 mmol) in THF (50 mL). After stirring for 30 min at −78° C., TMSCl (1.63 g, 15 mmol) was added in a single portion. The reaction was allowed to slowly warm to Rt over 30 min, then was quenched with dilute aq citric acid and extracted with ethyl acetate (3×). The combined organic solutions were dried (MgSO$_4$), concentrated, and crystallized from ether/hexanes to give 0.8 g of the title compound as a white solid, a 38% yield. m.p. 100°–103° C.

EXAMPLE 179

2-Chloro-6-(dimethyl-2-propenylsilyl)-N-ethylbenzamide

A solution of 1.3M s-BuLi in cyclohexane (10.5 mL, 13.6 mmol) was added dropwise to a dry-ice/acetone cooled solution of TMEDA (1.0 mL, 6.5 mmol) in THF (10 mL), followed by the dropwise addition of a solution of the compound of example f (1.0 g, 5.45 mmol) in THF (10 mL). The reaction mixture was stirred at −78° C. for 30 min, then allyldimethylchlorosilane (10.9 mmol) was added and the mixture was stirred for 2.5 h at −78° C. The resulting reaction was warmed to −30° C., quenched with dilute aq citric acid, diluted with water, and extracted with EtOAc (2×). The combined organic extracts were dried (MgSO$_4$), concentrated, and purified by HPLC with 1:19 EtOAc/cyclohexane to give the desired compound as a white solid. m.p. 61–63° C.

EXAMPLE 180

2-Chloro-6-[dimethyl(1-methylethyl)silyl]-N-ethylbenzamide

The title compound was prepared as in Example 179 from isopropyldimethylchlorosilane in 62% yield. m.p. 98°–100° C.

EXAMPLE 181

2-Chloro-6-(cyclohexyldimethylsilyl)-N-ethylbenzamide

The title compound was prepared as in Example 179 from cyclohexyldimethylchlorosilane in 71% yield. m.p. 111–113° C.

EXAMPLE 182

2-Chloro-6-(dimethyloctylsilyl)-N-ethylbenzamide

The title compound was prepared as in Example 179 from octyldimethylchlorosilane in 78% yield. m.p. 62–63° C.

EXAMPLE 183

2-(Bicyclo[2.2.1]Hept-2-yldimethylsilyl)-6-chloro-N-ethylbenzamide

The title compound was prepared as in Example 179 from 2-bicycloheptyl dimethylchlorosilane in 58% yield. m.p. 124–125° C.

EXAMPLE 184

2-Chloro-6-(dimethylphenylsilyl)-N-ethylbenzamide

The title compound was prepared as in Example 179 from phenyldimethylchlorosilane in 44% yield. m.p. 89–91° C.

EXAMPLE 185

2-Chloro-6-[(1,1-dimethylethyl)dimethylsilyl]-N-ethylbenzamide

The title compound was prepared as in Example 179 from tert-butyldimethylchlorosilane in 28% yield. m.p. 140–142° C.

EXAMPLE 186

2-(1,1-Dimethylethyl)-N-ethyl-N-(1-methoxy-2,2-dimethylpropyl)benzamide

A mixture of 2-tert-butylbenzoic acid (15.7 g, 88.2 mmol) and thionyl chloride (19.3 mL, 265 mmol) was stirred at RT for 1 day, then was concentrated and stripped from toluene (2×) under vacuum. The compound from example k (19.94 g, 176.5 mmol) was added to a solution of this crude 2-tert-butylbenzoyl chloride in toluene (90 mL), and the mixture was heated at 100° C. for 3 h, then was stirred at room temperature overnight. The resulting mixture was cooled with an ice-water bath, and Et$_3$N (13.4 g, 132.4 mmol) was added, followed by the dropwise addition of methanol (5.65 g, 176.6 mmol). The resulting reaction mixture was stirred at RT and monitored to completion by GLC, then was partitioned between ether and sat aq NaHCO$_3$. The ether extract was dried (MgSO$_4$), concentrated, and purified by flash chromatography with 1:9 EtOAc/hexanes to afford 20.8 g of the title compound as a pale yellow oil, a 77% yield.

EXAMPLE 187

N-Ethyl-N-(1-methoxy-2,2-dimethylpropyl)-2-(trimethylsilyl)benzamide

A solution of the compound of Example k (30 g, 265 mmol) in CH$_2$Cl$_2$ (60 mL) was added to an ice-water cooled solution of benzoyl chloride (36 g, 256 mmol) in CH$_2$Cl$_2$ (180 mL). The cooling bath was then removed and a mild exotherm occurred. After 1 h the reaction was cooled with an ice-water bath, then Et$_3$N (4.44 g, 43.9 mmol) was added in a single portion, followed by the dropwise addition of methanol (2.55 g, 79.7 mmol) with formation of a precipitate. The resulting reaction was stirred at RT for 30 min, then was partitioned between ether and sat aq NaHCO$_3$. The ether phase was dried (MgSO$_4$), concentrated, and kugelrohr distilled under vacuum to afford 61.23 g of pure N-ethyl-N-(1-methoxy-2,2-dimethylpropyl)benzamide as an oil, a 96% yield.

A solution of 1.3M s-BuLi in cyclohexane (140.6 mL, 182.8 mmol) was added dropwise to a dry-ice/acetone cooled solution of N-ethyl-N-(1-methoxy-2,2-dimethylpropyl)benzamide (35 g, 140.6 mmol) and TMEDA (25.44 mL, 168.6 mmol) in THF (280 mL), maintaining the internal reaction temperature ≦−60° C. The yellow solution was stirred at −78° C. for 1 h, then was cannulated into a dry-ice/acetone cooled solution of TMSCl (26.72 mL, 210.6 mmol) in THF (140 mL) at a rate which maintained the internal reaction temperature ≦−55° C. The resulting mixture was warmed to 0° C. and partitioned between ether and sat aq NaHCO$_3$. The ether solution was dried (MgSO$_4$), concentrated, and kugelrohr distilled under vacuum to give 44.8 g of the title compound as a pale yellow solid, a 99% yield. m.p. 76–78° C.

EXAMPLE 188

2-[(1,1-Dimethylethyl)methylamino]-N-ethylbenzamide

70% Perchloric acid (22.5 g, 157 mmol) was added dropwise to an ice-water cooled solution of anthranil (9.53 g, 80 mmol) and tertiary butanol (5.93 g, 80 mmol). The resulting mixture was stirred at Rt overnight, then was diluted with ether to form a slurry. The solid was collected by filtration and dried under vacuum to afford 16.0 g of N-tert butyl anthranilium perchlorate as a white solid.

N-tert butyl anthranilium perchlorate (15.6 g, 56.6 mmol) was added in portions to a solution of triethylamine (17.2 g, 170 mmol) in $CH_2Cl_2$ (150 mL). The mixture was stirred at Rt for 1 h, then was concentrated to a small volume, triturated with ether, and filtered to remove the salts. The filtrate was concentrated and vacuum distilled to give 1.8 g of the N-tert butyl b-lactam as a yellow oil. b.p. 89°–90° C. at 0.2 Torr.

This N-tert butyl b-lactam 0.52 g, 3 mmol) was added to a solution of 70% aq $EtNH_2$ (0.58 g, 9 mmol) and $CH_2Cl_2$ (50 mL). After stirring for 3d at RT the mixture was concentrated and crystallized from hexanes to afford 0.61 g of N-ethyl 2-(N-tert butylamino)benzamide as a white solid. m.p. 37°–40° C.

A mixture of this material, potassium carbonate (0.4 g, 2.86 mmol), and methyl iodide (0.45 g, 3.15 mmol) in DMF (10 mL) was stirred at RT overnight, then was partitioned between ether and water. The ether was dried ($MgSO_4$), concentrated, and purified by RC with 3:7 ethyl acetate/hexanes, followed by recrystallization from hexanes to afford 100 mg of the title compound as a white solid. m.p. 45°–48° C.

EXAMPLE 189

2-Chloro-6-[(1,1-dimethylethyl)methylamino]-N-ethyl-N-methylbenzamide

A solution of the N-tert-butyl b-lactam (1.1 g, 6.3 mmol) described in the preparation of Example 188, and N-ethyl-N-methylamine (1.2 g, 20.8 mmol) in $CH_2Cl_2$ (50 mL) was stirred at RT overnight. The solvent was evaporated and the residue purified by RC with EtOAc/cyclohexane to give 1.277 g of N-ethyl-N-methyl 2-(N-tert-butylamino) benzamide as an orange oil, an 86% yield.

A mixture of N-ethyl-N-methyl 2-(N-tert-butylamino) benzamide (1.89 g, 8.1 mmol), potassium carbonate (2.2 g, 15.9 mmol), and methyl iodide (2.3 g, 16.2 mmol) in DMF (40 mL) was heated overnight at 40° C., then was partitioned between EtOAc and water. The EtOAc was dried ($MgSO_4$), concentrated, and purified by HPLC with 1:4 ethyl acetate/cyclohexane to afford 1.923 g of N-ethyl-N-methyl 2-(N-methyl-N-tert-butylamino)benzamide as a yellow oil, a 96% yield.

A solution of 1.3M s-BuLi in cyclohexane (3.7 mL, 4.8 mmol) was added dropwise to a dry-ice/acetone cooled solution of TMEDA (0.7 mL, 4.8 mmol) in THF (10 mL), followed by the dropwise addition of a solution of N-ethyl-N-methyl 2-(N-methyl-N-tert-butylamino)benzamide (1.0 g, 4.0 mmol) in THF (5 mL). The reaction mixture was briefly warmed to –30° C., then cooled to –78° C. and stirred for 15 min. A solution of hexachloroethane (2.8 g, 12.1 mmol) in THF (5 mL) was added. This mixture was stirred for 1 h at –78° C., then was warmed to –30° C., diluted with water, and extracted with EtOAc (2×). The combined organic extracts were dried ($MgSO_4$), concentrated, and purified by HPLC with 1:4 EtOAc/cyclohexane to give 528 mg of the title compound as a yellow oil, a 46% yield.

EXAMPLE 190

2-Chloro-6-[(1,1-dimethylethyl)methylamino]-N-ethylbenzamide

A solution of 1.3M s-BuLi in cyclohexane (5.7 mL, 7.5 mmol) was added dropwise to a dry-ice/acetone cooled solution of TMEDA (0.5 mL, 3.6 mmol) in THF (10 mL), followed by the dropwise addition of a solution of the compound of Example 188 (0.7 g, 3.0 mmol) in THF (5 mL). The reaction mixture was stirred at –78° C. for 30 min, then hexachloroethane (2.1 g, 9.0 mmol) in THF (5 mL) was added. This mixture was stirred for 30 min at –78° C., then was warmed to –30° C., diluted with water, and extracted with EtOAc (2×). The combined organic extracts were dried ($MgSO_4$), concentrated, and purified by HPLC with 3:17 EtOAc/cyclohexane to give 495 mg of the title compound as a yellow solid, an 61% yield. m.p. 106°–108° C.

EXAMPLE 191

N-Ethyl-2-[(1,1-dimethylethyl)methylamino]-6-methylbenzamide

A solution of 1.3M s-BuLi in cyclohexane (9.8 mL, 12.8 mmol) was added dropwise to a dry-ice/acetone cooled solution of TMEDA (0.6 mL, 3.8 mmol) in THF (10 mL), followed by the dropwise addition of a solution of the compound of Example 188 (0.75 g, 3.2 mmol) in THF (5 mL). The reaction mixture was stirred at –78° C. for 30 min, then methyl iodide (2.3 g, 16 mmol) was introduced in a single portion. This mixture was stirred for 2.5 h at –78° C., then was warmed to –30° C., diluted with water, and extracted with EtOAc (2×). The combined organic extracts were dried ($MgSO_4$), concentrated, and purified by HPLC with 1:4 EtOAc/cyclohexane to give 146 mg of the title compound as a light yellow solid, an 18% yield. m.p. 101–103° C.

EXAMPLE 192

2-Chloro-6-[(1,1-dimethylethyl)amino]-N-ethylbenzamide

A mixture of 2-chloro-6-fluorobenzaldehyde (99.1 g, 625 mmol) and $NaN_3$ (81.2 g, 1249 mmol) in DMSO (900 mL) was slowly heated to 75° C. for 2 h. The reaction temperature was then raised to 100° C. and the formation of the chloroanthranil was monitored to completion over about 3 h by $^1$H-NMR analysis of the aromatic region. The dark solution was partitioned between water (2 liters) and ether, then filtered through celite to break up the emulsion. The aq layer was extracted with additional ether, then the combined organic extracts were washed with water, dried ($MgSO_4$), concentrated, and kugelrohr distilled to give 81.65 g of the chloroanthranil as a light yellow solid, an 85% yield. m.p. 45°–47° C.

A mixture of this chloroanthranil (81.65 g, 532 mmol) and tert-butanol (43.4 g, 586 mmol) was warmed to effect solution, then was cooled in an ice-water bath while 70% perchloric acid was added at a rate which maintained the internal reaction temperature ≦35° C. After addition, the cold bath was removed and the reaction mixture continued to exotherm for ¯1 h while a precipitate formed. After 2 h the resulting mixture was cooled with an ice-water bath and slurried in ether (100 mL). The salts were collected by filtration, washed with dry ether, and dried under vacuum to give 155.91 g of the N-tert-butyl chloroanthranilium perchlorate salt as a pale yellow solid, a 95% yield.

This N-tert-butyl chloroanthranilium perchlorate salt (155.91 g, 503 mmol) was added in portions, via Gooch tubing, to an ice-water cooled solution of $Et_3N$ (152.7 g, 1509 mmol) in $CH_2Cl_2$ (1 liter). The resulting amber solution was stirred at RT for 30 min, then was concentrated to a small volume, diluted with dry ether (500 mL), filtered to remove the salts, and concentrated to give 101.11 g of desired b-lactam as a golden oil, a 96% yield.

A solution of this b-lactam (101.11 g, 483 mmol) in ether (100 mL) was added dropwise to an ice-water cooled solution of aq 70% $EtNH_2$ (465 g, 7233 mmol), maintaining the internal reaction temperature ≦20° C. The resulting mixture was stirred at RT for 30 min, then was diluted with water and extracted with ether (3×). The combined organic extracts were dried ($MgSO_4$), concentrated to a small volume, then slurried in hexanes (1 liter) and filtered to give 111.75 g of the title compound as a white solid, a 91% yield. m.p. 139–140° C.

EXAMPLE 193

2-Chloro-N-ethyl-4-formyl-6-(trimethylsilyl) benzamide

A mixture of 2-chloro-4-bromobenzoic acid (5.0 g, 21.2 mmol) and hexamethyldisilazane (5.0 mL, 23.7 mmol) was heated at 135° C. for 3 h, then was distilled under vacuum to afford 6.32 g of O-trimethylsilyl 2-chloro-4-bromobenzoate as a colorless oil, a 97% yield.

A solution of 2.5M n-BuLi in hexanes (3.25 mL, 8.13 mmol) was added to a dry-ice/acetone cooled solution of 2,2,6,6-tetramethylpiperidine (1.20 g, 8.5 mmol) in THF (6 mL). This solution was stirred at −78° C. for 15 min, then was cooled to −100° C. with ether/liquid $N_2$, and a solution of O-trimethylsilyl 2-chloro-4-bromobenzoate (2.00 g, 6.5 mmol) in THF (6 mL) was added slowly dropwise, maintaining the internal reaction temperature ≦−95° C. The resulting reaction mixture was stirred at −100° C. for 15 min, then was poured into dilute aq citric acid and extracted with ether (2×). The combined organic extracts were dried ($MgSO_4$), and concentrated to give crude 2-chloro-4-bromo-6-trimethylsilylbenzoic acid as a golden oil.

The 2-chloro-4-bromo-6-trimethylsilylbenzoic acid was diluted with thionyl chloride (3 mL, 41.1 mmol) and warmed. When gas evolution ceased, the solution was concentrated and stripped from toluene (2×) under vacuum to remove the excess thionyl chloride. The remaining dark oil was dissolved in toluene (12 mL), then the compound from example k (2.2 g, 19.5 mmol) was added and the mixture was heated at 100° C. until the reaction was complete by GLC. The resulting mixture was cooled to 0° C., and $Et_3N$ (1.32 g, 13.0 mmol) was added in a single portion, followed by the dropwise addition of methanol (0.62 g, 19.4 mmol) in toluene (1 mL). The reaction was warmed to RT and monitored to completion by GLC, then was diluted with ether and extracted with sat aq $NaHCO_3$, dried ($MgSO_4$), concentrated, and the residue dissolved in hexanes. The hexane solution was cooled to −78° C. and filtered to remove insoluble impurities, then the filtrate was concentrated and purified by RC with 1:49 EtOAc/hexanes to give 820 mg of N-ethyl-N-(1-methoxy-2,2-dimethylpropyl)-2-chloro-4-bromo-6-(trimethylsilyl) benzamide as a yellow oil.

A solution of N-ethyl-N-(1-methoxy-2,2-dimethylpropyl)-2-chloro-4-bromo-6-(trimethylsilyl) benzamide (820 mg, 1.89 mmol) in THF (2 mL) was added dropwise to a dry-ice/acetone cooled solution of 2.5M n-BuLi in hexanes (1 mL, 2.5 mmol) in THF (2 mL). The resulting red solution was stirred at −78° C. for 15 min, then DMF (500 mL, 6.5 mmol) was added in a single portion. After 5 min, the reaction was poured into sat aq $NaHCO_3$ and extracted with ether (2×). The combined organic extracts were dried ($MgSO_4$) and concentrated, then a solution of this protected amide in acetone (5 mL) was charged with 6N HCl and stirred overnight at RT. The resulting mixture was poured into sat aq $NaHCO_3$ and extracted with ether (2×), then the combined organic extracts were dried ($MgSO_4$), concentrated, and purified by RC with 3:7 EtOAc/hexanes to give 220 mg of the title compound as a white solid, a 40% yield. m.p. 95–97° C.

EXAMPLE 194

2[(1,1-Dimethylethyl)sulfinyl]-N-ethyl-6-fluorobenzamide

A mixture of 2-methyl-2-propanethiol (2.7 g, 30 mmol), the compound of example g (3.17 g, 15 mmol), and NaH (0.79 g, 33 mmol) in THF (100 mL) was stirred at RT for 1d, then at reflux for 1d. This was then quenched with sat aq $NaHCO_3$ (50 mL) and extracted with EtOAc (3×50 mL). The combined organic extracts were dried ($MgSO_4$), concentrated, and purified by HPLC with 1:4 EtOAc/hexanes to afford 3.5 g of 2-[2-fluoro-6-(1,1-dimethylethylthio)phenyl]-4,4-dimethyl-2-oxazoline as a yellow oil, an 83% yield.

Following the procedure of example 6, 2-[2-fluoro-6-(1,1-dimethylethylthio)phenyl]-4,4-dimethyl-2-oxazoline (3.5 g, 12.5 mmol) was converted to N-ethyl-2-fluoro-6-(1,1-dimethylethylthio)benzamide as a white solid. m.p 107–109° C.

A 0° C. solution of N-ethyl-2-fluoro-6-(1,1-dimethylethylthio)benzamide (3.45 g, 13.51 mmol) in methanol (100 mL) was combined with a 0° C. solution of OXONE® (8.31 g, 13.51 mmol) in water (100 mL). This mixture was stirred for 2 min, then was poured into 25% aq sodium metabisulfite (100 mL) and extracted with ether (3×100 mL). The combined organics were washed with brine followed with water, then was dried ($MgSO_4$), concentrated, and recrystallized from ethyl acetate-hexanes to afford 2.2 g of the title compound as a white solid, a 60% yield. m.p. 114–116° C.

EXAMPLE 195

N,N-Diethyl 2-[(1,1-dimethylethyl)sulfinyl]-6-fluorobenzamide

The title compound was prepared in an analogous procedure to Example 194, and purified by RC with 1:1 ethyl acetate/hexanes to give a green oil.

EXAMPLE 196

N-(1-Methylethyl)-2-[(1,1-dimethylethyl)sulfinyl]-6-fluorobenzamide

The title compound was prepared in an analogous procedure to Example 194, and purified by recrystallization from ether/hexanes to give a white solid. m.p. 120–135° C.

EXAMPLE 197

N-(2-Chloroethyl)-2-fluoro-6-(2-methylphenyl) benzamide

A 2.5M solution of n-BuLi in cyclohexane (6.4 mL, 16 mmol) was added dropwise to an ether/liquid $N_2$ cooled solution of 2-bromotoluene (2.74 g, 16 mmol) in THF (100 mL), maintaining the internal reaction temperature ≦−85° C. The resulting solution was cannulated into an ether/liquid $N_2$ cooled solution of the compound of example j (2.93 g, 16 mmol) in THF (25 mL). The resulting mixture was warmed to −60° C. and poured to sat aq NaHCO$_3$, then was extracted with ether (3×100 mL). The combined organic extracts were washed with water (2×25 mL), dried (MgSO$_4$), concentrated, then purified by HPLC with 3:7 EtOAc/hexanes to afford 3.2 g of 2-[2-fluoro-6-(2-methylphenyl)]-2-oxazoline as a white solid, a 78% yield. m.p. 65–68° C.

Excess HCl gas was bubbled into a solution of 2-[2-fluoro-6-(2-methylphenyl)]-2-oxazoline (3.2 g, 12.5 mmol) in ether (50 mL). The resulting mixture was allowed to stir overnight, then was crystallized by the addition of hexanes to afford 2.4 g of the title compound as a white solid, a 51% yield. m.p. 78–81° C.

EXAMPLE 198

N-(2-Chloroethyl)-2-[(1,1-dimethylethyl)sulfinyl]-6-fluorobenzamide

LiH (0.12 g, 16 mmol) was carefully added to a solution of 1,1-dimethylethanethiol (1.44 g, 16 mmol) in THF (100 ml). When gas evolution ceased, the compound of example j (2.93 g, 16 mmol) was added in a single portion. The mixture refluxed overnight, then was cooled and partitioned between ether and sat aq NaHCO$_3$. The ether was dried (MgSO$_4$) and concentrated, then was dissolved in ether and excess HCl gas added. The resulting mixture was allowed to stir overnight, then was crystallized by the addition of hexanes to afford 2.2 g of N-(2-chloroethyl)-2-fluoro-6-(1,1-dimethylethylthio)benzamide as a white solid, a 47% yield.

A 0° C. solution of N-(2-chloroethyl)-2-fluoro-6-(1,1-dimethylethylthio)benzamide (2.0 g, 7.0 mmol) in methanol (50 mL) was combined with a 0° C. solution of OXONE® (4.24 g, 7.0 mmol) in water (50 mL). This mixture was stirred for 2 min, then was poured into 25% aq sodium metabisulfite (100 mL) and extracted with ether (3×100 mL). The combined organics were washed with brine followed with water, then were dried (MgSO$_4$), concentrated, and purified by HPLC with 7:3 ethyl acetate/hexanes to afford 2.1 g of the title compound as a white solid, a 98% yield. m.p. 80–90° C.

EXAMPLE 199

N-(2-Chloroethyl)-2-fluoro-6-(1-methylcyclobutyl) benzamide

An 0.2M solution of lithium 4,4'-(di-t-butyl)biphenyl (50 mL, 10 mmol) was added to a dry ice/acetone cooled solution of 1-chloro-1-methylcyclobutane (1.04 g, 10 mmol) in THF (25 mL), maintaining the internal reaction temperature ≦−55° C. The resulting mixture was stirred at −78° C. for 30 min, then the compound of example j (1.65 g, 9 mmol) was added in a single portion. After 1 h at −78° C., the reaction was poured into sat aq NaHCO$_3$ (50 mL) and extracted with ether (3×50 mL). The combined organics were washed with water, dried (MgSO$_4$), concentrated, and purified by RC to afford 0.8 g of 2-[2-fluoro-6-(1-methylcyclobutyl)]-2-oxazoline as a colorless oil, a 34% yield. Excess HCl gas was bubbled into a solution of this oxazoline in ether. The resulting mixture was allowed to stir overnight, then was crystallized by the addition of hexanes to afford 0.5 g of N-(2-chloroethyl)- 2-fluoro-6-(1-methylcyclobutyl)benzamide as a white solid, a 62% yield. m.p. 108–110° C.

EXAMPLE 200

3,6-Dichloro-N-ethyl-2-(trimethylsilyl)benzamide 2,5-Dichlorobenzoyl chloride (51 mmol) and 70% aq EtNH$_2$ (130 mmol) were combined according to General Method E1 to afford 9.4 g of N-ethyl-2,5-dichlorobenzamide as a beige solid, an 85% yield.

A solution of 1.5M LDA in THF (13 mL, 19.5 mmol) was added dropwise to an ether/liquid N$_2$ cooled solution of N-ethyl 2,5-dichlorobenzamide (2.0 g, 9.2 mmol) and TMSCl (1.5 mL, 11.5 mmol) in THF (50 mL), maintaining the internal reaction temperature ≦−80° C. The resulting reaction mixture was stirred at −100° C. for 30 min, then was partitioned between ether and sat aq NaHCO$_3$. The ether solution was dried (MgSO$_4$), concentrated, and crystallized from EtOAc/hexanes to afford 1.15 g of the title compound as a white solid. m.p. 150–153° C.

EXAMPLE 201

2-Chloro-N-ethyl-N-(1-methoxy-2,2-dimethylpropyl)-6-(trimethylsilyl)benzamide

A solution of the compound of Example k (3.55 g, 31.4 mmol) in CH$_2$Cl$_2$ (10 mL) was added dropwise to an ice-water cooled solution of 2-chlorobenzoyl chloride (5.0 g, 28.6 mmol) in CH$_2$Cl$_2$ (20 mL). The reaction was warmed to RT and exothermed for 10–15 min. The resulting solution was cooled with an ice-water bath and Et$_3$N (3.0 g, 29.6 mmol) was syringed in, followed by the dropwise addition of MeOH (1.83 g, 57.2 mmol). The reaction was allowed to warm to RT and monitored to completion by GLC, then was diluted with ether and extracted with sat aq NaHCO$_3$, dried (MgSO$_4$), concentrated, and kugelrohr distilled under vacuum to afford 7.54 g of N-ethyl-N-(1-methoxy-2,2-dimethylpropyl)-2-chlorobenzamide as a colorless oil, a 93% yield.

A solution of 1.3M s-BuLi in cyclohexane (3.53 mL, 4.59 mmol) was added to a dry ice/acetone cooled solution of TMEDA (639 mL, 4.23 mmol) and N-ethyl-N-(1-methoxy-2,2-dimethylpropyl)-2-chlorobenzamide (1.0 g, 3.53 mmol) in THF (7 mL). The resulting mixture was stirred at −78° C. for 45 min, then TMSCl (671 mL, 5.29 mmol) was added in a single portion. The reaction was allowed to warm to 0° C., and partitioned between ether and 10% HCl The ether solution was then extracted with sat aq NaHCO$_3$, dried (MgSO$_4$), and purified by RC with 1:49 EtOAc/hexanes to afford 750 mg of the title compound as a white solid, a 60% yield. m.p. 82–83° C.

EXAMPLE 202

2-Chloro-6-(ethenylmethylphenylsilyl)-N-ethylbenzamide

A 1.3M solution of s-BuLi in cyclohexane (10.5 mL, 13.6 mmol) was added to a dry ice/acetone cooled solution of TMEDA (1 mL, 6.5 mmol) in THF (10 mL), followed by the dropwise addition of the compound of example f (1.0 g, 5.45 mmol) in THF (10 mL). Phenyl methyl vinyl chlorosilane (1.5 g, 8.2 mmol) was added after 30 min, and the mixture was stirred at −78° C. for 2 h. This was poured into 25% aq citric acid and partitioned between EtOAc and water. The EtOAc was dried (MgSO$_4$), concentrated, and purified by HPLC with 1:19 EtOAc/cyclohexane to afford 0.56 g of a white solid which was recrystallized from EtOAc/petroleum ether at low temperature to give 0.194 g of title compound, an 11% yield. m.p. 85–87° C.

EXAMPLE 203

2,3-Dichloro-N-ethyl-6-(trimethylsilyl)benzamide 2,3-Dichloro-6-(trimethylsilyl)benzoic acid was prepared from 2,3-dichlorobenzoic acid according to the procedure of example a in 45% yield as 3.07 g of a white solid. m.p. 117–119° C.

This acid was converted to the acid chloride by the procedure of example b. The acid chloride was reacted with aq ethylamine using General Method E1 to afford the title compound. Purification by recrystallization from hexanes gave 0.42 g of the title compound as white crystals in 58% yield. m.p. 96–98° C.

EXAMPLE 204

2,3-Dichloro-N-(2-propenyloxy)-6-(trimethylsilyl) benzamide

The acid prepared in Example 203 was converted to the acid chloride by the procedure of example b. The acid chloride was reacted with aq O-allylhydroxylamine using General Method E1 to afford the title compound. Purification by recrystallization from ether/hexanes gave 0.68 g of the title compound as a white solid in 86% yield. m.p. 92–94° C.

EXAMPLE 205

2,3-Dichloro-6-(trimethylsilyl)benzoic acid, 2,2-dimethylhydrazide

The acid prepared in Example 203 was converted to the acid chloride by the procedure of example b. The acid chloride was reacted with 1,1-dimethylhydrazine using General Method E1 to afford the title compound. Purification by recrystallization from ether/hexanes gave 0.62 g of the title compound as off-white crystals in 81% yield. m.p. 144–145° C.

EXAMPLE 206

2-Bromo-N-2-propynyl-6-(trimethylsilyl)benzamide

The compound of Example d was reacted with propargylamine (3 eq) according to General Method E1 and the crude product was recrystallized from hexanes to afford 0.55 g of the title compound as off-white needles in 81% yield. m.p. 120–121° C.

EXAMPLE 207

N-Ethyl-2-iodo-6-(trimethylsilyl)benzamide

A mixture of the 2-iodobenzoic acid, hexamethyldisilazane (0.55–0.60 eq) and TMSCl (5 drops) was heated at 135° C. for 2–4 h. The reaction mixture was distilled under vacuum to afford the trimethylsilyl ester of 2-iodobenzoic acid in 95% yield.

To a solution of 2,2,6,6-tetramethylpiperidine (1.1 eq) in THF at −78° C. was added a 1.6 M BuLi solution in hexanes (1.1 eq) dropwise. The reaction solution was put in an ice bath (0° C.) for 1 h and cooled to −78° C. The trimethylsilyl benzoate prepared above was added dropwise and stirred at −78° C. for 10–90 min. The reaction was quenched with sat aq citric acid and extracted with ether. The ether layers were extracted with 0.5 N NaOH and the basic aq layer was acidified with 2 N HCl and extracted with ether. The combined organic extracts were washed with brine, dried (MgSO4) and concentrated to afford crude 2-iodo-6-(trimethylsilyl)benzoic acid. The crude product was purified by recrystallization from hexanes to afford 3.62 g of white needles in 75% yield. m.p. 126–133° C.

This acid was converted to the acid chloride by the procedure of example b. The acid chloride was reacted with 70% aq ethylamine using General Method E1 to afford the title compound. Purification by recrystallization from hexanes gave 0.48 g of the title compound as white crystals in 88% yield. m.p. 135–137° C.

EXAMPLE 208

2-Iodo-N-2-propynyl-6-(trimethylsilyl)benzamide

The acid chloride prepared in Example 207 was reacted with propargylamine (3 eq) using General Method E1 to afford the title compound. Purification by recrystallization from hexanes gave 0.48 g of the title compound as an off-white solid in 85% yield. m.p. 109–111° C.

EXAMPLE 209

N-Cyclopropyl-2-iodo-6-(trimethylsilyl)benzamide

The acid chloride prepared in Example 207 was reacted with cyclopropylamine (3 eq) using General Method E1 to afford the title compound. Purification by recrystallization from hexanes gave 0.49 g of the title compound as white needles in 87% yield. m.p. 162–164° C.

EXAMPLE 210

2-[(Bromomethyl)dimethylsilyl]-6-chloro-N-ethylbenzamide

To a solution of the compound of example 45 (1.28 g, 5 mmol) in THF (30 mL) at −78° C. was added a 1.7 M solution of t-BuLi in pentane (6.5 mL, 11 mmol, 2.2 eq) such that the temperature was less than −70° C. The reaction was stirred at −78° C. for 1.5 h and ethylene dibromide (0.52 mL, 6.0 mmol, 1.2 eq) was added. The reaction was stirred for 15 min at −78° C. and worked up in the usual manner. The crude product was purified by RC and recrystallized from aq methanol to afford the title compound as white needles (0.30 g, 18%). m.p. 98–99° C.

EXAMPLE 211

[2-Chloro-6-(trimethylsilyl)benzoyl]ethylcarbamic acid, 1,1-dimethylethyl ester

To a solution of the compound of example 45 (3.83 g, 15 mmol) and di-t-butyl carbonate (3.60 g, 16.5 mmol) in acetonitrile was added 4-dimethylaminopyridine (0.18 g, 1.5 mmol). The solution was stirred at RT for 1 day, additional di-t-butyl carbonate (3.60 g) was added and stirring was continued for 3 days. Additional di-t-butyl carbonate (3.60 g) was added and the reaction was stirred overnight and concentrated. The residue was diluted with ether, washed with sat citric acid, sat NaHCO$_3$, brine, dried (MgSO$_4$) and concentrated to afford the title compound. The crude product was purified by flash chromatography (ethyl acetate/hexanes) and recrystallization from hexanes (−78° C.) to afford the title compound as a white solid (2.65 g, 50%). m.p. 51–52° C.

EXAMPLE 212

2-Chloro-N-ethyl-6-(ethyldimethylsilyl)benzamide

To a solution of the compound of example 45 (1.28 g, 5 mmol) and TMEDA (0.91 mL, 6.0 mmol, 1.2 eq) in THF at −78° C. was added a 1.7 M solution of t-BuLi in pentane (7.1 mL, 12 mmol, 2.4 eq) such that the temperature was less than −70° C. The reaction was stirred at −78° C. for 2 h and methyl iodide (0.44 mL, 7.0 mmol, 1.4 eq) was added. The reaction was stirred for 15 min at −78° C. and worked up in the usual manner. The crude product was recrystallized from aq methanol and then from hexanes to afford the title compound as white crystals (0.62 g, 46%). m.p. 94–95° C.

EXAMPLE 213

5-Chloro-N-ethyl-2-(trimethylsilyl)benzamide

2-Bromo-5-chlorobenzoic acid was converted to the acid chloride by the procedure of example b. The acid chloride was reacted with 70% aq ethylamine using General Method E1 to afford the amide. Purification by recrystallization from methylcyclohexane/ethyl acetate gave 4.69 g of 2-bromo-5-chloro-N-ethylbenzamide as a white solid in 75% yield. m.p. 98–99° C.

To a solution of this amide (1.05 g, 4.0 mmol) in THF (20 mL) at −78° C. was added a 1.6 M solution of n-BuLi in hexanes (5.5 mL, 8.8 mmol, 2.2 eq) dropwise such that the temperature was less than −70° C. The yellow solution was stirred at −78° C. for 30 min and TMSCl (0.61 mL, 4.8 mmol, 1.2 eq) was added dropwise. The solution was stirred at −78° C. for 45 min and worked up in the usual manner. The crude product was purified by RC (ethyl acetate/hexanes) and recrystallization from hexanes to afford the title compound as white needles (0.27 g, 26%). m.p. 104–105° C.

EXAMPLE 214

N-Ethyl-5-nitro-2-(trimethylsilyl)benzamide

To a solution of the amide of example 49 (1.10 g, 5 mmol) in $CH_2Cl_2$ (50 mL) at 0° C. was added dropwise over 2 min, a cold mixture of 70% nitric acid (0.95 mL, 15 mmol) and concentrated sulfuric acid (5 mL) dropwise. The mixture was stirred at 0° C. for 10 min and was poured onto ice. The mixture was extracted with ethyl acetate, the combined organic layers washed with brine, sat $NaHCO_3$, brine, dried ($MgSO_4$) and concentrated to a solid (2.68 g, 101%) consisting of a 2:1 ratio of 5-nitro and 3-nitro isomers. The title compound was obtained by RC (ethyl acetate/hexanes) in 60% yield as a white solid. m.p. 100–102° C.

EXAMPLE 215

6-Chloro-N-ethyl-3-nitro-2-(trimethylsilyl)benzamide

To a solution of the amide of example 45 (1.28 g, 5 mmol) in $CH_2Cl_2$ (20 mL) at 0° C. was added dropwise a cold mixture of 70% nitric acid (0.64 mL, 10 mmol) and concentrated sulfuric acid (5 mL) dropwise. The mixture was stirred at 0° C. for 10 min and was poured onto ice. The mixture was extracted with ether, the combined organic layers washed with sat $NaHCO_3$, brine, dried ($MgSO_4$) and concentrated to a solid (1.52 g, 101%). The title compound was obtained by recrystallization from ethyl acetate/hexanes in 83% yield as a white solid. m.p. 147–149° C.

EXAMPLE 216

2-Chloro-N-ethyl-3-nitro-6-(trimethylsilyl)benzamide

The mother liquors from Example 215 were purified by RC (ethyl acetate/hexanes) to give 0.11 g of the title compound in 7% yield as a white solid. Recrystallization from ethyl acetate/hexanes afforded pure title compound. m.p. 126–127° C.

EXAMPLE 217

5-Amino-N-ethyl-2-(trimethylsilyl)benzamide

A solution of the crude amide of Example 214 (2.67 g, 10 mmol) in ethanol (50 mL) with 10% palladium/carbon (0.3 g) was hydrogenated at 50 psi for 3 h. The catalyst was filtered off through Celite and the solution concentrated. The crude product was purified by RC (ethyl acetate/hexanes) and recrystallized from ethyl acetate/hexanes to afford the title compound as a white solid (0.64 g, 27%). m.p. 143–145° C.

EXAMPLE 218

3-Chloro-N-ethyl-2-fluoro-6-(trimethylsilyl)benzamide

The trimethylsilyl ester of 3-chloro-2-fluorobenzoic acid (11.66 g) was prepared in 84% yield using the method described in Example 207. This ester (2.47 g) was converted to 0.45 g of 3-chloro-2-fluoro-6-(trimethylsilyl)benzoic acid in 18% yield using the method of Example 207. The crude product was converted to the acid chloride by the procedure of example b. The acid chloride was reacted with 70% aq ethylamine using General Method E1 to afford the title compound. Purification by flash chromatography (ethyl acetate/hexanes) followed by recrystallization from pentane gave 84 mg of the title compound as an off-white solid (18%). m.p. 96–97° C.

EXAMPLE 219

2-Chloro-N-ethyl-3-methoxy-6-(trimethylsilyl)benzamide

2-Bromo-5-methoxybenzoic acid was converted to the acid chloride by the procedure of example b. The acid chloride was reacted with 70% aq ethylamine using General Method E1 to afford 24.44 g of 2-chloro-N-ethyl-3-methoxybenzamide in 95% yield.

This amide (2.58 g, 10 mmol) was dissolved in concentrated sulfuric acid (5 mL) and N-chlorosuccinimide (1.47 g, 11 mmol) was added portion-wise over 15 min. The mixture was stirred for 2 h and was poured into ice water. The mixture was extracted with ethyl acetate, washed with 1.25 N NaOH, sat sodium sulfite, brine, dried ($MgSO_4$) and concentrated to afford a white solid. The crude product was purified by recrystallization from ethyl acetate/hexanes to afford 6-bromo-2-chloro-N-ethyl-3-methoxybenzamide as white needles (1.92 g, 66%). m.p. 181–182° C.

To a solution of this amide (0.58 g, 2.0 mmol) in THF (20 mL) at −78° C. was added a solution of 1.6 M n-BuLi in hexanes (2.8 mL, 4.4 mmol). The reaction was stirred for 1 h at −78° C., allowed to warm to −30° C. and cooled to −78° C. TMSCl (0.30 mL, 2.4 mmol) was added, the reaction mixture allowed to warm to −30° C. and worked up in the usual manner. The crude product was purified by RC (ethyl acetate/hexanes) and recrystallized from hexanes to afford the title compound as an off-white solid (45 mg, 4%). m.p. 136–137° C.

EXAMPLE 220

3-Bromo-2-chloro-N-ethyl-6-(trimethylsilyl)benzamide

To a solution of the compound of Example 201 (0.79 g, 2.2 mmol) and TMEDA (0.44 mL, 2.9 mmol) in THF (20 mL) at −78° C. was added a solution of 0.86 M s-BuLi in cyclohexane (3.3 mL, 2.9 mmol). The reaction was stirred at −78° C. for 30 min and 1,2-dibromoethane (0.26 mL, 3.0 mmol) was added. The reaction was stirred for 15 min at −78° C. and was quenched with sat $NaHCO_3$. The mixture was extracted with ether, washed with brine, dried ($MgSO_4$)

and concentrated to afford a yellow oil. This oil was dissolved in a mixture of acetone (30 mL) and 6 N HCl (15 mL) and was stirred overnight. The mixture was concentrated, extracted with ether, the organic layers washed with brine, dried (MgSO$_4$) and concentrated to afford the title compound as a clear oil. The crude product was purified by RC (ethyl acetate/hexanes) and was recrystallized from pentane (−78° C.) to afford 76 mg of a white solid (10% yield). m.p. 105–106° C.

EXAMPLE 221

N-Ethyl-2-phenyl-6-(trimethylsilyl)benzamide

2-Phenylbenzoic acid was converted to the acid chloride by the procedure of example b. The acid chloride was reacted with 70% aq ethylamine using General Method E1 to afford 10.59 g of N-ethyl-2-phenylbenzamide in 94% yield. m.p. 77–79° C.

This amide (2.25 g, 10 mmol) and TMEDA (1.2 eq) in THF were mixed and cooled to −78° C. and a 1.3 M s-BuLi solution in cyclohexane (2.2 eq) was added dropwise. The resulting reaction mixture was stirred at −78° C. for 30 min and TMSCl (1.2 eq) was added dropwise. The reaction was stirred at −78° C. for 30 min and allowed to warm to −30° C. The reaction was worked up in the usual manner. The crude product was purified by flash chromatography and recrystallization from hexanes to afford the title compound as a white solid (1.15 g, 39%). m.p. 159–160° C.

EXAMPLE 222

5-(Dimethylamino)-N-ethyl-N-(1-methoxy-2,2-dimethylpropyl)-2-(trimethylsilyl)benzamide A solution of the compound of Example 201 (0.72 g, 2.0 mmol) and TMEDA (1.20 mL, 8.0 mmol) in THF (30 mL) at −78° C. was treated with a solution of 1.7 M t-BuLi in pentane (5.6 mL, 9.6 mmol) and allowed to slowly warm to −20° C. over 4 h. The reaction was quenched with 1,2-dibromoethane (0.86 mL, 10 mmol), was diluted with sat NaHCO$_3$, extracted with ether, the organic layers washed with brine, dried (MgSO$_4$) and concentrated to afford the title compound. The crude product was purified by RC (ethyl acetate/hexanes) and recrystallization from pentane (−78° C.) to afford the title compound as a white solid (0.14 g, 20%). m.p. 96–98° C.

EXAMPLE 223

2-Chloro-N-ethyl-3-formyl-6-(trimethylsilyl)benzamide

The method of Example 230 was followed, substituting DMF (2 eq) for MeI to afford the title compound. The crude product was purified by recrystallization from ethyl acetate/hexanes to afford 1.16 g of the title compound as white needles in 82% yield. m.p. 140–142° C.

EXAMPLE 224

2-Chloro-3-(difluoromethyl)-N-ethyl-6-(trimethylsilyl)benzamide

A solution of the compound of Example 223 (0.26 g, 0.92 mmol) in CH$_2$Cl$_2$ (10 mL) at 0° C. was treated with DAST (0.12 mL, 0.92 mmol) and kept for 22 h. The reaction was poured into water, extracted with ether, the organic layers washed with sat NaHCO$_3$, brine, dried (MgSO$_4$) and concentrated to afford the title compound. The crude product was purified by recrystallization from hexanes to afford 0.20 g of the title compound (70%) as off-white crystals. m.p. 120–121° C.

EXAMPLE 225

N-Ethyl-5-(trifluoromethyl)-2-(trimethylsilyl)benzamide.

3-Trifluoromethylbenzoic acid was converted to the acid chloride by the procedure of example b. The acid chloride was reacted with 70% aq ethylamine using General Method E1 to afford the title compound. Purification by recrystallization from hexanes gave 2.24 g of N-ethyl-3-(trifluoromethyl)benzamide as a white needles in 19% yield. m.p. 98–99° C.

This amide was reacted with TMSCl (1.3 eq) as in Example 221 to afford the title compound. The crude product was purified by RC (ethyl acetate/hexanes) and recrystallization from pentane (−78° C.) to afford 0.14 g (5%) of the title compound as a white solid. m.p. 101–102° C.

EXAMPLE 226

5-(Dimethylamino)-N-ethyl-2-(trimethylsilyl)benzamide

The compound of Example 222 (0.31 g, 0.85 mmol) was dissolved in CH$_2$Cl$_2$ (20 mL) and was treated with iodotrimethylsilane (2.1 mL, 15 mmol) in a foil-covered flask. The reaction was stirred for 2 h and was quenched with sat NaHCO$_3$. The mixture was extracted with ether, the organic layers were washed with brine and sat sodium bisulfite, dried (MgSO$_4$) and concentrated to afford the title compound. The crude product was a purified by RC (ethyl acetate/hexanes) and recrystallized from hexanes to afford 68 mg (5%) of the title compound as a white solid. m.p. 141–143° C.

EXAMPLE 227

2-Chloro-N-ethyl-3-(hydroxymethyl)-6-(trimethylsilyl)benzamide

To a solution of sodium borohydride (50 mg, 1.2 mmol) in ethanol (20 mL) was added the compound of Example 222 (0.62 g, 2.2 mmol). The mixture was stirred 45 min, was diluted with water and treated with potassium dihydrogenphosphate. The mixture was extracted with ethyl acetate, the organic layers washed with brine, dried (MgSO$_4$) and concentrated to afford the title compound. The crude product was purified by recrystallization from ethyl acetate/hexanes to afford white crystals (0.51 g, 82%). m.p. 244–245° C.

EXAMPLE 228

2-Chloro-N-ethyl-3-(fluoromethyl)-6-(trimethylsilyl)benzamide

A solution of the compound of Example 227 (0.29 g, 1.0 mmol) in CH$_2$Cl$_2$ (20 mL) was treated with DAST (0.26 mL, 2.0 mmol) and stirred for 1 h. The reaction was poured into water, extracted with ether, the organic layers washed with brine, dried (MgSO$_4$) and concentrated to afford the title compound. The crude product was purified by RC (ethyl acetate/hexanes) and recrystallization from hexanes to afford 0.20 g of the title compound (71%) as white crystals. m.p. 104–105° C.

EXAMPLE 229

2-Chloro-3-cyano-N-ethyl-6-(trimethylsilyl)benzamide

A solution of the compound of Example 223 (0.28 g, 1.0 mmol) and hydroxylamine hydrochloride (0.12 g, 1.7 mmol)

in pyridine (10 mL) was stirred at RT for 2 h. Acetic anhydride (0.75 mL, 8.0 mmol) was added and the solution was heated at 100° C. for 1.5 h. The mixture was concentrated, water added and the mixture extracted with ether. The organic layers were washed with 0.5 N HCl sat NaHCO$_3$, brine, dried (MgSO$_4$) and concentrated to afford the title compound. The crude product was purified by recrystallization from ethyl acetate/hexanes to afford 0.21 g of white needles (74%). m.p. 111–112° C.

EXAMPLE 230

2-Chloro-N-ethyl-3-methyl-6-(trimethylsilyl) benzamide

A solution of the compound of Example 201 and TMEDA (1 eq) in THF/ether (1:1) at –100° C. was treated dropwise with a solution of 1.3 M s-BuLi in cyclohexane in hexanes (2.0–2.2 eq) such that the temperature was less than –95° C. The reaction was stirred at –100° C. for 30 min, MeI (2.2 eq) was added and the reaction was allowed to warm to –30° C. The reaction was worked up in the usual manner.

The crude product was hydrolyzed to the N-ethylbenzamide by dissolution in dioxane (7.5 mL/mmol) and addition of conc HCl (2.5 mL/mmol). The mixture was stirred at RT for 1.5 h and brine was added. The mixture was extracted with ether, the organic extracts washed with sat NaHCO$_3$, brine, dried (MgSO$_4$) and concentrated. The crude product was purified by recrystallization from hexanes followed by recrystallization from aq methanol (2 times) to afford 0.18 g of the title compound as white needles in 27% yield. m.p. 120–122° C.

EXAMPLE 231

2-Chloro-N-ethyl-3-(methylthio)-6-(trimethylsilyl) benzamide

The method of Example 230 was followed, substituting methyl methanethiolsulfonate (2.2 eq) for methyl iodide to afford the title compound. The crude product was purified by recrystallization from ethyl acetate/hexanes to afford 1.12 g of the title compound as white needles in 74% yield. m.p. 137–139° C.

EXAMPLE 232

3-Bromo-6-chloro-N-ethyl-2-(trimethylsilyl) benzamide

2-Chloro-5-bromobenzoic acid (20 g, 0.08 mol) in CH$_2$Cl$_2$ (50 mL) was treated with oxalyl chloride (30 mL, 0.34 mol) and DMF (catalytic) for 2 h at RT. The reaction mixture was concentrated under vacuum to give the acid chloride. The acid chloride was reacted with ethyl amine as described in Method E2 to give 2-chloro-5-bromo-N-ethylbenzamide.

LDA was formed by adding 2.5 M n-BuLi (1.7 mL, 0.004 mol) to diisopropylamine (0.6 mL, 0.004 mol) in 10 mL THF at –78° C. The mixture was warmed briefly to 0° C. then cooled to –78° C. A solution of the above compound in THF (5 mL) was added. After 0.5 h at –78° C., TMSCl (0.31 mL, 0.0024 mol) was added. The reaction mixture was warmed to –40° C. and poured into aq NaHCO$_3$ and extracted with ether. The ether extract was washed with water and brine, dried (MgSO$_4$) and concentrated. The crude product was purified by flash chromatography (0–15% ethyl acetate/hexanes) to give the title compound as a white solid (0.2 g) in 32% yield. m.p. 155–157° C.

EXAMPLE 233

3-Amino-6-chloro-N-ethyl-2-(trimethylsilyl) benzamide

A mixture of the compound of Example 215 (6.85 g, 0.023 mol) and PtO$_2$ (catalytic) in ethanol was placed on the Parr Hydrogenator for 16 h. The reaction mixture was filtered through celite and concentrated. The resulting solid was dissolved in CH$_2$Cl$_2$ and filtered through silica gel three times. The filtrate was concentrated to give the title compound as a yellow solid in 13% yield. m.p. 147–149° C.

EXAMPLE 234

2,4-Dichloro-N-ethyl-6-(trimethylsilyl)benzamide

The 2,4-dichloro-N-ethyl benzamide (5.8 g, 0.027 mol) was prepared in 92% yield from 2,4-dichlorobenzoyl chloride (4 ml, 0.03 mol) and ethyl amine (70 wt % in H$_2$O) using Method E2.

1.5 M LDA in THF was added dropwise to a solution of the above amide (2 g, 0.01 mol) and TMSCl (1.5 ml, 0.011 mol) in THF, cooled to –100° C. under nitrogen. After 30 min the reaction mixture was poured into dilute aq NaHCO$_3$ and extracted with ether. The ether extract was washed with water and brine, dried (MgSO$_4$) and concentrated. The crude product was filtered through silica gel with a gradient elution of ethyl acetate/hexanes and concentrated to give the title compound as a white solid in 19% yield. m.p. 101–103° C.

EXAMPLE 235

2-Chloro-4-(1,1-dimethylethyl)-N-ethyl-6-(trimethylsilyl)benzamide 4-t-Butyl-N-ethylbenzamide (9 g, 0.044 mol) was prepared in 97% yield from 4-t-butylbenzoyl chloride (9 ml, 0.045 mol) and ethyl amine (70 wt % in water) using Method E2.

1.3 M s-BuLi in cyclohexane (41 mL, 0.053 mol) was added dropwise to a solution of the above amide (5 g, 0.024 mol) and TMEDA (4 ml, 0.027 mol) in THF, cooled to –78° C. under nitrogen. After 30 min a solution of hexachloroethane (6.4 g, 0.027 mol) in THF was added. After 0.5 h at –78° C. the reaction mixture was warmed to –30° C. and poured into dilute aq NaHCO$_3$ and extracted with ether. The ether extract was washed with water and brine, dried (MgSO$_4$) and concentrated. The resulting solid was recrystallized from cyclohexane to give 5 g of 2-chloro-4-t-butyl-N-ethylbenzamide, a white solid.

To a solution of the above compound (2.5 g, 0.01 mol) and TMEDA (1.66 mL, 0.011 mol) in THF, cooled to –78° C. under nitrogen, was added 1.3 M s-BuLi in cyclohexane (17 mL, 0.022 mol) dropwise. After 0.5 h TMSCl (1.6 mL, 0.0125 mol) was added. The reaction mixture was stirred at –78° C. for 45 min then warmed to –30° C. and poured into dilute aq NaHCO$_3$ and extracted with ether. The ether extract was washed with water and brine, dried (MgSO$_4$) and concentrated. The crude product was purified by flash chromatography (0–10% ethyl acetate/hexanes) to give the title compound as a white solid (0.78 g) in 25% yield. m.p. 124–126° C.

EXAMPLE 236

6-Bromo-N-ethyl-3-methoxy-2-(trimethylsilyl) benzamide

2-Bromo-5-methoxybenzoic acid was converted to the acid chloride following example b and then to the ethyl amide using Method E1.

A solution of the ethyl amide (1 g, 0.004 mol) and TMSCl (0.63 mL, 0.005 mol) in THF (15 mL) was cooled to −100° C. under nitrogen and 2 M LDA (4.5 mL, 0.009 mol) was added dropwise. After stirring at −78° C. for 0.5 h the reaction mixture was poured into aq $NaHCO_3$ and extracted with ether. The ether extract was washed with water and brine, dried ($MgSO_4$) and concentrated. The crude product was triturated with ether and the resulting solid was recrystallized from aq ethanol to give the title compound as a white solid (100 mg) in 8% yield. m.p. 200° C.

EXAMPLE 237

6-Chloro-3-(dimethylamino)-N-ethyl-2-(trimethylsilyl)benzamide

2-Chloro-5-nitro-N-ethylbenzamide was prepared from the corresponding acid using the Method of Example 232. A solution of this compound (25 g, 0.11 mol) in ethyl acetate (250 mL), water (75 mL) and glacial acetic acid (325 mL) was heated then iron powder (25 g, 0.44 mol) was added. The reaction mixture exothermed and gas evolution was vigorous for 1 h, even though it was cooled with an ice bath. When gas evolution ceased the reaction mixture was poured into water and $CH_2Cl_2$ and filtered to remove the remaining iron. The filtrate was extracted with $CH_2Cl_2$ several times. The organic layers were combined and washed with water and brine, dried ($MgSO_4$) and concentrated to give 2-chloro-5-amino-N-ethylbenzamide as an oil (12.5 g, 57% yield).

A mixture of the above amine (3 g, 0.015 mol), potassium carbonate (3.8 g, 0.028 mol) and MeI (1.4 mL, 0.022 mol) in DMF stirred at RT overnight. The reaction mixture was poured into water and extracted with ether. The ether layer was washed with water and brine, dried ($MgSO_4$) and concentrated to give an oil. Purification by flash chromatography (0–50% ethyl acetate/hexanes) gave N-ethyl 2-chloro-5-(dimethylamino)benzamide as a yellow solid in 29% yield.

A solution of the above compound (0.65 g, 0.003 mol) in THF was stirred at −78° C. under nitrogen. 1.7 M t-BuLi in pentane was added. After 0.5 h at −78° C. a solution of TMSCl in THF was added. After 1 h at −78° C. the reaction mixture was poured into aq $NaHCO_3$ and extracted with ether. The ether extract was washed with water and brine, dried ($MgSO_4$) and concentrated. The crude product was triturated with a mixture of hexanes/$CH_2Cl_2$/ethyl acetate and filtered to give the title compound as a white solid (0.100 g) in 11% yield. m.p. 179–180° C.

EXAMPLE 238

2-Chloro-N-ethyl-3-(methylsulfonyl)-6-(trimethylsilyl)benzamide

To a solution of the compound of Example 231 (0.30 g, 1.0 mmol) in $CH_2Cl_2$ (20 mL) at RT was added m-chloroperbenzoic acid (0.59 g, 3.4 mmol). The reaction was stirred for 7 h, was washed with sat $NaHCO_3$, brine, dried ($MgSO_4$) and concentrated to afford the title compound. The crude product was purified by recrystallization from ethyl acetate/hexanes to afford white needles (0.26 g, 79%). m.p. 139–140° C.

EXAMPLE 239

2-Chloro-N-ethyl-3-iodo-6-(trimethylsilyl)benzamide

The method of Example 230 was followed, substituting 1,2-diiodoethane (2.3 eq) for MeI, to afford the title compound. The crude product was purified by flash chromatography (ethyl acetate/hexanes) and recrystallization from aq methanol to afford 2.72 g of the title compound as white crystals in 71% yield. m.p. 128–130° C.

EXAMPLE 240

5-(Benzoylamino)-N-ethyl-2-(trimethylsilyl)benzamide

To a solution of the compound of Example 217 (0.118 g, 0.5 mmol) in $CH_2Cl_2$ (10 mL) was added triethylamine (0.14 mL, 1.0 mmol), benzoyl chloride (70 μL, 0.6 mmol) and 4-dimethylaminopyridine (12 mg). The reaction was stirred at RT for 16 h, diluted with water, and extracted with ethyl acetate. The extracts were washed with 0.04 N HCl, sat $NaHCO_3$, brine, dried ($MgSO_4$) and concentrated to afford the title compound. The crude product was purified by recrystallization from ethyl acetate/hexanes to afford the title compound as fluffy white crystals (0.129 g, 76%). m.p. 185–187° C.

EXAMPLE 241

2-Chloro-N-ethyl-3-(2-(E)-nitro-ethenyl)-6-(trimethylsilyl)benzamide

To a solution of the compound of Example 223 (0.199 g, 0.7 mmol) in methanol (5 mL) at 0° C. was added nitromethane (0.3 mL, 5.0 mmol) and 2.5 N NaOH (2.3 mL, 5.8 mmol) portionwise over 2 h. The suspension was dissolved by addition of ice-cold water and cold 2 N HCl (10 mL) was added. The precipitate was filtered and washed with water to afford the crude title compound. The crude product was purified by recrystallization from aq methanol to afford the title compound as a light yellow fluffy solid (60 mg, 26%). m.p. 104–106° C.

EXAMPLE 242

2-Chloro-N-ethyl-3-phenyl-6-(trimethylsilyl)benzamide

To a solution of the compound of Example 239 (0.191 g, 0.5 mmol) and palladium tetrakistriphenylphosphine (23 mg, 0.02 mmol) in toluene (10 mL) was added 2 M sodium carbonate (0.5 mL) and phenyl boronic acid (73 mg, 0.6 mmol). The mixture was heated at 90° C. for 30 h, additional portions of catalyst (20 mg) and 2 M sodium carbonate (0.5 mL) were added and heating was continued for 24 h. The cool reaction was diluted with $CH_2Cl_2$ and washed with 2 M sodium carbonate (50 mL with 5 mL conc $NH_4OH$). The organic layer was dried ($MgSO_4$) and concentrated. The crude product was purified by RC (ethyl acetate/hexanes) and recrystallization from hexanes to afford the title compound as white needles (98 mg, 59%). m.p. 134–135° C.

EXAMPLE 243

3-Acetyl-2-chloro-N-ethyl-6-(trimethylsilyl)benzamide

To a solution of the compound of Example 223 (0.284 g, 1.0 mmol) in THF (20 mL) at −78° C. was added a 1.4 M solution of methyl lithium in ether (3.2 mL, 4.4 mmol) portionwise over 1 h. The reaction mixture was stirred for an additional hour at −78° C. and was quenched with sat citric acid. The mixture was extracted with ethyl acetate and the organic layers were washed with brine, dried ($MgSO_4$) and concentrated to afford the secondary alcohol as an oil.

A solution of the crude alcohol in ethyl acetate was added to a slurry of pyridinium chlorochromate (0.54 g, 2.5 mmol) in $CH_2Cl_2$ (50 mL). The slurry was stirred for 3 days, ether (100 mL) was added and the slurry was filtered through a pad of silica gel and concentrated to afford the title compound as an oil. The crude product was purified by RC (ethyl acetate/hexanes), followed by recrystallization from ether/hexanes to afford the title compound as white needles (0.126 g, 42%). m.p. 78–80° C.

EXAMPLE 244

2-Chloro-3-[(ethylamino)carbonyl]-4-(trimethylsilyl) benzoic acid, methyl ester

To a solution of silver nitrate (0.71 g, 4.2 mmol) in water (20 mL) was added 2.5 N NaOH (3.4 mL, 8.2 mmol) giving a brown suspension. A solution of the aldehyde of Example 223 (0.56 g, 2.0 mmol) in THF (25 mL) was added and the mixture was stirred at RT for 2 h. The mixture was filtered through Celite, diluted with water and washed with $CH_2Cl_2$. The aq solution was acidified with 2 N HCl and extracted with $CH_2Cl_2$. The organic layers were washed with brine, dried ($MgSO_4$) and concentrated to afford the carboxylic acid as a white solid (0.57 g, 95%).

The carboxylic acid was converted to the acid chloride by the procedure of example b.

To a solution of the acid chloride (0.48 mmol) in toluene (10 mL) was added triethylamine (0.139 mL, 1.0 mmol) and methanol (0.08 mL, 2.0 mmol). The reaction was stirred at RT for 16 h, diluted with sat $NaHCO_3$ and extracted with ethyl acetate. The organic layers were washed with brine, dried ($MgSO_4$) and concentrated to afford the title compound. The crude product was purified by recrystallization from ether/hexanes at −78° C. to afford the title compound as a white solid (0.104 g, 69%). m.p. 103–104° C.

EXAMPLE 245

N-Ethyl-5-isothiocyanato-2-(trimethylsilyl) benzamide

To a solution of the compound of Example 217 (0.354 g, 1.5 mmol) in $CH_2Cl_2$ (25 mL) was added 1,1'-thiocarbonyl-2(1H)pyridone (0.35 g, 1.5 mmol). The solution was stirred at RT for 40 min, was diluted with $CH_2Cl_2$ and washed with water, brine, dried ($MgSO_4$) and concentrated to afford the title compound. The crude product was purified by flash chromatography ($CH_2Cl_2$), followed by recrystallization from hexanes to afford the title compound as white needles (0.336 g, 81%). m.p. 106.5–108° C.

EXAMPLE 246

N-Ethyl-3-nitro-2-(trimethylsilyl)benzamide

The title compound was obtained as the minor product in the preparation of Example 214 by RC (ethyl acetate/hexanes). The crude product was recrystallized from ether/hexanes and dried at 65° C. @ 0.05 mm to afford the title compound as white needles (0.656 g, 25%). m.p. 84–86° C.

EXAMPLE 247

N-Ethyl-2-(1,1-dimethylethoxy)benzamide

2-Iodobenzoic acid (65.92 g, 0.266 mol), oxalyl chloride (40.5 g, 0.319 mol), $CH_2Cl_2$ (200 mL) and DMF (10 drops) were stirred at RT overnight. The reaction solution was concentrated, toluene was added and the solution concentrated to afford the crude 2-iodobenzoyl chloride.

The acid chloride was reacted with 70% aq ethyl amine using General Method E1 to afford N-ethyl-2-iodobenzamide as a tan solid (70.80 g, 97%).

Potassium t-butoxide (12.25 g, 0.109 mol) was dissolved in pyridine (50 mL) and cuprous chloride (10.81 g, 0.109 mol) was added. The black suspension was stirred at RT for 30 min and N-ethyl-2-iodobenzamide (10.00 g, 36.4 mmol) dissolved in pyridine (20 mL) was added dropwise. The mixture was stirred at room temperature for 1 h and was poured in aq ammonium hydroxide and extracted with ether. The organic extracts were washed with 1 N NaOH, brine, dried ($MgSO_4$) and concentrated to afford a brown semi-solid. The crude product was purified by flash chromatography (ethyl acetate/hexanes) to afford the title compound as a light yellow solid (2.36 g, 29%). m.p. 34.5–36° C.

EXAMPLES 248 & 249

Example 248: N-Ethyl-3-(trimethylsilyl)-2-thiophenecarboxamide

Example 249: N-Ethyl-3,5-bis(trimethylsilyl)-2-thiophenecarboxamide (a) A mixture of 20 g of 2-thiophenecarboxylic acid and 30 mL thionyl chloride was heated at reflux for 2.5 h, then cooled and concentrated in vacuo to give 21 g of crude 2-thiophenecarboxylic acid chloride as an amber oil.

(b) A solution of 2-thiophenecarboxylic acid chloride (7.3 g, 50 mmol) in 30 mL $CH_2Cl_2$ was added to 70% ethylamine in water (11 g) at −5° C. and the resulting solution was stirred at RT for 18 h. After that, water was added. The organic layer was separated, washed with water, brine, dried and concentrated. Purification of the residue by flash chromatography with 25% ethyl acetate-hexane gave 6.4 g (83.1% yield) of N-ethyl-2-thiophenecarboxamide as a white solid, m.p. 75–78° C.

(c) A solution of 2.5M n-BuLi in hexane (18 mL) was added dropwise to a solution of N-ethyl-2thiophenecarboxamide (3.1 g, 20 mmol) in 50 mL THF at below −65° C. under a positive nitrogen atmosphere and the resulting solution was stirred at −70° C. for 45 min. After that, TMSCl (9 mL) was added slowly at below −60° C. and stirring was continued at below −60° C. for 15 min. The solution was allowed to warm to 0° C., then poured into water and extracted with $CH_2Cl_2$. The organic layer was separated, washed with brine, dried and concentrated. Flash chromatography of the residue with 5% ethyl-acetate-hexane yielded 3.1 g of Example 248 as a white solid, m.p. 81–84° C., and 1.1 g of Example 249 as a colorless oil. $n_D^{24}$ 1.5228.

EXAMPLE 250

N,N-Diethyl-2,4-bis(trimethylsilyl)-3-furancarboxamide a) To a solution of diisopropylamine (10 g, 0.1 mol) in 90 mL THF under a positive nitrogen atmosphere was added 2.5M n-BuLi in hexane (40 mL, 0.1 mol) at below −20° C. and the resulting solution was stirred at below −20° C. for 0.5 h, then cooled to −70° C. and a solution of 3-furoic acid (5.1 g, 46 mmol) in 50 mL THF was added, maintaining the temperature at below −70° C. After the addition was complete, stirring at −70° C. was continued for 1 h. Then 20 mL TMSCl was added dropwise at −70° C. and the reaction solution was stirred at −70° C. for 0.5 h, then allowed to warm to RT and poured into a mixture of $CH_2Cl_2$, ice-water and 2N HCl. The aq layer was separated and extracted with $CH_2Cl_2$. The combined organic layers were washed with brine, dried and concentrated to give a mixture of 2-(trimethylsilyl)-3-furoic acid and 2,4-bis(trimethylsilyl)-3-furoic acid.

b) A mixture of 3-furoic acid chlorides (prepared from a mixture of acids (1.4 g) of step a, 6 mL thionyl chloride and a catalytic amount of DMF according to the method of Example 248a was reacted with 4 g of diethylamine as in Example 248b. The crude mixture was purified by flash chromatography with 10% ethyl acetate-hexane to give 0.1 g of the title compound as a greenish oil. $n_D^{25}$ 1.4812.

EXAMPLE 251 & 252

Example 251: N-Ethyl-3,5-bis(trimethylsilyl)-2-furancarboxamide

Example 252: N-Ethyl-3-(trimethylsilyl)-2-furancarboxamide

Using the method of Examples 248 and 249, 2-furoic acid was converted to 2.7 g of Example 251 as a white solid, m.p. 99–102° C., and 1 g of Example 252 as a white solid. m.p. 69–72° C.

EXAMPLE 253

N-Ethyl-1-[(trimethylsilyl)methyl]-1H-pyrrole-2-carboxamide

A mixture of 1-methyl-2-pyrrolecarboxylic acid (10 g, 80 mmol) in 25 mL oxalyl chloride containing 6 drops of DMF was refluxed for 1 h, then cooled to RT and excess oxalyl chloride was removed in vacuo. The crude acid chloride was dissolved in $CH_2Cl_2$ and added slowly to 40 mL 70% aq ethylamine at between −15 and −10° C. The reaction solution was stirred at RT for 1 h, then poured into water and extracted with $CH_2Cl_2$. The organic solution was washed with brine, dried and concentrated. The residue was purified by flash chromatography with 25% ethyl acetate-hexane to provide 9.5 g of desired product as a light yellow solid.

To the ethyl amide (1.5 g, 10 mmol) in 16 mL THF under a positive nitrogen atmosphere was added 12 mL 2.5M of n-BuLi in hexane at around 30° C. and the resulting solution was stirred at ambient temperature for 1 h. Then 6 mL TMSCl was added slowly at 0° C. and stirring was continued at ambient temperature for 1 h. After that, the solution was poured into ice-water and extracted with $CH_2Cl_2$. The organic solution was washed with water, brine, dried and concentrated in vacuo. Flash chromatography of the residue with 10% ethyl acetate-hexane gave 0.6 g of desired product as an orange oil. $n_D^{25}$ 1.5185.

EXAMPLE 254

5-Chloro-N-ethyl-3-(trimethylsilyl)-2-thiophenecarboxamide

The title compound was prepared from 5-chloro-2-thiophenecarboxylic acid using the methods of Example 248 yielding 1.5 g as a white solid. m.p. 105–108° C.

EXAMPLE 255

N,N-Diethyl-3-(trimethylsilyl)-2-thiophenecarboxamide

To a solution of the compound of Example 248 (1.1 g, 5 mmol) in 10 mL THF under a positive nitrogen atmosphere was added dropwise 2.4 mL 2.5M n-BuLi in hexane at −40° C. Stirring was continued at between −30 and −20° C. for 1 h. After that, 2 g ethyl iodide was added dropwise. The resulting reaction solution was allowed to warm to RT, stirred at RT for 18 h and then poured into water and $CH_2Cl_2$. The organic layer was separated, washed with brine, dried and concentrated in vacuo. The residue was purified on a silica gel column with 10% ethyl acetate-hexane as eluent to give 1 g of the title compound as a colorless oil. $n_D^{25}$ 1.5218.

EXAMPLE 256

N-Ethyl-5-methyl-3-(trimethylsilyl)-2-thiophenecarboxamide

The title compound was prepared from 5-methyl-2-thiophenecarboxylic acid using the methods of Example 248 yielding 3.6 g as a white solid. m.p. 112–115° C.

EXAMPLE 257

N-Ethyl-5-iodo-3-(trimethylsilyl)-2-thiophenecarboxamide

The compound of Example 248 was reacted with iodine using the method of step c of Example 248 to give 0.5 g of the title compound as a white solid. m.p. 85–88° C.

EXAMPLE 258

N-Ethyl-5-formyl-3-(trimethylsilyl)-2-thiophenecarboxamide a) To diisopropylamine (12.6 g, 0.125 mol) in 100 mL THF was added slowly 2.5M n-BuLi in hexane (52 mL, 0.13 mol) at −40° C. and stirred at −40° C. for 0.5 h. The solution was cooled to −60° C. and a solution of the compound of Example 248 (12.1 g) in 60 mL THF was added and stirring was continued at between −50 and −60° C. for 1 h. After that the reaction mixture was poured into ether-dry ice slush and extracted with water. The aq layer was acidified with conc HCl and extracted with $CH_2Cl_2$. The organic layer was washed with brine, dried and concentrated in vacuo to afford 5-[(ethylamino)carbonyl]-4-(trimethylsilyl)-2-thiophenecarboxylic acid.

b) To a solution of the acid of step a (3.6 g, 12 mmol) in 30 mL THF was added dropwise 30 mL of 1M of diborane in THF at 0° C. After the addition was complete, the resulting reaction mixture was stirred at RT for 1 h, then cautiously poured into ice-water and extracted with $CH_2Cl_2$. The organic water was washed with brine, dried and concentrated in vacuo. The crude product was purified by flash chromatography with 30% ethyl acetate-hexane as eluent to give 2.5 g of N-ethyl-5-(hydroxymethyl)-3-(trimethylsilyl)-2-thiophenecarboxamide.

c) To the compound of step b (1.3 g, 5 mmol) in 40 mL $CH_2Cl_2$ containing 1.8 g celite was added 2.4 g pyridinium chlorochromate and the resulting reaction mixture was stirred at RT for 2 h. The $CH_2Cl_2$ solution was filtered through celite, washed with water, brine, dried and concentrated in vacuo. The residue was purified by flash chromatography with 10% ethyl acetate-hexane to give 1.1 g of the desired product as a light yellow solid, m.p. 62–65° C.

EXAMPLE 259

N-Ethyl-4-(trimethylsilyl)-5-isothiazolecarboxamide a) 5-Isothiazolecarboxylic acid was prepared from isothiazole, n-BuLi and dry ice according to the method of step a of Example 258.

b) This compound was converted to the title compound by reaction with 70% aq ethylamine, followed by TMSCl, using the methods of Example 248 to give 0.3 g of the title compound as a yellow oil. $n_D^{25}$ 1.5275.

EXAMPLE 260

N-Ethyl-5-(methylsulfinyl)-3-(trimethylsilyl)-2-thiophenecarboxamide

To a solution of 3.4 g of a 50:50 mixture of the compound of example 248 and 5-(methylthio)-3-(trimethylsilyl)-2-thiophenecarboxamide (obtained from the reaction of compound of example 248 and methyl methanethiosulfonate using the method of step c of Example 248) in 30 mL methanol was added sodium periodate (1 g, 4 mmol) and the resulting reaction mixture was stirred at RT for 18 h. After that, the solvent was removed in vacuo and the residue was chromatographed on a silica gel column with 10%, 30% and then 70% ethyl acetate-hexane to give 1 g of the title compound as a white solid. m.p. 71–76° C.

EXAMPLE 261

N-Ethyl-5-(methylthio)-3-(trimethylsilyl)-2-thiophenecarboxamide

To a solution of the compound of Example 260 (0.6 g) and NaI (0.8 g) in 10 mL acetone was added slowly 0.4 mL trifluoroacetic anhydride at 0° C. and the mixture was stirred at 0° C. for an additional hour. Then $CH_2Cl_2$ and aq sat sodium meta-bisulfite were added. The organic layer was separated, washed with brine, dried and concentrated. Flash chromatography of the residue with 10% ethyl acetate-hexane gave 0.5 g of the title compound as a white solid. m.p. 58–61° C.

EXAMPLE 262

5-Chloro-N-(2-propenyl)-3-(trimethylsilyl)-2-thiophenecarboxamide

The title compound was prepared from 5-chloro-2-thiophenecarboxylic acid and allylamine, followed by reaction with TMSCl using the methods of Example 248 to afford 0.7 g of the title compound as a white solid. m.p. 63–66° C.

EXAMPLE 263

5-Chloro-N-(2-hydroxyethyl)-3-trimethylsilyl-2-thiophenecarboxamide

According to the method of step c of Example 248, a solution of 5-chloro-2-thiophenecarboxylic acid (3.3 g, 20 mmol) in THF was reacted with 20 mL 2.5M n-BuLi in hexane and then quenched with 8 mL TMSCl to give crude 5-chloro-3-(trimethylsilyl)-2-thiophenecarboxylic acid.

This acid and a catalytic amount of DMF in 10 mL thionyl chloride was refluxed for 2 h, then cooled to RT and excess thionyl chloride was removed in vacuo. The crude acid chloride was reacted with 2-aminoethanol according to the method of step b of Example 248 to give 0.9 g of the title compound as a white solid, m.p. 110–114° C.

EXAMPLE 264

5-Chloro-N-(2-chloroethyl)-3-(trimethylsilyl)-2-thiophenecarboxamide

A solution of the compound of Example 263 (0.4 g) and 1 mL thionyl chloride in 6 mL $CH_2Cl_2$ was refluxed for 1 h, then cooled and poured into ice-water. Additional $CH_2Cl_2$ was added. The organic layer was separated, washed with brine, dried and concentrated. Flash chromatography of the residue with 5% ethyl acetate-hexane as eluent gave 0.4 g of the desired product as a white solid. m.p. 68–72° C.

EXAMPLE 265

5-Chloro-N-[2[(methylsulfonyl)oxy]ethyl]-3-(trimethylsilyl)-2-thiophenecarboxamide To a solution of the compound of Example 263 (0.4 g) and 0.5 mL triethylamine in 10 mL $CH_2Cl_2$ at 0° C. was added methanesulfonyl chloride (0.2 mL) and the resulting reaction solution was stirred at RT for 2 h. Water was added and the two layers were separated. The organic solution was washed with brine, dried and concentrated. Purification by flash chromatography with 30% ethyl acetate-hexane gave 0.4 g of product as a white solid. m.p. 82–86° C.

EXAMPLE 266

5-Bromo-N-ethyl-3-(trimethylsilyl)-2-thiophenecarboxamide

The title compound was prepared from the compound of Example 248 and bromine according to step c of Example 248. Purification by flash chromatography with 5% ethyl acetate-hexane gave 0.6 g of the product as a white solid. m.p. 96–98° C.

EXAMPLE 267

4-Bromo-N-ethyl-2-(trimethylsilyl)-3-thiophenecarboxamide a) To a solution of 3,4-dibromothiophene (15 g, 62 mmol) in 80 mL ether under a positive nitrogen atmosphere was added dropwise 75 mL 1.7M t-BuLi in pentane at below −73° C. and the resulting reaction solution was stirred at −78° C. for 0.5 h. After that, the ether solution was poured into dry ice and extracted with water. The aq solution was washed with ether and then acidified with concentrated HCl. The solid was filtered and air-dried to give 9 g of 4-bromo-3-thiophenecarboxylic acid, yield 70.3%.

b) N-Ethyl-4-bromo-3-thiophenecarboxamide was prepared from 4-bromo-3-thiophenecarboxylic acid (7 g, 34 mmol) and 70% ethylamine in water according to steps a and b of Example 248 in 64.5% yield.

c) A solution of this compound (1.9, 8.1 mmol) in THF was metallated with LDA (prepared by diisopropylamine and 2.5M of n-BuLi in hexane using the method of Example 250) and quenched with TMSCl according to the method of step c of Example 248 to give 1.1 g of the title compound as a white solid in 44.5% yield. m.p. 93–96° C.

EXAMPLE 268

5-Bromo-N-ethyl-2-(trimethylsilyl)-3-thiophenecarboxamide a) To a solution of 3-thiophenecarboxylic acid (7.7 g, 60 mmol) in 70 mL acetic acid was added a solution of 9.6 g bromine in 50 mL acetic acid at RT and stirring was continued at RT for 0.5 h. After that, the reaction mixture was poured into 600 mL ice-water. The precipitate was filtered, washed with water and air-dried to give 7.9 g of 5-bromo-3-thiophenecarboxylic acid.

b) 5-Bromo-N-ethyl-3-thiophenecarboxamide was prepared from 5-bromo-3-thiophenecarboxylic acid (2.1 g, 10 mmol) and 70% ethylamine in water according to the methods of steps a and b of Example 248 in 70% yield.

c) The compound of step b (1.3 g, 5.6 mmol) was metallated with LDA (prepared from diisopropylamine and 2.5M n-BuLi in hexane as in Example 250) and reacted with TMSCl as in step c of Example 248 to give 70.6% of the title compound as a white solid. m.p. 96–98° C.

EXAMPLE 269

N-Ethyl-2,5-bis(trimethylsilyl)-3-thiophenecarboxamide

To a solution of 5-bromo-3-thiophenecarboxylic acid in 40 mL THF under a positive nitrogen atmosphere was added dropwise a solution of 9 mL of 2.5M n-BuLi in hexane at below −70° C. and the resulting reaction solution was stirred at −78° C. for 1 h. Then 3.6 mL TMSCl was added at below −70° C. and stirring was continued for 1 h at −78° C. The solution was allowed to warm to 0° C. and poured into water and washed with ether. The aq layer was separated, acidified with conc HCl and extracted with $CH_2Cl_2$. The organic solution was dried over $MgSO_4$ and concentrated to give a mixture of acids.

The acids were converted to the corresponding ethyl amides as in steps a and b of Example 248 and the mixture was purified by flash chromatography with 10% ethyl acetate-hexane to give 0.4 of the title compound as a white solid. m.p. 106–111° C.

EXAMPLE 270

N-Ethyl-2-(trimethylsilyl)-4,5,6,7-tetrahydrobenzo[B]thiophene-3-carboxamide a) To a mixture of cyclohexanone (20 g, 0.2 mol), ethyl cyanoacetate (22.6 g, 0.2 mol) and sulfur (6.8 g 0.22 mol) in 70 mL absolute ethanol was added rapidly 20 mL diethylamine. The reaction mixture was occasionally cooled with a water bath to maintain the temperature below 60° C. and then stirred at between 30 to 46° C. for 2 h. Then water was added. The precipitate was filtered, air-dried and recrystallized from ethanol to give 31 g of ethyl 2-amino-4,5,6,7-tetrahydrobenzo[B]-3-carboxylate.

b) To copper (II) bromide (14 g) and 90% t-butyl nitrite (10 mL) in 40 mL acetonitrile at 50° C. was added in portions 11 g of the amine of step a, such that the temperature did not exceed 65° C. After the addition was complete, the resulting reaction mixture was stirred for an additional 0.5 h, then partitioned between water and ethyl acetate. The ethyl acetate solution was then washed with water, brine, dried and concentrated. The crude product was chromatographed with 2% ethyl acetate-hexane to give 6.5 g of a 3:1 mixture of ethyl 2-bromo-4,5,6,7-tetrahydrobenzo[B]thiophene-3-carboxylate and ethyl 4,5,6,7-tetrahydrobenzo[B]thiophene-3-carboxylate.

A solution of the mixture of ethyl esters (5 g) and potassium hydroxide (3 g) in 20 mL ethanol was refluxed for 2 h, cooled and the solvent removed in vacuo. Water was added to the solid and the aq solution was acidified with conc HCl. The solid was filtered, washed with water and air dried to give 3.8 g of a mixture of acids.

A mixture of the two acids (3.3 g) and a catalytic amount of DMF in 10 mL thionyl chloride was refluxed for 2 h, then cooled and concentrated in vacuo. This mixture of crude acid chlorides was dissolved in 20 mL $CH_2Cl_2$ and added to 20 mL 70% ethylamine in water at below −20° C. and the mixture was stirred at RT for 18 h. The organic layer was separated, washed with water, brine, dried and concentrated. Flash chromatography of the crude with 15% ethyl acetate-hexane gave 3.2 g of 2-bromo-N-ethyl-4,5,6,7-tetrahydrobenzo[B]thiophene-3-carboxamide and 0.4 g of N-ethyl-4,5,6,7-tetrahydrobenzo[B]thiophene-3-carboxamide.

c) The 2-bromo compound was reacted with TMSCl according to the method of step c of Example 248. Purification by column chromatography with 12% ethyl acetate-hexane afforded 1.1 g of the title compound as a white solid. m.p. 107–112° C.

EXAMPLE 271

4,5-Dimethyl-N-ethyl-2-(trimethylsilyl)-3-thiophenecarboxamide

Using the procedures for the synthesis of the compound of Example 270 and methyl ethyl ketone as the starting material, the title compound was obtained as a white solid. m.p. 90–94° C.

EXAMPLE 272

N-Ethyl-N-(methylthio)-3-(trimethylsilyl)-2-thiophenecarboxamide

To a solution of the compound of Example 248 (1.6 g, 6.5 mmol) in 20 mL THF under a positive nitrogen atmosphere was added dropwise 3 mL of 2.5M n-BuLi in hexane at below −70° C. and the resulting solution was stirred at −78° C. for 1 h. A solution of methyl methanethiosulfonate (0.9 g, 7.1 mmol) in THF was then added dropwise at below −70° C. and stirring was continued for an additional hour at −78° C. After that, the solution was warmed to 0° C. and poured into water. $CH_2Cl_2$ was added. The aq layer was separated and extracted with $CH_2Cl_2$. The combined organic layers were washed with brine, dried ($MgSO_4$) and concentrated. Purification of the crude on a silica gel column with 10% ethyl acetate-hexane gave 1.2 g of the title compound as a colorless oil. $n_D^{24}$ 1.5519.

EXAMPLE 273

5-Chloro-N-(methylthio)-N-2-propenyl-3-(trimethylsilyl)-2-thiophenecarboxamide

The compound of Example 262 (1.1 g) was reacted with 0.52 g of methyl methanethiosulfonate using procedure described for the preparation of the compound of Example 272. The title compound (0.6 g) was purified by flash chromatography with 2% ethyl acetate-hexane and recovered as a colorless oil. $n_D^{25}$ 1.5698.

EXAMPLE 274

N-Ethyl-3-(trimethylsilyl)-4,5,6,7-tetrahydrobenzo[B]thiophene-2-carboxamide

To 9.4 mL DMF in 30 mL 1,2-dichloroethane was added dropwise 9.3 mL phosphorus oxychloride at below 10° C. The mixture was allowed to warm to RT and 10.3 mL cyclohexanone in 10 mL 1,2-dichloroethane was added. After the addition, the mixture was heated at 60–65° C. for 3 h, then cooled to RT and a solution of 30 g of sodium acetate in 60 mL water was added at below 20° C. The organic layer was separated, washed with water, brine and dried.

To the crude aldehyde in 1,2-dichloroethane was added in 1 portion 9 mL methyl thioacetate, followed by dropwise addition of 20 mL triethylamine. The reaction was exothermic and the mixture was stirred at ambient temperature for 18 h. After that, the organic layer was washed with 3N HCl, water, brine, dried and concentrated.

To this oil were added 4 mL 20% sodium methoxide in methanol and 60 mL methanol and the resulting solution was heated at reflux for 2 h. The solution was cooled and the solvent was removed in vacuo. Water and $CH_2Cl_2$ were added. The organic layer was separated, washed with brine, dried and concentrated to give 12.6 g of crude methyl 4,5,6,7-tetrahydrobenzo[B]thiophene-2-carboxylate as an oil.

A mixture of 2.2 g of this methyl ester and 20 mL of 70% ethylamine in water was stirred at RT for 72 h. After that water and $CH_2Cl_2$ were added. The organic layer was separated, washed with brine, dried and concentrated to give 2 g of ethyl amide as a light yellow solid, m.p.133–135° C.

The title compound was prepared from this ethyl amide (1.1 g, 5 mmol) and TMSCl according to the method of step c of Example 248. Purification by flash chromatography with 10% ethyl acetate-hexane gave 1 g of the product as a white solid. m.p. 126–128° C.

EXAMPLE 275

N-Ethyl-5-(methylamino)-2-(trimethylsilyl) benzamide

To a solution of the compound of Example 217 (0.29 g, 1.2 mmol) and benzotriazole (0.143 g, 1.2 mmol) in absolute ethanol (5 mL) at RT was added 37% aq formaldehyde (0.090 mL, 1.2 mmol). An aliquot was induced to precipitate by cooling and addition of a small amount of water. The precipitate was added back into the reaction which was stirred at RT overnight and cooled in a refrigerator for 6 h. The resultant mixture was filtered and dried under vacuum ($P_2O_5$) to afford 5-[(1H-benzotriazol-1-ylmethyl)amino]-N-ethyl-2-(trimethylsilyl)benzamide as a white solid (0.308 g, 70%). m.p. 207–208° C.

A mixture of this compound (0.222 g, 0.6 mmol) and sodium borohydride (45 mg, 1.2 mmol) in THF (10 mL) was heated at reflux for 30 min. The cool reaction was poured into water, made basic with 2.5 N NaOH and extracted with ether. The organic layers were washed with brine, dried ($MgSO_4$) and concentrated. The crude product was purified by recrystallization from hexanes to afford the title compound as a white solid (0.114 g, 76%). m.p. 101–102° C.

EXAMPLE 276

2-Chloro-N-ethyl-6-(trimethylsilyl)-3-[(trimethylsilyl)ethynyl]benzamide

To a slurry of the compound of Example 239 (0.763 g, 2.0 mmol), bis(triphenylphosphine)palladium dichloride (28 mg, 0.04 mmol) and cuprous iodide (15 mg, 0.08 mmol) in anhydrous triethylamine (10 mL) was added trimethylsilylacetylene (0.236 g, 2.4 mmol). The brown slurry was stirred at RT for 3.5 h, concentrated, slurried in ether and filtered through silica gel (ether). The crude product was further purified by flash chromatography (ethyl acetate/hexanes) followed by recrystallization from hexanes to afford the title compound as white crystals (0.618 g, 88%). m.p. 131–132° C.

EXAMPLE 277

2-Chloro-3-ethenyl-N-ethyl-6-(trimethylsilyl) benzamide

To a solution of the compound of Example 239 (0.382 g, 1.0 mmol), tetrakis(triphenylphosphine)palladium(O) (23 mg, 0.02 mmol) and 2.6-di-t-butyl-4-methylphenol (1.5 mg) in toluene (10 mL) was added vinyltributyltin (0.349 g, 1.1 mmol). The light yellow solution was heated at reflux for 24 h, additional tetrakis(triphenylphosphine)palladium(O) (15 mg) was added, and reflux was continued for 24 h. The cool mixture was diluted with ether, filtered through Celite, concentrated and purified by RC (ethyl acetate/hexanes). The product was further purified by recrystallization from pentane to afford the title compound as white needles (0.060 g, 21%). m.p. 127–128° C.

EXAMPLE 278

[2-Chloro-6-(trimethylsilyl)benzoyl] ethylphosphoramidic acid, diethyl ester

To a solution of 5.0 g (29.0 mmol) of diethyl chlorophosphate in 70 mL dichloroethane cooled on an ice bath was added 4.1 g (63.8 mmol) of ethylamine (70% aq). The mixture was allowed to stir at RT for 30 min and was then partitioned between ether and water. The organic layer was washed with brine, dried ($MgSO_4$), and was filtered. The filtrate was evaporated in vacuo and the residue was kugelrohr distilled (0.8 torr, 90° C.) to yield 2.7 g (52%) of diethyl N-ethylphosphoramidate as a colorless oil.

To a solution of 0.8 g (4.4 mmol) of this phosphoramidate in 40 mL dry THF cooled to –70° C. was added 1.8 mL (4.5 mmol) of n-BuLi (2.5 M in hexane). The mixture was stirred at –70° C. for 10 min and to the mixture was added a solution of 1.0 g (4.05 mmol) of the compound of Example b in 10 mL dry THF. The mixture was allowed to warm to RT and was stirred for another 45 min. The mixture was then heated to reflux for 30 min and was allowed to cool to RT. The mixture was partitioned between ether and water. The organic layer was washed with brine, dried ($MgSO_4$), and was filtered through silica gel. The filtrate was evaporated in vacuo and the residue was chromatographed (HPLC, 35% ethyl acetate/hexane) to yield 1.0 g (62%) of a colorless oil. $n_D^{25}$=1.5060.

EXAMPLE 279

2-Chloro-N-ethyl-N-[(methylthio)methyl]-6-(trimethylsilyl)benzamide

To a solution of 2.0 g (7.8 mmol) of the compound of Example 45 in 30 mL dry THF was added 7.9 mL (7.9 mmol) sodium bis(trimethylsilyl)amide (1.0 M in THF). To the resulting mixture was added 1.0 g (10.4 mmol) chloromethyl methylsulfide. The mixture was stirred for 15 min and another 0.65 g (6.7 mmol) of chloromethyl methylsulfide was added. Stirring at RT was continued for 1 h and the mixture was then heated to reflux for 28 hours. The mixture was allowed to cool to RT and was then partitioned between ether and water. The organic layer was washed with brine, dried ($MgSO_4$), and was filtered through silica gel. The filtrate was evaporated in vacuo and the residue was chromatographed (HPLC, 8% ethyl acetate/hexane) to yield 1.1 g (45%) of a colorless oil. $n_D^{25}$=1.5526.

EXAMPLE 280

2-[(1,1-Dimethylethyl)sulfonyl]-N-ethyl-6-fluorobenzamide

A 0° C. solution of N-ethyl 2-fluoro-6-(1,1-dimethylethylthio)benzamide, described in Example 194, (0.15 g, 0.59 mmol) in methanol (5 mL) was combined with a 0° C. solution of OXONE® (1.08 g, 1.76 mmol) in water (5 mL). This mixture was stirred overnight, then was poured into 25% aq sodium metabisulfite (100 mL) and extracted with ether (3×100 mL). The combined organics were washed with brine followed with water, then was dried (MgSO$_4$) and concentrated to give the title compound as a clear oil.

EXAMPLE 281

2-Chloro-6-[(1,1-dimethylethyl)methylamino]-N,N-(diethyl)benzamide

A solution of the N-tert-butyl b-lactam (3.3 g, 18.9 mmol) described in Example 188 and diethylamine (4.6 g, 62.4 mmol) in CH$_2$Cl$_2$ (100 mL) was stirred at RT overnight. The solvent was evaporated, then the residue was triturated with cyclohexane and the filtrate was concentrated to an oil. 500 mg of this material was purified by RC with EtOAc/cyclohexane to give 478 mg of N,N-diethyl-2-(N-tert-butylamino)benzamide as an orange oil, a 95% yield.

A mixture of N,N-diethyl-2-(N-tert-butylamino) benzamide (4.2 g, 17 mmol), potassium carbonate (3.1 g, 22 mmol), and MeI (3.1 g, 22 mmol) in DMF (75 mL) was heated overnight at 40° C. The reaction was not complete, so additional MeI (3.1 g, 22 mmol) was added and the reaction heated at 40° C. for 1 d, then was partitioned between EtOAc and water. The EtOAc was dried (MgSO$_4$), concentrated, and purified by HPLC with 1:4 ethyl acetate/cyclohexane to afford 3.22 g of N,N-diethyl-2-(N-methyl-N-tert-butylamino)benzamide as a yellow oil, a 72% yield.

A solution of 1.3M s-BuLi in cyclohexane (3.5 mL, 4.6 mmol) was added dropwise to a dry-ice/acetone cooled solution of TMEDA (0.7 mL, 4.8 mmol) in THF (10 mL), followed by the dropwise addition of a solution of N,N-diethyl-2-(N-methyl-N-tert-butylamino)benzamide (1.0 g, 3.8 mmol) in THF (5 mL). The reaction mixture was stirred at −78° C. for 50 min, then a solution of hexachloroethane (2.7 g, 11.4 mmol) in THF (5 mL) was added. This mixture was stirred for 30 min at −78° C., then was warmed to −30° C., diluted with water, and extracted with EtOAc (2×). The combined organic extracts were dried (MgSO$_4$), concentrated, and purified by HPLC with 3:17 EtOAc/cyclohexane to give 577 mg of the title compound as a yellow oil, a 51% yield.

EXAMPLE 282

2-Chloro-N-ethyl-5-(trimethylsilyl)-4-thiazolecarboxamide a) A mixture of 90% ethyl bromopyruvate (54.2 g, 0.25 mol) and thiourea (20 g, 0.263 mol) in 500 mL absolute ethanol was heated at reflux for 1 h and then stirred at ambient temperature for 2 h. Ethanol was removed in vacuo and the residue was suspended in ice-water and neutralized with solid potassium carbonate until basic. The solid was filtered, washed thoroughly with water and air-dried to give 42 g of ethyl-2-amino-4-thiazolecarboxylate.

b) To a mixture of copper (II) chloride (20 g, 0.15 mol) and 90% t-butyl nitrite (24 mL, 0.18 mol) in 500 mL acetonitrile at 60° C. was added in portions ethyl 2-amino-4-thiazolecarboxylate (21 g, 0.12 mol), maintaining the temperature at between 60–65° C. After the addition, the resulting reaction mixture was heated at 80° C. for 1 h, then cooled to RT and poured into a mixture of water, CH$_2$Cl$_2$ and 25 mL conc HCl. The aq layer was separated and extracted with CH$_2$Cl$_2$. The combined organic layers were washed with water, brine, dried and concentrated to give 21.5 g of ethyl 2-chloro-4thiazolecarboxylate.

c) A mixture of NaOH (1.9 g, 47.5 mmol) and ethyl-2-chloro-4-thiazolecarboxylate (7.6 g, 40 mmol) in 100 mL absolute ethanol was stirred at RT for 4 h. After that, ethanol was removed in vacuo and the residue was dissolved in water. The aq layer was washed with ether and then acidified with conc HCl. The solid was filtered and air dried to give 4 g of 2-chloro-4-thiazolecarboxylic acid.

d) 2-Chloro-4-thiazolecarboxylic acid chloride (prepared from 2-chloro-4-thiazolecarboxylic acid, thionyl chloride and a catalytic amount of DMF) was reacted with 70% ethylamine in water to yield 2-chloro-N-ethyl-4-thiazolecarboxamide. This compound was reacted with TMSCl using the method of step c of Example 248. Purification by flash chromatography with 3% ethyl acetate-hexane gave 2.5 g of the title compound as a light yellow oil in 55.6% yield. $n_D^{26}$ 1.5313.

EXAMPLE 283

2-Chloro-N-ethyl-3-(trimethylsilyl)-4-thiazolecarboxamide

2-Chlorothiazole was prepared from 2-aminothiazole according to step b of Example 282. Distillation yielded a clear liquid. b.p. 145–150° C. This compound was reacted with n-BuLi and dry ice using the method of step a of Example 258 to yield 2-chloro-5-thiazolecarboxylic acid.

This compound was reacted with 70% ethylamine, followed by TMSCl using the methods of Example 248 to yield 0.9 g of the title compound as white solid in 54.2% yield. m.p. 101–103° C.

EXAMPLE 284

N-Ethyl-5-(trimethylsilyl)-1H-pyrazole-1-carboxamide

To a solution of pyrazole (1.7 g, 25 mmol) and 4 mL triethylamine in 50 mL dry THF was added ethyl isocyanate (2 g, 28 mmol) at 0° C. and the resulting reaction solution was stirred at RT for 18 h. Ethyl acetate and 2N HCl were added. The aq layer was separated and extracted with ethyl acetate. The combined ethyl acetate layers were washed with brine, dried and concentrated in vacuo to give an oil. The oil was triturated with cold hexane to give 2.5 g of N-ethyl-1H-pyrazole-1-carboxamide as a white solid.

A solution of this compound in THF was metallated with lithium diisopropylamide (prepared by diisopropylamine and 2.5M of n-BuLi in hexane as in step a of Example 250) and quenched with TMSCl as in Example 248 to give 0.6 g of the title compound as an orange oil. $n_D^{26}$ 1.6627.

EXAMPLE 285

2-Chloro-N-ethyl-6-(1,1-dimethylethyl)benzamide 2-tert-butyl-N-ethylbenzamide was prepared from 2-tert-butylbenzoyl chloride, prepared in Example 186, and 70% ethylamine in water according to the method of step b of Example 248.

To a solution of 2-tert-butyl-N-ethylbenzamide (44 g, 215 mmol) and TMEDA (70 mL, 446 mmol) in 500 mL THF at −70° C. under a positive nitrogen atmosphere was added at a rapid stream 520 mL 1.3M s-BuLi in cyclohexane, maintaining the temperature at below −60° C. After the addition was complete, the resulting reaction solution was warmed to −30° C. and stirred at between −30° C. and −26° C. for 50 min. The solution was then cooled to below −70° C. and a solution of hexachloroethane (80 g) in 250 mL THF was added at between −70 and −65° C. Stirring at below −70° C. was continued for 0.5 h. The resulting reaction solution was then poured into water. CH$_2$Cl$_2$ and 3N HCl were added. The aq layer was separated and extracted with CH$_2$Cl$_2$. The combined organic layers were washed with water, dried and concentrated in vacuo. The solid was triturated with hexane and then purified by flash chromatography with 15% ethyl acetate/hexane as eluent to give the desired product as a white solid. m.p. 121–123° C.

EXAMPLE 286

4,5-Dimethyl-N-ethyl-3-(trimethylsilyl)-2-thiophenecarboxamide

The title compound was prepared from methyl ethyl ketone using the methods of Example 274 and was obtained as a white solid. m.p. 77–80° C.

EXAMPLE 287

5-Chloro-N-hydroxy-N-(1-methylethyl)-3-(trimethylsilyl)-2-thiophenecarboxamide

5-Chloro-3-(trimethylsilyl)-2-thiophenecarboxylic acid chloride was prepared by the reaction of 1 g 5-chloro-3-(trimethylsilyl)-2-thiophenecarboxylic acid (prepared as in Example 263) and 6 mL thionyl chloride, using the procedure of step a in Example 248. This product was dissolved in CH$_2$Cl$_2$ at 0° C. and added to a mixture of N-isopropylhydroxylamine hydrochloride (0.55 g, 5 mmol) and 4 g NaHCO$_3$ in 20 mL CH$_2$Cl$_2$ and 20 mL water. The resulting reaction mixture was stirred at RT for additional 3 h. The organic layer was separated, washed with brine, dried and concentrated. The residue was purified by flash chromatography with 8% ethyl acetate/hexane to give 80 mg of the title compound. m.p. 146–150° C.

EXAMPLE 288

N-Ethyl-1-methyl-5-(trimethylsilyl)-1H-pyrazole-4-carboxamide

A solution of ethyl (ethoxymethylene)cyanoacetate (68 g, 0.4 mol) and methylhydrazine (18.5 g, 0.4 mol) in 200 mL absolute ethanol was refluxed for 1.5 h, then cooled to RT and filtered. The filtrate was concentrated in vacuo and the residue was triturated with ether to give 54 g of crude ethyl 5-amino-1-methyl-1H-pyrazole-4-carboxylate in 75.4% yield.

To a solution of 90% t-butyl nitrite (50 mL, 0.37 mol) in 200 mL DMF was added in portions ethyl 5-amino-1-methyl-1H-pyrazole-4-carboxylate (39 g, 0.23 mol), maintaining the temperature at around 30° C. After the addition, the resulting mixture was warmed to 50° C. and stirred at that temperature for 0.5 h. The mixture was poured into 100 mL conc HCl and 40 mL water and extracted with CH$_2$Cl$_2$. The organic solution was washed with water, brine, dried and concentrated. Vacuum distillation of the residue gave 32.4 g of ethyl 1-methyl-1H-pyrazole-4-carboxylate as a clear liquid. b.p. 65–80° C. at 0.1 torr.

A solution of ethyl 1-methyl-1H-pyrazole-4-carboxylate (20.2 g, 131 mmol) and NaOH (6.3 g, 158 mmol) in 200 mL absolute ethanol was refluxed for 2 h and stirring was continued at RT for 18 h. After that, the solvent was removed in vacuo. The residue was dissolved in water. The aq solution was washed with ether and acidified with concentrated HCl. The solid was filtered, washed with water and air-dried to give 14.2 g of 1-methyl-1H-pyrazole-4-carboxylic acid in 86% yield.

N-Ethyl-1-methyl-1H-pyrazole-4-carboxamide was prepared from 1-methyl-1H-pyrazole-4-carboxylic acid and 70% ethylamine in water using the methods of steps a and b of Example 248. The product was purified by flash chromatography with 10% ethyl acetate-hexane and recovered as a white solid in 54.7% yield. m.p. 103–106° C.

This compound was reacted with TMSCl as in Example 248 to give 1.2 g of the title compound as a white solid. m.p. 77–81° C.

| Ex No. | Elemental Analyses Elements (Calculated/Found) |
|---|---|
| 2 | C 67.41, 66.98; H 9.29, 9.31; N 5.62, 5.52. |
| 3 | C 68.38, 38.36; H 9.56, 9.59; N 5.62, 5.31. |
| 4 | C 62.88, 62.95; H 8.29, 8.31; N 5.24, 5.21. |
| 6 | C 77.68, 76.22; H 10.19, 10.18; N 5.66, 5.50. |
| 7 | C 44.90, 44.91; H 5.92, 5.93. |
| 10 | C 66.82, 66.65; H 9.35, 9.37; N 4.33, 4.24. |
| 14 | C 70.04, 69.94; H 10.03, 10.04; N 4.80, 4.75. |
| 15 | C 59.23, 59.42; H 7.81, 7.97; N 4.93, 4.78. |
| 18 | C 60.48, 60.37; H 8.12, 8.12; N 4.70, 4.76. |
| 22 | C 57.86, 58.00; H 7.47, 7.52; N 5.19, 5.26. |
| 23 | C 60.48, 60.34; H 8.12, 8.08; N 4.70, 4.75. |
| 35 | C 65.97, 65.74; H 6.99, 6.94; N 4.05, 3.99. |
| 36 | C 61.61, 61.93; H 8.40, 8.17; N 4.49, 4.23. |
| 38 | C 55.70, 55.90; H 7.01, 7.07; N 4.64, 4.68. |
| 39 | C 59.23, 59.36; H 7.81, 7.85. |
| 41 | C 60.98, 60.88; H 7.51, 7.52; N 4.74, 4.73. |
| 43 | C 61.16, 61.13; H 7.98, 7.99; N 3.96, 3.94. |
| 44 | C 69.26, 69.22; H 9.81, 9.82; N 5.05, 5.03. |
| 46 | C 56.07, 55.96; H 7.39, 7.44. |
| 50 | C 63.35, 63.41; H 8.73, 8.77. |
| 55 | C 60.17, 59.91; H 7.74, 7.80; N 4.68, 4.63. |
| 56 | C 58.91, 58.62; H 7.42, 7.35; N 4.91, 4.94. |
| 57 | C 64.01, 63.88; H 8.60, 8.65; N 4.98, 4.94. |
| 58 | C 68.38, 68.20; H 9.56, 9.62; N 5.32, 5.27. |
| 59 | C 60.48, 60.56; H 8.12, 8.14; N 4.70, 4.68. |
| 60 | C 69.26, 69.31; H 9.81, 9.83; N 5.05, 5.06. |
| 61 | C 56.76, 56.79; H 6.99, 7.02; N 4.41, 4.43. |
| 63 | C 68.38, 68.25; H 9.56, 9.47; N 5.32, 5.58. |
| 64 | C 68.38, 68.14; H 9.56, 9.46; N 5.32, 5.61. |
| 66 | C 62.64, 62.49; H 8.66, 8.56; N 4.30, 4.57. |
| 67 | C 65.97, 66.01; H 6.99, 7.00; N 4.05, 4.11. |
| 68 | C 65.27, 65.30; H 9.31, 9.17; N 3.81, 3.90. |
| 69 | C 52.82, 52.97; H 6.65, 6.61; N 4.40, 4.44. |
| 77 | C 52.82, 52.88; H 6.28, 6.27. |
| 78 | C 54.42, 54.48; H 6.68, 6.63. |
| 79 | C 54.42, 54.35; H 6.68, 6.63. |
| 80 | C 55.88, 55.99; H 7.03, 7.05. |
| 81 | C 55.88, 55.70; H 7.03, 6.99. |
| 85 | C 61.61, 61.63; H 8.40, 8.37; N 4.49, 4.47. |
| 88 | C 55.70, 55.80; H 7.01, 7.02; N 4.64, 4.69. |
| 95 | C 61.61, 61.50; H 8.40, 8.41; N 4.49, 4.75. |
| 96 | C 65.27, 64.62; H 9.31, 9.16. |
| 97 | C 60.17, 60.42; H 7.74, 7.80. |
| 98 | C 64.01, 63.76; H 8.60, 8.52. |
| 101 | C 68.10, 68.21; H 7.79, 7.81; N 3.61, 3.66. |
| 104 | C 67.08, 66.83; H 8.04, 7.99. |
| 105 | C 67.11, 67.00; H 6.76, 6.78. |
| 125 | C 60.79, 60.95; H 6.60, 6.56. |
| 127 | C 64.47, 64.58; H 9.02, 9.06. |
| 128 | C 58.60, 58.31; H 7.99, 7.94. |
| 130 | C 58.96, 59.11; H 7.42, 7.40; N 4.30, 4.25. |
| 164 | C 59.23, 59.35; H 7.81, 7.78. |
| 166 | C 60.48, 60.59; H 8.12, 8.13; N 4.70, 4.71. |
| 169 | C 56.06, 56.26; H 7.39, 7.33. |
| 172 | C 51.72, 51.98; H 6.68, 6.75. |
| 186 | C 74.71, 73.93; H 10.23, 10.08. |
| 189 | C 63.70, 63.78; H 8.20, 8.15; N 9.91, 9.86. |
| 195 | C 60.17, 57.51; H 7.41, 6.65. |
| 249 | C 52.12, 51.45; H 8.41, 8.32; N 4.68, 4.62. |
| 281 | C 64.74, 64.65; H 8.49, 8.48; N 9.44, 9.47. |

Biological Assays

The compounds prepared in the above examples have demonstrated control of Gg in one or both of the following test methods. The results are shown in the table below.

In vitro Assay

The test compounds (0.25 mL of an appropriate stock solution in acetone) are incorporated into 25 mL minimal media agar [prepared by autoclaving a solution of 17.5 g Czapek Dox broth (Difco), 7.5 g purified agar or Bacto-agar (Difco), and 500 mL distilled/deionized water, and then adding 50 μL of 1 mg/mL thiamine hydrochloride and 50 μL of 1 mg/mL biotin in 5% ethanol] and plates are prepared.

Each plate is inoculated by placing in a triangular shape three 4-mm plugs of *Gaeumannomyces graminis* var. tritici (Ggt) grown on the minimal media agar described above. The plates are incubated in the dark at 19–20° C. for 4 to 5 days. The growth of the fungus is measured as the diameter of the mycelial growth. The result is expressed as Percent Inhibition, calculated as [1−[(mm growth on treated plate−4)/(mm growth on control plate−4))]]×100.

In vivo Assay

Compounds are tested for control of Ggt on 'Bergen' or 'Anza' varieties of wheat grown in 3-inch square pots containing soil infested with Ggt. The infestation is accomplished by mixing the soil with an inoculum prepared by growing Ggt on 1/4 strength potato dextrose agar (4.875 g potato dextrose agar, 5.0 g Bacto agar, 500 mL distilled, deionized water) in plates and using plugs from the plates to infest sterile oats (400 cc whole oats, 350 mL deionized water, autoclaved). After a one-month incubation period at room temperature, the oats are dried and mixed with the soil at 4% v/v. Four wheat seeds are placed on top of the soil in each pot. The test compounds are prepared as an 1:9 acetone/water v/v solution containing 0.18% Tween® 20 to provide a treatment rate of 0.5 mg active ingredient per pot, treated with 3 mL test solution per pot. Five pots are used for each treatment level and the controls, which are untreated, inoculated and non-inoculated pots. After one hour drying time, the seeds are covered with more of the appropriate soil and a layer of vermiculite. The pots are placed in a growth chamber and watered each day. After four weeks, each pot is evaluated for evidence of disease by examination of the seminal roots of each plant under a dissecting microscope. A 0 to 5 rating scale having the following meanings is used:

0=no runner hyphae or lesions present

1=runner hyphae and a few small lesions present on <10% of root system

2=runner hyphae and small lesions present on 10–25% of root system

3=runner hyphae and lesions present on 25–50% of root system

4=runner hyphae and many, large, coalescing lesions on >50% of root system

5=root system and culm completely inundated with lesions and runner hyphae

From each set of five replicates a high and low score is eliminated and a replicate mean is calculated by the average of the remaining three scores. This mean score is then compared to the untreated control score and a percent disease control is calculated. These results are reported in the Table below. If the calculation resulted in "0" or less, as compared to the untreated control, a "N" is shown to indicate no control.

Test Results

| Ex. | In vitro (ppm) | | | In |
|---|---|---|---|---|
| No. | 10 | 1 | 0.1 | vivo |
| 1 | 74 | 53 | 6 | 91 |
| 2 | 72 | 36 | 14 | 74 |
| 3 | 75 | 58 | 19 | 100 |
| 4 | 57 | N | N | 54 |
| 5 | 29 | N | N | 24 |
| 6 | 47 | 2 | 7 | 37 |
| 7 | 100 | 77 | 42 | 93 |
| 8 | 100 | 97 | 19 | 85 |
| 9 | 71 | N | 3 | |
| 10 | 50 | N | N | |
| 11 | 24 | N | N | |
| 12 | 100 | 83 | 29 | 95 |
| 13 | 64 | 17 | 7 | 13 |
| 14 | 79 | 40 | 7 | 92 |
| 15 | 44 | N | N | |
| 16 | 76 | 27 | 11 | 3 |
| 17 | 64 | 64 | 59 | N |
| 18 | 100 | N | N | 97 |
| 19 | 29 | 7 | N | 38 |
| 20 | 61 | 14 | 7 | 36 |
| 21 | 100 | 100 | 100 | 100 |
| 22 | 46 | N | 13 | 91 |
| 23 | 71 | N | N | |
| 24 | 100 | N | N | |
| 25 | 89 | 15 | 19 | 56 |
| 26 | 97 | 95 | 95 | 99 |
| 27 | 64 | 13 | 15 | 33 |
| 28 | 100 | 100 | 60 | 86 |
| 29 | 100 | 100 | 100 | 97 |
| 30 | 80 | 60 | N | |
| 31 | 96 | 4 | N | |
| 32 | 100 | 100 | 75 | 85 |
| 33 | 100 | 44 | N | 12 |
| 34 | 100 | 100 | 97 | 100 |
| 35 | 93 | 7 | 3 | 46 |
| 36 | 100 | 69 | 26 | 88 |
| 37 | 87 | 63 | 17 | 83 |
| 38 | 100 | 79 | 53 | 95 |
| 39 | 92 | 82 | 49 | 99 |
| 40 | 53 | N | N | |
| 41 | 52 | 21 | 24 | |
| 42 | 30 | N | N | |
| 43 | 63 | N | N | |
| 44 | 39 | N | N | |
| 45 | 100 | 100 | 100 | 97 |
| 46 | 44 | 11 | 15 | |
| 47 | 70 | N | N | |
| 48 | 100 | 100 | 74 | 97 |
| 49 | 100 | 100 | 100 | 97 |
| 50 | 20 | 10 | 3 | |
| 51 | 100 | 19 | N | 77 |
| 52 | 98 | 81 | 53 | 96 |
| 53 | 95 | 19 | 9 | 65 |
| 54 | 43 | 2 | N | 52 |
| 55 | 100 | 81 | 49 | 100 |
| 56 | 74 | 31 | 10 | 91 |
| 57 | 90 | N | 10 | |
| 58 | 55 | 6 | 13 | |
| 59 | 26 | N | 6 | |
| 60 | 19 | N | N | |
| 61 | 49 | 29 | 9 | 1 |
| 62 | 69 | 3 | 8 | 9 |
| 63 | 69 | 40 | N | |
| 64 | 31 | 14 | 20 | |
| 65 | 100 | 56 | 39 | 95 |
| 66 | 58 | N | N | 3 |
| 67 | 100 | 19 | N | N |
| 68 | 41 | N | 8 | N |
| 69 | 100 | 81 | 51 | 67 |
| 70 | 44 | 15 | N | |
| 71 | N | 8 | 14 | 50 |
| 72 | 69 | 59 | N | |
| 73 | 83 | 60 | 13 | |

-continued

Test Results

| Ex. No. | In vitro (ppm) 10 | 1 | 0.1 | In vivo |
|---|---|---|---|---|
| 74 | 93 | 31 | 7 | 47 |
| 75 | 31 | 26 | 5 | |
| 76 | 79 | 45 | N | |
| 77 | 100 | 47 | 13 | N |
| 78 | 62 | 12 | 12 | |
| 79 | 65 | 12 | 12 | |
| 80 | 46 | 4 | N | |
| 81 | 46 | N | N | |
| 82 | 57 | N | 30 | 58 |
| 83 | 100 | 100 | 100 | 99 |
| 84 | 100 | 66 | N | |
| 85 | 59 | 7 | 7 | |
| 86 | 72 | 24 | N | |
| 87 | 100 | 100 | 93 | 96 |
| 88 | 73 | N | N | |
| 89 | 100 | 85 | 19 | 96 |
| 90 | 89 | 34 | 6 | |
| 93 | 26 | N | N | |
| 94 | 86 | 63 | 9 | |
| 95 | 100 | 62 | N | 63 |
| 96 | 48 | 15 | 7 | |
| 97 | 100 | 70 | 7 | |
| 98 | 100 | 81 | 22 | 97 |
| 99 | 95 | 72 | 5 | 59 |
| 101 | 62 | 21 | 10 | |
| 102 | 28 | 52 | 28 | |
| 103 | 92 | 55 | N | 26 |
| 104 | 71 | 26 | N | |
| 105 | 84 | 37 | 3 | |
| 106 | 97 | 95 | 95 | 100 |
| 107 | 24 | N | N | |
| 108 | 97 | 86 | 90 | |
| 109 | 83 | 10 | 10 | |
| 110 | 45 | 17 | 7 | |
| 111 | 100 | 66 | 14 | 48 |
| 112 | 100 | 96 | 81 | |
| 113 | 96 | 26 | N | |
| 114 | 100 | 85 | 38 | |
| 115 | 97 | 97 | 97 | |
| 116 | 33 | N | N | |
| 117 | 97 | 94 | 36 | |
| 118 | 38 | N | N | |
| 119 | 100 | 88 | 40 | |
| 120 | 100 | 26 | N | |
| 121 | 31 | 8 | 4 | |
| 122 | 67 | N | N | |
| 123 | 89 | 78 | 11 | |
| 124 | *62 | N | N | |
| 125 | 89 | N | N | |
| 126 | 93 | 4 | 15 | |
| 127 | 74 | 21 | N | |
| 128 | 50 | 8 | 4 | |
| 129 | 26 | 35 | 9 | |
| 130 | 39 | 13 | 16 | 1 |
| 131 | 3 | 6 | N | |
| 132 | 46 | 15 | 54 | N |
| 133 | 18 | 3 | 13 | N |
| 134 | 39 | 3 | N | N |
| 135 | 39 | 17 | 22 | |
| 136 | 100 | 26 | 3 | |
| 137 | 100 | 61 | 17 | |
| 138 | 97 | 36 | 14 | |
| 139 | 100 | 53 | 11 | |
| 140 | 81 | 19 | 19 | |
| 141 | 100 | 64 | 19 | |
| 142 | 59 | N | N | |
| 143 | 74 | 13 | 5 | |
| 144 | 59 | 11 | N | |
| 145 | 27 | N | N | |
| 146 | 84 | 65 | 14 | |
| 147 | 58 | N | N | |
| 148 | 53 | N | N | |
| 149 | 80 | N | N | |
| 150 | 83 | 74 | 34 | 96 |
| 151 | 57 | 71 | N | 97 |
| 152 | 86 | 71 | N | 54 |
| 153 | 91 | 88 | N | 29 |
| 154 | 69 | N | N | |
| 155 | 90 | 64 | N | 93 |
| 156 | 72 | 33 | 9 | |
| 157 | 91 | 23 | 7 | 0 |
| 158 | 44 | 33 | 2 | |
| 159 | 100 | 55 | 12 | 0 |
| 160 | 88 | 63 | 17 | 5 |
| 161 | 61 | 17 | 22 | |
| 162 | 57 | N | 3 | |
| 163 | 100 | 85 | 24 | |
| 164 | 70 | 3 | 3 | |
| 165 | 100 | 76 | N | 63 |
| 166 | 73 | N | 4 | 15 |
| 167 | 96 | 86 | 46 | 93 |
| 168 | 100 | 96 | 57 | |
| 169 | 100 | 31 | N | |
| 170 | 63 | 9 | 12 | |
| 171 | 97 | 88 | 48 | 87 |
| 172 | 100 | 100 | 94 | 99 |
| 173 | 92 | 12 | 4 | |
| 174 | 100 | 65 | 12 | 0 |
| 175 | 60 | 48 | 35 | |
| 176 | 97 | 97 | 83 | |
| 177 | 100 | 19 | 11 | |
| 178 | 54 | 15 | N | |
| 179 | 91 | 88 | 85 | 97 |
| 180 | 90 | 82 | 85 | 96 |
| 181 | 58 | 33 | 12 | |
| 182 | 73 | 58 | 30 | |
| 183 | 56 | 35 | 24 | |
| 184 | 83 | 11 | N | |
| 185 | 72 | 56 | 48 | |
| 186 | 67 | N | N | |
| 187 | 97 | 27 | 13 | 24 |
| 188 | 100 | 71 | 29 | 15 |
| 189 | 65 | 13 | 4 | |
| 190 | 80 | 76 | 24 | |
| 191 | 88 | 88 | 60 | 88 |
| 192 | 95 | 95 | 86 | 99 |
| 193 | 57 | 30 | 35 | |
| 194 | 100 | 100 | 82 | |
| 195 | 56 | 29 | 35 | |
| 196 | 100 | 56 | 3 | |
| 197 | 85 | 23 | 3 | |
| 198 | 75 | 32 | 7 | |
| 199 | 74 | 29 | 9 | |
| 200 | 100 | 100 | 92 | 65 |
| 201 | 100 | 50 | 31 | 65 |
| 202 | 88 | 58 | 33 | 3 |
| 203 | 91 | 84 | 79 | |
| 204 | 74 | N | N | 43 |
| 205 | 81 | 47 | 5 | |
| 206 | 100 | 97 | 86 | |
| 207 | 97 | 90 | 31 | |
| 208 | 97 | 83 | N | |
| 209 | 100 | 90 | 28 | |
| 210 | 94 | 88 | 85 | 74 |
| 211 | 90 | 82 | N | 96 |
| 212 | 90 | 54 | 77 | 96 |
| 213 | 79 | 82 | 9 | 87 |
| 214 | 77 | 6 | 3 | |
| 215 | 100 | 96 | 46 | 57 |
| 216 | 92 | 54 | 25 | 68 |
| 217 | 100 | 68 | 16 | 0 |
| 218 | 100 | 94 | 18 | 99 |
| 219 | 100 | 94 | 50 | 97 |
| 220 | 100 | 100 | 75 | 97 |
| 221 | 85 | 46 | 15 | |
| 222 | 96 | N | N | |

-continued

| Test Results | | | | |
|---|---|---|---|---|
| Ex. | In vitro (ppm) | | | In |
| No. | 10 | 1 | 0.1 | vivo |
| 223 | 96 | 93 | 48 | 82 |
| 224 | 93 | 27 | N | 21 |
| 225 | 95 | 64 | 18 | |
| 226 | 100 | 91 | 32 | |
| 227 | 100 | 68 | 36 | 34 |
| 228 | 96 | 87 | N | 84 |
| 229 | 88 | 28 | N | |
| 230 | 96 | 96 | 88 | |
| 231 | 96 | 76 | N | |
| 232 | 95 | 97 | 92 | 78 |
| 233 | 76 | 24 | 28 | |
| 234 | 81 | 32 | N | |
| 235 | 70 | N | 3 | |
| 236 | 86 | 68 | N | |
| 237 | 96 | 93 | 44 | |
| 238 | 72 | N | N | |
| 239 | 87 | 57 | 22 | |
| 240 | 65 | 22 | 26 | |
| 241 | 100 | 87 | 13 | |
| 242 | 67 | N | 27 | |
| 243 | 83 | 10 | 23 | |
| 244 | 53 | 20 | 10 | |
| 245 | 100 | 100 | 50 | |
| 246 | 61 | 2 | N | |
| 247 | 59 | 16 | N | |
| 248 | 100 | 10 | 10 | |
| 249 | 100 | 48 | 17 | 60 |
| 250 | 41 | N | N | |
| 251 | 97 | 36 | 3 | |
| 252 | 100 | 28 | 5 | |
| 253 | 62 | 14 | N | |
| 254 | 100 | 97 | 97 | 40 |
| 255 | 73 | N | N | |
| 256 | 100 | N | N | |
| 257 | 100 | 23 | 3 | |
| 258 | 42 | 19 | 19 | |
| 259 | *80 | 11 | 19 | |
| 260 | 77 | N | N | |
| 261 | 78 | 25 | 14 | |
| 262 | 100 | 70 | 13 | |
| 263 | 50 | N | 7 | |
| 264 | 100 | 88 | 2 | |
| 265 | 100 | 14 | 5 | |
| 266 | 100 | 61 | 21 | 4 |
| 267 | 61 | 64 | 18 | |
| 268 | 100 | N | N | |
| 269 | 100 | 91 | N | 4 |
| 270 | 100 | 100 | 96 | 87 |
| 271 | 100 | 100 | 95 | 97 |
| 272 | 100 | 23 | 14 | 0 |
| 273 | 100 | 48 | 35 | |
| 274 | 67 | 10 | N | |
| 275 | 94 | 81 | 22 | |
| 276 | 84 | 63 | N | |
| 277 | 94 | 81 | 69 | |
| 278 | 75 | 50 | N | |
| 279 | 47 | N | N | |
| 280 | 38 | 21 | 24 | |
| 281 | 43 | N | 4 | |
| 282 | 78 | 15 | 3 | |
| 283 | 42 | 3 | N | |
| 284 | *91 | 35 | 23 | |
| 285 | 75 | 50 | N | |
| 286 | 100 | 93 | 76 | |
| 287 | 78 | 71 | 64 | |
| 288 | 53 | N | N | |

*Tested at 50 ppm.

Field Tests

The compounds of Examples 1–90, 93–99, and 101–288 are combined with various adjuvants, carriers, and other additives and mixed with wheat and barley seed at rates of from 0.01 to 50 g active ingredient per kg of seed which reduce the incidence of Gg in previously infested fields compared to check fields seeded with untreated seed.

| COMPOSITION EXAMPLES | |
|---|---|
| | Wt. Pct. |
| Suspension Concentrate: | |
| Compound No. 45 | 48.900 |
| Polyoxypropylene-polyoxyethylene block copolymer | 2.550 |
| Sodium Lignin Sulfonate | 2.040 |
| 10% Dimethylpolysiloxane Emulsion | 1.020 |
| 1% Xanthan gum solution | 0.990 |
| Water | 43.250 |
| Emulsifiable Concentrate: | |
| Compound No. 26 | 13.5 |
| Ethoxylated sorbitan (20EO) | 5.0 |
| C9 Aromatics | 81.5 |
| Wettable Powder: | |
| Compound No. 12 | 75.0 |
| Sodium lignin sulfonate | 3.0 |
| Sodium N-methyl-N-oleyl-taurate | 1.0 |
| Kaolinite clay | 11.0 |
| Granule: | |
| Compound No. 138 | 1.0 |
| Propylene glycol | 5.0 |
| Montmorillonite (24/48 mesh) | 94.0 |
| Dust: | |
| Compound No. 48 | 50.0 |
| Graphite | 10.0 |
| Kaolinite clay | 40.0 |

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

What is claimed is:

1. A method of controlling disease in a plant caused by Gaeumannomyces sp. comprising applying to the plant locus a fungicidally effective amount of a fingicide of the formula:

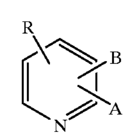

wherein A is selected from the group consisting of —C(X)-amine, wherein the amine is substituted with a first and a second amine substituent respectively, —C(O)—$SR_3$, —NH—C(X)$R_4$ and —C(=$NR_3$)—$XR_7$ or an alkylaminocarbonyl and a hydrogen; wherein X is O or S;

wherein the first amine substituent is selected from the group consisting of $C_1$–$C_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, a 5-membered heteroaryl, $C_3$–$C_6$ cycloalkyl and $C_5$–$C_6$ cycloalkenyl; phenyl optionally substituted with one or more $C_1$–$C_4$ straight or branched alkyl, alkenyl, or alkynyl groups or mixtures thereof, cycloalkyl, cycloalkenyl, haloalkyl, alkoxy and nitro; $C_3$–$C_6$ cycloalkyl, $C_5$–$C_6$ cycloalkenyl, alkoxy, alkenoxy, alkynoxy, dialkylamino, and alkylthio;

and the second amine substituent is selected from the group consisting of hydrogen, $C_1$–$C_6$ straight or branched alkyl, alkenyl, or alkynyl groups or mixtures thereof optionally substituted with one or more halogen; hydroxy, alkylcarbonyl, haloalkylcarbonyl, alkoxycarbonyl, and dialkylphosphonyl;

wherein B is —$W_m$—$Q(R_2)_3$;

Q is C or Si;

W is —$C(R_3)_p H_{(2-p)}$—, —$N(R_3)_m H_{(1-m)}$—, —$S(O)_p$—, or —O—;

m is 0 or 1;

p is 0, 1, or 2;

each $R_2$ is independently selected from alkyl, alkenyl, alkynyl, cycloalkyl, cycloalkenyl and phenyl, each optionally substituted with $R_4$ or halogen; alkoxy, alkylthio, alkylamino, and dialkylamino;

wherein two $R_2$ groups may be combined to form a cyclo group with Q;

$R_3$ is $C_1$–$C_4$ alkyl;

$R_4$ is $C_1$–$C_4$ alkyl, haloalkyl, alkoxy, alkylthio, alkylamino, or dialkylamino; and $R_7$ is $C_1$–$C_4$ alkyl, haloalkyl, or phenyl, optionally substituted with halo, nitro, or $R_4$;

or an agronomic salt thereof;

wherein R is 0, 1, 2, 3 or 4 and each R is independently selected from;

a) halo, formyl, cyano, amino, nitro, thiocyanato, isothiocyanato, trimethylsilyl, and hydroxy;

b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsufinyl, or alkylsulfonyl;

c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;

d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo.

2. The method of claim 1 wherein A is —C(O)-amine, wherein the first amine substituent is $C_1$–$C_{10}$ straight or branched alkyl, alkenyl or alkynyl group optionally substituted with one or more halogen and the second amine substituent is hydrogen.

3. The method of claim 2 wherein $W_m$ is —O— and Q is C.

4. The method of claim 3 wherein $R_2$ is $C_1$–$C_4$ alkyl or haloalkyl.

5. The method of claim 2 wherein A is ethylaminocarbonyl.

6. The method of claim 5 wherein there is only one R group, which is methyl or halo.

7. The method of claim 1 wherein the composition also comprises an adjuvant and wherein the fungicidally effective amount of the fungicide is an amount which is effective to control Take-All.

8. The method of claim 5 wherein R is adjacent to A.

9. The method of claim 2 wherein m is 0 and Q is Si.

10. The method of claim 3 wherein R is 0.

* * * * *